(12) United States Patent
Short et al.

(10) Patent No.: US 12,351,537 B2
(45) Date of Patent: Jul. 8, 2025

(54) DIMETHOXYPHENYLALKYLAMINE ACTIVATORS OF SEROTONIN RECEPTORS

(71) Applicant: Atai Therapeutics Inc., New York, NY (US)

(72) Inventors: Glenn Short, Encinitas, CA (US); Robert B. Perni, Encinitas, CA (US); Benjamin Robert Difrancesco, Encinitas, CA (US); Tanweer A. Khan, Encinitas, CA (US)

(73) Assignee: Atai Therapeutics, Inc., New York, NY (US)

( * ) Notice: Subject to any disclaimer, the term of this patent is extended or adjusted under 35 U.S.C. 154(b) by 0 days.

(21) Appl. No.: 18/435,857

(22) Filed: Feb. 7, 2024

(65) Prior Publication Data

US 2024/0294461 A1 Sep. 5, 2024

Related U.S. Application Data

(63) Continuation of application No. 17/835,764, filed on Jun. 8, 2022, now Pat. No. 11,926,574.
(Continued)

(51) Int. Cl.
*C07C 225/16* (2006.01)
*A61K 31/13* (2006.01)
(Continued)

(52) U.S. Cl.
CPC .......... *C07C 225/16* (2013.01); *C07C 381/10* (2013.01)

(58) Field of Classification Search
None
See application file for complete search history.

(56) References Cited

U.S. PATENT DOCUMENTS

| 4,239,903 A | 12/1980 | Isoda et al. |
| 5,807,897 A | 9/1998 | Warawa et al. |

(Continued)

FOREIGN PATENT DOCUMENTS

| EP | 0883599 B1 | 6/2002 |
| JP | 2023531311 A | 7/2023 |

(Continued)

OTHER PUBLICATIONS

Alves de Barros et al., "Synthesis of 25X-BOMes and 25X-NBOHs (X=H, I, Br) for pharmacological studies and as reference standards for forensic purposes," Tetrahedron Letters (2021), 66, 152804 4 pages.
(Continued)

*Primary Examiner* — Renee Claytor
*Assistant Examiner* — Jennifer C Sawyer
(74) *Attorney, Agent, or Firm* — COOLEY LLP

(57) ABSTRACT

Provided herein are compounds of Formula (I), or pharmaceutically acceptable salt thereof, wherein $R_1$, $R_2$, $R_3$, $R_4$, $R_5$, $R_6$, and n are defined herein. Also provided herein are pharmaceutical compositions comprising a compound of Formula (I) or pharmaceutically acceptable salt thereof, and methods of using a compound of Formula (I) or pharmaceutically acceptable salt thereof, e.g., in the treatment of a mental health disease or disorder.

(Continued)

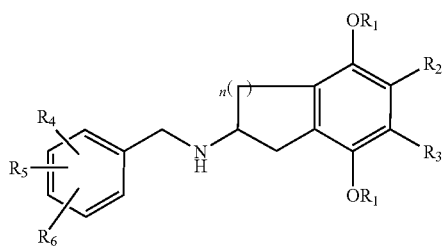

(I)

11 Claims, 1 Drawing Sheet

Related U.S. Application Data

(60) Provisional application No. 63/241,662, filed on Sep. 8, 2021, provisional application No. 63/208,391, filed on Jun. 8, 2021.

(51) Int. Cl.
*A61P 25/00* (2006.01)
*C07C 381/10* (2006.01)

(56) References Cited

U.S. PATENT DOCUMENTS

| | | |
|---|---|---|
| 6,201,025 B1 | 3/2001 | Dax et al. |
| 6,225,352 B1 | 5/2001 | Horwell et al. |
| 9,101,613 B2 | 8/2015 | Laudon et al. |
| 9,720,005 B2 | 8/2017 | McConnell et al. |
| 10,703,711 B2 | 7/2020 | Singh et al. |
| 11,306,059 B2 | 4/2022 | Weeber et al. |
| 11,629,127 B2 | 4/2023 | Weeber et al. |
| 11,827,580 B2 | 11/2023 | Short et al. |
| 11,827,582 B2 | 11/2023 | Singh et al. |
| 11,962,574 B2 | 4/2024 | Proulx et al. |
| 2002/0115715 A1 | 8/2002 | Dax et al. |
| 2003/0079301 A1 | 5/2003 | Sauter et al. |
| 2003/0199497 A1 | 10/2003 | Ruat et al. |
| 2005/0152858 A1 | 7/2005 | Bertz et al. |
| 2007/0099909 A1 | 5/2007 | Chen et al. |
| 2007/0196395 A1 | 8/2007 | Mackerell et al. |
| 2008/0248511 A1 | 10/2008 | Daily et al. |
| 2008/0318957 A1 | 12/2008 | Glinka et al. |
| 2009/0275563 A1 | 11/2009 | Bonaventure |
| 2010/0113539 A1 | 5/2010 | Scott et al. |
| 2010/0130742 A1 | 5/2010 | Harris et al. |
| 2012/0028995 A1 | 2/2012 | Ansorge et al. |
| 2012/0283298 A1 | 11/2012 | Crider et al. |
| 2015/0346226 A1 | 12/2015 | McConnell et al. |
| 2019/0315689 A1 | 10/2019 | Chen et al. |
| 2020/0325124 A1 | 10/2020 | Lavoie et al. |
| 2021/0052519 A1 | 2/2021 | Singh et al. |
| 2021/0145851 A1 | 5/2021 | Stamets |
| 2021/0315860 A1 | 10/2021 | Hopkins et al. |
| 2021/0403425 A1 | 12/2021 | Bryson |
| 2023/0138118 A1 | 5/2023 | Short et al. |
| 2023/0202965 A1 | 6/2023 | Short et al. |
| 2023/0331658 A1 | 10/2023 | Singh et al. |
| 2024/0254087 A1 | 8/2024 | Wallach et al. |
| 2024/0300885 A1 | 9/2024 | Short et al. |
| 2024/0366531 A1 | 11/2024 | Bowen et al. |
| 2024/0366542 A1 | 11/2024 | Khan et al. |

FOREIGN PATENT DOCUMENTS

| | | |
|---|---|---|
| WO | WO 9323364 A1 | 11/1993 |
| WO | WO-2019084338 A1 | 5/2019 |
| WO | WO-2019089066 A1 | 5/2019 |
| WO | WO 2020037372 A1 | 2/2020 |
| WO | WO-2021025723 A1 | 2/2021 |
| WO | WO-2022006186 A1 | 1/2022 |
| WO | WO-2022212854 A1 | 10/2022 |
| WO | WO-2022241006 A1 | 11/2022 |
| WO | WO 2022261240 A2 | 12/2022 |
| WO | WO-2022261263 A1 | 12/2022 |
| WO | WO-2023114320 A1 | 6/2023 |
| WO | WO-2023129909 A1 | 7/2023 |
| WO | WO-2024124056 A1 | 6/2024 |
| WO | WO-2024138032 A1 | 6/2024 |
| WO | WO-2024138041 A1 | 6/2024 |
| WO | WO-2024192150 A2 | 9/2024 |
| WO | WO-2024229149 | 11/2024 |

OTHER PUBLICATIONS

Baker et al., "Neurochemical and neuropharmacological investigation of Ncyanoethyltryptamine, a potential prodrug of tryptamine," Proc West Pharmacol Soc., 1987;30:307-11.
Benneyworth et al., "Complex discriminative stimulus properties of (+)lysergic acid diethylamide (LSD) in C57B1/6J mice," Psychopharmacology (2005) 179, 854-862.
Brandt et al., "Analytical characterization of bioactive N-benzyl-substituted phenethylamines and 5-methoxytryptamines", Rapid Communications Mass Spectrum, Apr. 15, 2015, 29(7): 573-584.
Carter et al., "Modulating the Rate and Rhythmicity of Perceptual Rivalry Alternations with the Mixed 5-HT2A and 5-HT1A Agonist Psilocybin," Neuropsychopharmacology (2005) 30, 1154-1162.
CAS Registry No. 1152718-19-8, Benzenemethanamine, N-[4-(1,1-dimethylethyl)cyclohexyl]-2,4-difluoro-a-methyl-, Jun. 5, 2009, 1 page.
CAS Registry No. 1152826-22-6, Benzenemethanamine, 5-bromo-N-[4-(1,1-dimethylpropyl)cyclohexyl]-2-fluoro-, Jun. 7, 2009, 1 page.
CAS Registry No. 1154138-59-6, Benzenemethanamine, N-[4-(1,1-dimethylpropyl)cyclohexyl]-2,5-difluoro-, Jun. 9, 2009, 1 page.
CAS Registry No. 127456-43-3, Phenol, 2-[[[4-(1,1-dimethylethyl)cyclohexyl]amino]methyl]-4-(1,1-dimethylpropyl)-, trans—(9C1), Jun. 1, 1990, 1 page.
CAS Registry No. 127456-44-4, 1H-Inden-5-ol, 6-[[[4-(1,1-dimethylethyl)cyclohexyl]amino]methyl]-2,3-dihydro-, trans—(9C1), Jun. 1, 1990, 1 page.
CAS Registry No. 127456-45-5, Phenol, 4-(1,1-dimethylethyl)-2-[[[4-(1,1-dimethylethyl)cyclohexyl]amino]methyl]-, trans—(9C1), Jun. 1, 1990, 1 page.
CAS Registry No. 127456-46-6, Phenol, 4-(1,1-dimethylethyl)-2-[[[4-(1,1-dimethylethyl)cyclohexyl]amino]methyl]-6-methyl-, hydrochloride, trans—(9C1), Jun. 1, 1990, 1 page.
CAS Registry No. 127456-52-4, Phenol, 2-[[[4-(1,1-dimethylethyl)cyclohexyl]amino]methyl]-4-(1-methylethyl)-, cis—(9C1), Jun. 1, 1990, 1 page.
CAS Registry No. 127456-56-8, Phenol, 4-chloro-2-[[[4-(1,1-dimethylethyl)cyclohexyl]amino]methyl]-, trans—(9C1), Jun. 1, 1990, 1 page.
CAS Registry No. 127456-57-9, Phenol, 2-[[[4-(1,1-dimethylethyl)cyclohexyl]amino]methyl]-4-fluoro-, trans—(9C1), Jun. 1, 1990, 1 page.
CAS Registry No. 1308467-14-2, 1,2-Benzenediol, 3-[[[4-(1,1-dimethylpropyl)cyclohexyl]amino]methyl]-, Jun. 10, 2011, 1 page.
CAS Registry No. 1405571-87-0, Benzenemethanamine, 2-bromo-N-[4-(1,1-dimethylpropyl)cyclohexyl]-5-fluoro-, Nov. 23, 2012, 1 page.
CAS Registry No. 1406541-63-6, Phenol, 2-chloro-4-[[[4-(1,1-dimethylpropyl)cyclohexyl]amino]methyl]-, Nov. 25, 2012, 1 page.
CAS Registry No. 1411655-23-6, Benzenemethanamine, N-[4-(1,1-dimethylpropyl)cyclohexyl]-2,3-difluoro-, Dec. 5, 2012, 1 page.
CAS Registry No. 1456349-79-3, Benzenemethanamine, 2,3-dichloro-N-[4-(1,1-dimethylpropyl)cyclohexyl]-, Oct. 6, 2013, 1 page.
CAS Registry No. 1458497-71-6, Benzenemethanamine, 2,4-dichloro-N-[4-(1,1-dimethylethyl)cyclohexyg-a-methyl-, Oct. 15, 2013, 1 page.

(56) References Cited

OTHER PUBLICATIONS

CAS Registry No. 1459328-13-2, Phenol, 2-bromo-4-[[[4-(1,1-dimethylpropyl)cyclohexyl]amino]methyl]-, Oct. 16, 2013, 1 page.
CAS Registry No. 1490220-45-5, Benzenemethanamine, 2-bromo-5-chloro-N-[4-(1,1-dimethylpropyl)cyclohexyl]-, Dec. 8, 2013, 1 page.
CAS Registry No. 1515984-46-9, Benzamide, N-(4-aminocyclohexyl)-3-chloro-N,5-dimethyl-, Jan. 10, 2014, 1 page.
CAS Registry No. 1542027-51-9, Phenol, 3-chloro-2-[[[4-(1,1-dimethylpropyl)cyclohexyl]amino]methyl]-, Feb. 11, 2014, 1 page.
CAS Registry No. 1624268-56-9, Benzamide, 4-[[[4-(1,1-dimethylethyl)cyclohexyl]amino]methyl]-N-methyl-, Sep. 22, 2014, 1 page.
CAS Registry No. 1712122-27-4, Benzenemethanamine, 5-chloro-N-[4-(1,1-dimethylpropyl)cyclohexyl]-2-fluoro-, May 25, 2015, 1 page.
CAS Registry No. 1772618-27-5, Phenol, 3-[[[4-(1,1-dimethylpropyl)cyclohexyl]amino]methyl]-5-fluoro-, Jun. 3, 2015, 1 page.
CAS Registry No. 1775706-37-0, Phenol, 2-chloro-6-[[[4-(1,1-dimethylpropyl)cyclohexyl]amino]methyl]-, Jun. 8, 2015, 1 page.
CAS Registry No. 1858436-76-6, Bicyclo[3.1.0]hexan-2-amine, N-[(3-chloro-5-methylphenyl)methyl]-, Feb. 3, 2016, 1 page.
CAS Registry No. 1931388-10-1, Benzenemethanamine, 2,5-dichloro-N-[4-(1,1-dimethylpropyl)cyclohexyl]-, Jun. 14, 2016, 1 page.
CAS Registry No. 1939264-55-7, Phenol, 4-[[[4-(1,1-dimethylpropyl)cyclohexyl]amino]methyl]-2-fluoro-, Jun. 26, 2016, 1 page.
CAS Registry No. 1939792-99-0, Benzenemethanamine, 5-bromo-2-chloro-N-[4-(1,1-dimethylpropyl)cyclohexyl]-, Jun. 27, 2016, 1 page.
CAS Registry No. 1962333-15-8, Benzenemethanamine, N-[4-(1,1-dimethylpropyl)cyclohexyl]-5-fluoro-2-methyl-, Jul. 29, 2016, 1 page.
CAS Registry No. 2032268-58-7, Cyclohexanecarboxylic acid, 4-[[(3-chloro-5-methylphenyl)methyl]amino]-, Nov. 15, 2016, 1 page.
CAS Registry No. 2199998-08-6, Cyclohexanecarboxylic acid, 2-[[(3-chloro-5-methylphenyl)methyl]amino]-1-methyl-, Mar. 27, 2018, 1 page.
CAS Registry No. 2202151-69-5, Cyclohexanecarboxylic acid, 3-[[(3-chloro-5-methylphenyl)methyl]amino]-, Mar. 30, 2018, 1 page.
CAS Registry No. 2322790-81-6, Benzenemethanamine, N-[4-(1,1-dimethylethyl)cyclohexyl]-3-(trifluoromethyl)-, Jun. 2, 2019, 1 page.
CAS Registry No. 2419600-39-6, Benzenemethanamine, 3-chloro-N-[4-(1,1-dimethylpropyl)cyclohexyl]-5-methyl-, Jun. 5, 2020, 1 page.
CAS Registry No. 415970-94-4, Benzenemethanamine, N-[4-(1,1-dimethylethyl)cyclohexyl]-3,5-dimethoxy-, May 15, 2002, 1 page.
CAS Registry No. 744981-83-7, Phenol, 2,6-dibromo-4-[[[4-(1,1-dimethylethyl)cyclohexyl]amino]methyl]-, Sep. 15, 2004, 1 page.
CAS Registry No. 793633-39-3, Phenol, 4-(1,1-dimethylethyl)-2-[[[trans-4-(1,1-dimethylethyl)cyclohexyl]amino]methyl]-6-methyl-, Dec. 6, 2004, 1 page.
Chen et al., Structure-activity relationships in a series of 5-[(2,5-dihydroxybenzyl)amino]salicylate inhibitors of EGF-receptor-associated tyrosine kinase: importance of additional hydrophobic aromatic interactions, Journal of Medicinal Chemistry, Mar. 18, 1994, pp. 845-859.
Cocchi et al., "Novel Psychoactive Phenethylamines: Impact on Genetic Material," International Journal of Molecular Sciences (2020), 21(24), 9616.
Demarinis et al., alpha.—Adrenergic agents. 2. Synthesis and. alpha. 1-agonist activity of 2-aminotetralins, Journal of Medicinal Chemistry, Feb. 1982, pp. 136-141.
Glennon et al., "Influence of Amine Substituents on 5-HT2A versus 5-HT2C Binding of Phenylalkyl- and Indolylalkylamines," Journal of Medicinal Chemistry (1994), 37(13), 1929-1935.

Gonzalez-Maeso et al., "Hallucinogens Recruit Specific Cortical 5-HT2A Receptor-Mediated Signaling Pathways to Affect Behavior," Neuron, Feb. 2007, 53, 439-452.
Halberstadt, "Recent Advances in the Neuropsychopharmacology of Serotonergic Hallucinogens," Behav. Brain Res. (2015) 277, 99-120 (60 pages).
Hamada et al., "Water-soluble prodrugs of dipeptide HIV protease inhibitors based on O—N intramolecular acyl migration: Design, synthesis and kinetic study," Bioorg Med Chem., Jan. 2, 2004;12(1):159-70.
Hansen et al., "Synthesis and pharmacological evaluation of N-benzyl substituted 4-bromo-2,5-dimethoxyphenethylamines as 5-HT2A/2C partial agonists," Bioorganic & Medicinal Chemistry (2015), 23(14), 3933-3937.
Hansen et al., "Synthesis and Structure-Activity Relationships of N-Benzyl Phenethylamines as 5-HT2A/2C Agonists," ACS Chemical Neuroscience (2014), 5(3), 243-249.
International Search Report and Written Opinion for International Application No. PCT/US2022/032715 dated Nov. 17, 2022, 18 pages.
International Search Report and Written Opinion for International Application No. PCT/US2022/032918, mailed Oct. 12, 2022, 10 pages.
International Search Report and Written Opinion for PCT/US2022/082403, May 17, 2023, 15 pages.
Invitation to Pay Fee for International Application No. PCT/US2022/082403 dated Mar. 8, 2023, 3 pages.
Kaminska et al., "25C-NBOMe short characterisation," Forensic Toxicology (2020) 38:490-495.
Kraehenmann et al., "Dreamlike effects of LSD on waking imagery in humans depend on serotonin 2A receptor activation," Psychopharmacology, 2017, 234: 2031-2046.
Kraehenmann et al., "LSD Increases Primary Process Thinking via Serotonin 2A Receptor Activation," Front. Pharmacol. (2017) 8:814, 9 pages.
Kucklander et al., "Darstellung and Oxidation von 2-(2,5-Dihydroxyphenyl)-ethylamin-Derivaten, II," Zeitschrift fuer Naturforschung, B: Chemical Sciences (1987), 42(12), 1567-77 (with English abstract).
Li et al., "Treatment of Breast and Lung Cancer Cells with a N-7 Benzyl Guanosine Monophosphate Tryptamine Phosphoramidate Pronucleotide (4Ei-1) Results in Chemosensitization to Gemcitabine and Induced eIF4E Proteasomal Degradation," Mol Pharm. Feb. 4, 2013; 10(2): 523-531, 19 pages.
Madsen et al., "Psychedelic effects of psilocybin correlate with serotonin 2A receptor occupancy and plasma psilocin levels," Neuropsychopharmacology (2019) 44: 1328-1334.
Miline et al., "Metabolic engineering of Saccharomyces cerevisiae for the de novo production of psilocybin and related tryptamine derivatives," Metabolic Engineering 60 (2020) 25-36.
Nichols et al., Nonneurotoxic tetralin and indan analogs of 3,4-(methylenedioxy) amphetamine (MDA), Journal of Medicinal Chemistry, Feb. 1990, pp. 703-710.
Nichols et al., Potential psychotomimetics. 2. Rigid analogs of 2,5-dimethoxy-4-methylphenylisopropylamine (DOM, STP), Journal of Medicinal Chemistry, Feb. 1974, pp. 161-166.
Nichols, "Hallucinogens," Pharmacol. Ther. (2004) 101, 131-181.
Nichols, "Structure-Activity Relationships of Phenethylamine Hallucinogens," J. Pharm. Sciences, 1981, 70(8), 839-849.
Perez Custodio et al., "25B-NBOMe, a novel N-2-methoxybenzyl-phenethylamine (NBOMe) derivative, may induce rewarding and reinforcing effects via a dopaminergic mechanism: Evidence of abuse potential," Addiction Biology 2019;e12850, 12 pages.
Pokorny et al., "Modulatory effect of the 5-HT1A agonist buspirone and the mixed non-hallucinogenic 5-HT1A/2A agonist ergotamine on psilocybin-induced psychedelic experience," Eur. Neuropsychopharmacol. (2016) 26, 756-766.
Pottie et al., "Identification of psychedelic new psychoactive substances (NPS) showing biased agonism at the 5-HT2AR through simultaneous use of 13-arrestin 2 and miniGαq bioassays," Biochemical Pharmacology, 2020, 182, 114251 (Peer reviewed author version, 38 pages).

(56) References Cited

OTHER PUBLICATIONS

Preller et al., "Effects of serotonin 2A/1A receptor stimulation on social exclusion processing," PNAS, May 3, 2016, vol. 113, No. 18, 5119-5124.
Preller et al., "Role of the 5-HT2A Receptor in Self- and Other-Initiated Social Interaction in Lysergic Acid Diethylamide-Induced States: A Pharmacological fMRI Study," J. Neurosci., Apr. 2018, 38(14):3603-3611.
Preller et al., "The Fabric of Meaning and Subjective Effects in LSD-Induced States Depend on Serotonin 2A Receptor Activation," Current Biology, Feb. 2017, 27, 451-457.
PubChem SID 310331158, Feb. 15, 2016, 4 pages, retrieved from https://pubchem.ncbi.nlm.nih.gov/substance/310331158.
PubChem SID 369863280, May 25, 2018, 5 pages, retrieved from https://pubchem.ncbi.nlm.nih.gov/substance/369863280.
PubChem SID 385740476, 2-(2,5-dimethoxy-4-(propan-2-yt)phenyl)-N-(2methoxybenzyl)ethanamine, Sep. 23, 2019, 6 pages, retrieved from https://pubchem.ncbi.nlm.nih.gov/substance/385740476.
PubChem, SID 103414083, Date of Deposit: Dec. 22, 2010, 7 pages.
PubChem, SID 103936367, Date of Deposit: Jan. 1, 2011, 6 pages.
Sargent et al., "Radiohalogen-Labeled Imaging Agents. 3. Compounds for Measurement of Brain Blood Flow by Emission Tomography," Journal of Medicinal Chemistry (1984), 27(8), 1071-1077.
Schifano et al., "New psychoactive substances (NPS) and serotonin syndrome onset: A systematic review," Experimental Neurology (2021), 339, 113638 (Author manuscript, 29 pages).
Tirapegui et al., "Synthesis of N-(halogenated) benzyl analogs of superpotent serotonin ligands," J. Chil. Chem. Soc., (2014) 59, No. 3, pp. 2625-2627.
Titeler et al., "Radioligand binding evidence implicates the brain 5-HT2 receptor as a site of action for LSD and phenylisopropylamine hallucinogens," Psychopharmacology (1988) 94, 213-216.
Tomaszewski et al., "Benzofuran Bioisosteres of Hallucinogenic Tryptamines," J. Med. Chem., 1992, 35, pp. 2061-2064.
Valle et al., "Inhibition of alpha oscillations through serotonin-2A receptor activation underlies the visual effects of ayahuasca in humans," Eur. Neuropsychopharm (2016) 26, 1161-1175 (Author-edited version, 23 pages).
Vollenweider et al., "Psilocybin induces schizophrenia-like psychosis in humans via a serotonin-2 agonist action," Neuroreport (1998) 9, 3897-3902 (8 pages).
Vollenweider et al., "Psychedelic drugs: neurobiology and potential for treatment of psychiatric disorders," Nature Reviews Neuroscience, Nov. 2020, vol. 21, pp. 611-624.
Winter et al., "Psilocybin-induced stimulus control in the rat," Pharmacol. Biochem. Behay. (2007) 87, 472-480 (18 pages).
Wood et al., "Prevalence of use and acute toxicity associated with the use of NBOMe drugs," Clinical Toxicology, 2015, 53:85-92.
Berge et al., "Pharmaceutical Salts," J. Pharmaceutical Sciences, 66(1), pp. 1-19 (Jan. 1977).
International Search Report and Written Opinion for International Application No. PCT/US2023/085505, mailed Apr. 8, 2024, 11 pages.
International Search Report and Written Opinion for International Application No. PCT/US2023/085521, mailed Apr. 8, 2024, 13 pages.
International Search Report and Written Opinion for International Application No. PCT/US2024/019770, mailed Aug. 12, 2024. 22 pages.
International Search Report and Written Opinion for International Application No. PCT/US23/82981, mailed Apr. 4, 2024. 24 pages.
International Search Report and Written Opinion for PCT Application No. PCT/US2024/027296 mailed Aug. 13, 2024, 18 pages.
Invitation to Pay Fee for International Application No. PCT/US2022/032715 dated Aug. 30, 2022, 2 pages.
Kehne et al, "Preclinical characterization of the potential of the putative atypical antipsychotic MDL 100,907 as a potent 5-HT2A antagonist with a favorable CNS safety profile." J Pharmacol Exp Ther. May 1996; 277(2): 968-81.
Kennett et al. "SB 242084, a selective and brain penetrant 5-HT2C receptor antagonist", Neuropharmacology, (1997); 36(4-5): 609-620.
Klein et al., "Investigation of the Structure-Activity Relationships of Psilocybin Analogues." ACS Pharmacol. Transl. Sci. 2021, 4, 533-542.
National Center for Biotechnology Information "2-(2,5-Dimethoxy-4-methylsulfanyl-phenyl)-N-[(2-methoxyphenyl)methyl]ethanamine: Pubchem CID 124518722" Pubchem entry (online), Apr. 10, 2017; Retrieved on Feb. 17, 2024 from the Internet: [URL:https://pubchem.ncbi.nlm.nih.gov/compound/124518722]; 13 pages.
National Center for Biotechnology Information 2-[2,5-dimethoxy-4-(methylsulfonimidoyl)phenyl]-N-[(3-fluoro-5-methylphenyl)methyl]ethanamine: Pubchem CID 167226743 Pubchem entry (online), pp. 1-9, Mar. 21, 2023, URL:https://pubchem.ncbi.nlm.nih.gov/compound/167226743.
National Center for Biotechnology Information, "2-(2,5-dimethoxyphenyl)-N-(pyridin-2-ylmethyl)ethanamine: Pubchem CID 39371636" Pubchem entry (online), created May 29, 2009, Modified Oct. 12, 2024, [URL: https://pubchem.ncbi.nlm.nih.gov/compound/39371636]; 7 pages.
National Center for Biotechnology Information "N-[(3-chloro-5-methylphenyl)methyl]-2-[2,5-dimethoxy-4-(methylsulfonimidoyl)phenyl]ethanamine Pubchem CID 167226858" Pubchem entry (online), pp. 1-8, Mar. 21, 2023, URL: https://pubchem.ncbi.nlm.nih.gov/compound/167226858.
National Center for Biotechnology Information "N-benzyl-2,5-dimethoxy-phenethylamine: Pubchem CID 13836160" PubChem entry (online), pp. 1-9, Feb. 8, 2007; URL: https://pubchem.ncbi.nlm.nih.gov/compound/13836160. 9 pages.
Poulie et al., "Discovery of β-Arrestin-Biased 25CN-NBOH-Derived 5-HT2A Receptor Agonists." J Med Chem. Sep. 22, 2022; 65(18): 12031-12043. doi:10.1021/acs.jmedchem.2c00702. Epub Sep. 13, 2022.
Pubchem SID 387777206, Modify Date: Dec. 6, 2019 Retrieved from the Internet URL: https://pubchem.ncbi.nlm.nih.gov/ substance/387777206, 5 pages.
Pubchem, SID 472180752, Modify Date: Oct. 11, 2022 [retrieved on Feb. 21, 2024]. Retrieved from the Internet URL: https://pubchem.ncbi.nlm.nih.gov/ substance/472180752, 5 pages.
Braden M.R., et al., "Molecular Interaction of Serotonin 5-HT2A Receptor Residues Phe339(6.51) and Phe340(6.52) with Superpotent N-Benzyl Phenethylamine Agonists." Molecular Pharmacology, American Society for Pharmacology and Experimental Therapeutics, US, vol. 70, No. 6, Dec. 1, 2006 (Dec. 1, 2006), pp. 1956-1965.
Jensen A.A., et al., "Detailed Characterization of the In Vitro Pharmacological and Pharmacokinetic Properties of N-(2-Hydroxybenzyl)-2,5-Dimethoxy-4-Cyanophenylethylamine (25CN-NBOH), a Highly Selective and Brain-Penetrant 5- HT2A Receptor Agonist." J Pharmacol Exp Ther. Jun. 2017; 361(3): 441-453. doi: 10.1124/jpet.117.239905. Epub Mar. 30, 2017.
Leth-Petersen S., et al., "Correlating the Metabolic Stability of Psychedelic 5- HT2A Agonists with Anecdotal Reports of Human Oral Bioavailability." Neurochem Res. Oct. 2014; 39(10): 2018-23. doi: 10.1007/s11064-014-1253-y. Epub Feb. 12, 2014.

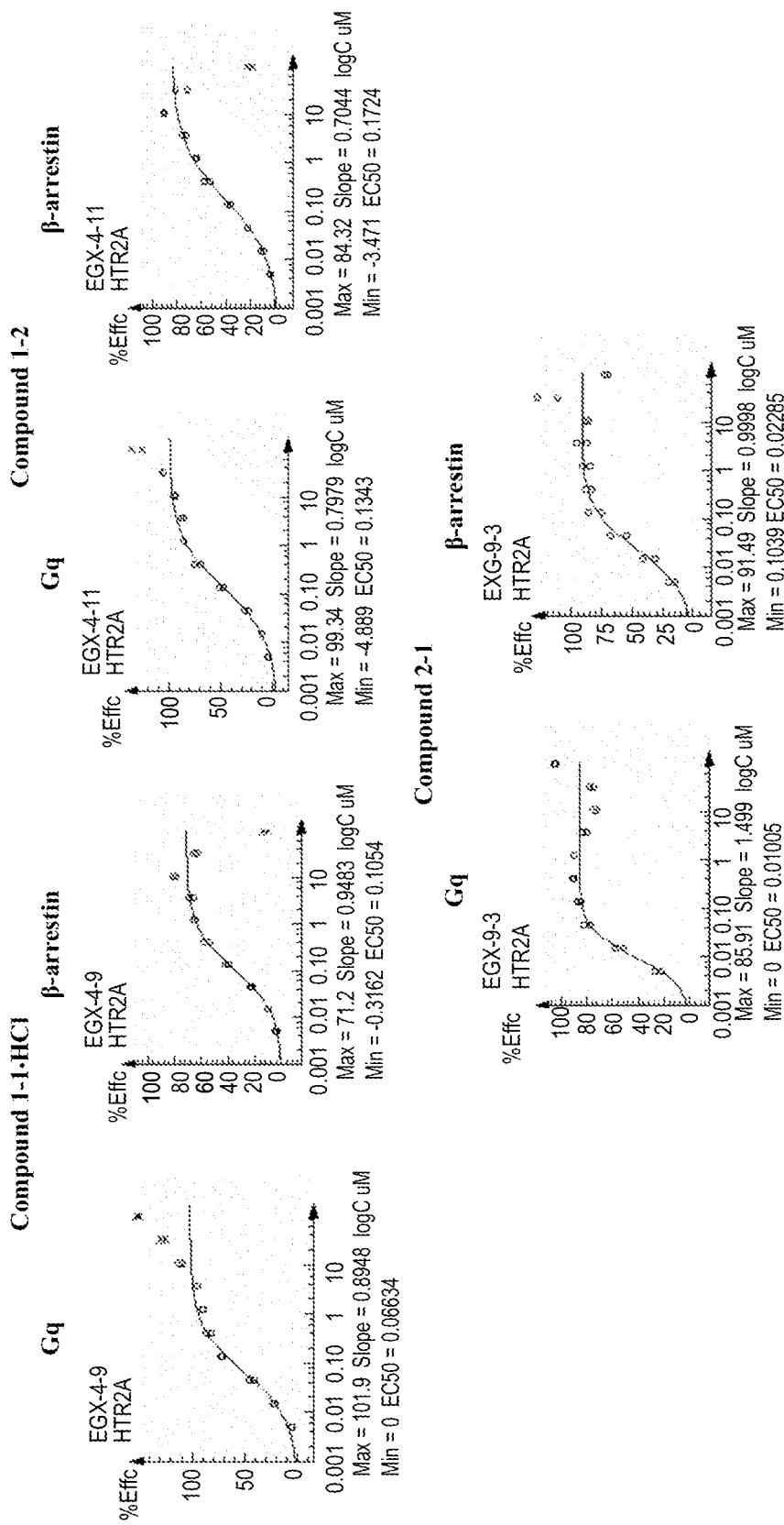

DIMETHOXYPHENYLALKYLAMINE ACTIVATORS OF SEROTONIN RECEPTORS

CROSS-REFERENCE TO RELATED APPLICATIONS

The present application is a continuation of U.S. patent application Ser. No. 17/835,764 filed Jun. 8, 2022, which claims priority to U.S. Provisional Patent Application No. 63/208,391 filed Jun. 8, 2021, and U.S. Provisional Application No. 63/241,662 filed Sep. 8, 2021, and which are hereby incorporated by reference in their entirety.

BACKGROUND OF THE INVENTION

Psychedelics can be classified into three main classes: indoleamines, phenylalkylamines, and ergolines. The first class, indolamines includes N,N-dimethyltryptamine (DMT), 5-methoxy-DMT (5-MeO-DMT), psilocybin and 4-hydroxy-DMT. The second class, phenylalkylamines, includes mescaline, as well as synthetic mescaline analogs such as 2,5-dimethoxy-4-iodoamphetamine (DOI) and 2,5-dimethoxy-4-bromoamphetamine (DOB). The third class are ergolines, such as LSD. The phenylalkylamines are selective agonists of 5-HT2 receptors, including 5-HT2A, 5-HT2B and 5-HT2C receptors. The indoleamines and ergolines act as partial agonists of 5-HT1, 5-HT2, 5-HT6 and 5-HT7 receptors. LSD and other ergolines also act upon D1 and D2 dopamine receptors and adrenergic receptors.

Activation of 5-HT2A receptors located in cortical and subcortical structures of the brain are thought to mediate the subjective, behavioral and psychological effects of psychedelics in both animals and humans. Serotonergic psychedelics have demonstrated potential for treating a range of mental health diseases or disorders.

There remains a need for compounds that act as agonists of serotonin receptors, such as the 5-HT2A receptor as well as compositions and methods of use thereof.

SUMMARY OF THE INVENTION

In one aspect, the present disclosure provides compounds which act as agonists of serotonin receptors e.g., the 5-HT2A receptor, as well as compositions and methods of use thereof e.g., for the treatment of a mental health disease or disorder.

In some embodiments, the present disclosure provides a compound of Formula (I):

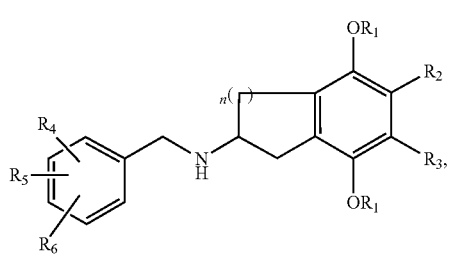

or a pharmaceutically acceptable salt thereof, wherein, $R_1$ is independently at each position hydrogen, $C_1$-$C_6$ alkyl or $C_1$-$C_6$ haloalkyl;

$R_2$ and $R_3$ are independently hydrogen, $C_1$-$C_6$ alkyl, $C_1$-$C_6$ haloalkyl, halogen, cyano, $OR_1$ or $SR_1$, wherein at least one of $R_2$ and $R_3$ is hydrogen;

$R_4$, $R_5$ and $R_6$ are independently hydrogen, $C_1$-$C_6$ alkyl, $C_1$-$C_6$ haloalkyl, halogen, cyano, $OR_1$, $SR_1$, $O(C=O)(R_{12})$, or $NH(C=O)(R_{12})$, wherein $R_{12}$ is $C_1$-$C_6$ alkyl; and n is an integer from 0-3.

In some embodiments, the present disclosure provides a compound of Formula (I-A):

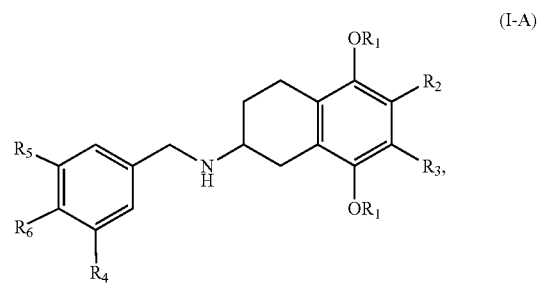

or a pharmaceutically acceptable salt thereof, wherein: $R_1$, $R_2$, $R_3$ $R_4$, $R_5$ and $R_6$ are defined herein.

In some embodiments, the present disclosure provides a compound of Formula (II):

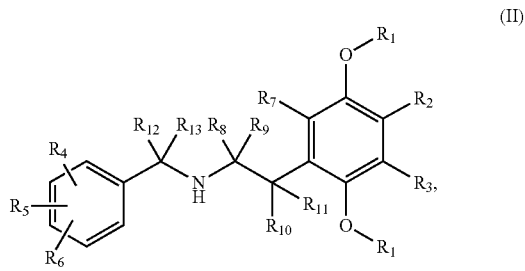

or a pharmaceutically acceptable salt thereof, wherein, $R_1$ is independently at each position hydrogen, $C_1$-$C_6$ alkyl, or $C_1$-$C_6$ haloalkyl;

$R_2$, $R_3$ and $R_7$ are independently hydrogen, heterocycle, $C_1$-$C_6$ alkyl, $C_1$-$C_6$ haloalkyl, halogen, cyano, $OR_1$, $S(O)(=NH)R_1$, $S(O)_2R_1$, $S(O)R_1$ or $SR_1$, wherein at least one of $R_2$ and $R_3$ is hydrogen;

$R_4$, $R_5$ and $R_6$ are independently hydrogen, $C_1$-$C_6$ alkyl, $C_1$-$C_6$ haloalkyl, halogen, cyano, $OR_1$, $SR_1$, $(C=O)(R_{14})$, $O(C=O)(R_{14})$, $NO_2$, or $NH(C=O)(R_{14})$, wherein $R_{14}$ is $C_1$-$C_6$ alkyl, OH, or $OC_1$-$C_6$ alkyl;

$R_8$ and $R_9$ are independently hydrogen, $C_1$-$C_6$ alkyl, $C_1$-$C_4$ alkyl, $C_3$-$C_6$ cycloalkyl, $C_3$-$C_{10}$ cycloalkyl, $CH_2OH$, or $CH_2O$—$C_1$-$C_4$ alkyl; and $R_{10}$ and $R_{11}$ are independently hydrogen, halogen, $C_1$-$C_6$ alkyl, OH, $C_1$-$C_4$ alkyl, $C_3$-$C_6$ cycloalkyl, or $CH_2O$—$C_1$-$C_4$ alkyl;

$R_{12}$ is hydrogen, $CH_2OH$, $CH_2O$—$C_1$-$C_9$ alkyl, $C_3$-$C_{10}$ cycloalkyl, $CH_2OH$, or $CH_2O$—$C_1$-$C_4$ alkyl;

$R_{13}$ is hydrogen, $C_1$-$C_9$ alkyl, $C_3$-$C_{10}$ cycloalkyl, or $CH_2OH$, $CH_2O$—$C_1$-$C_4$ alkyl;

In some embodiments, the present disclosure provides a compound of Formula (II-A):

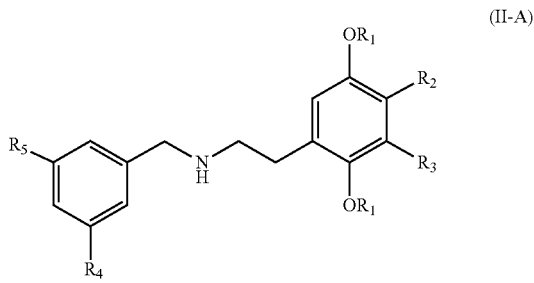

(II-A)

or a pharmaceutically acceptable salt thereof, wherein:
$R_1$, $R_2$, $R_3$ $R_4$, and $R_5$ are defined herein.

In some embodiments, the present disclosure provides a pharmaceutical composition comprising a compound of Formula (I), or Formula (II), or a pharmaceutically acceptable salt thereof and a pharmaceutically acceptable excipient.

In some embodiments, the present disclosure provides a method of treating a mental health disease or disorder in a subject in need thereof, the method comprising administering to the subject a therapeutically effective amount of a compound of Formula (I), or Formula (II), or a pharmaceutically acceptable salt thereof.

BRIEF DESCRIPTION OF THE FIGURES

FIG. 1 depicts EC50 profiles of Compounds 1-1, 1-2, and 2-1 comparing 5-HT2A Gq and β-arrestin biased signaling.

DETAILED DESCRIPTION

Throughout this disclosure, various patents, patent applications and publications are referenced. The disclosures of these patents, patent applications and publications in their entireties are incorporated into this disclosure by reference for all purposes in order to more fully describe the state of the art as known to those skilled therein as of the date of this disclosure. This disclosure will govern in the instance that there is any inconsistency between the patents, patent applications and publications cited and this disclosure.

Definitions

For convenience, certain terms employed in the specification, examples and claims are collected here. Unless defined otherwise, all technical and scientific terms used in this disclosure have the same meanings as commonly understood by one of ordinary skill in the art to which this disclosure belongs.

The term "about" when immediately preceding a numerical value means a range (e.g., plus or minus 10% of that value). For example, "about 50" can mean 45 to 55, "about 25,000" can mean 22,500 to 27,500, etc., unless the context of the disclosure indicates otherwise, or is inconsistent with such an interpretation. For example in a list of numerical values such as "about 49, about 50, about 55, . . . ", "about 50" means a range extending to less than half the interval(s) between the preceding and subsequent values, e.g., more than 49.5 to less than 50.5. Furthermore, the phrases "less than about" a value or "greater than about" a value should be understood in view of the definition of the term "about" provided herein. Similarly, the term "about" when preceding a series of numerical values or a range of values (e.g., "about 10, 20, 30" or "about 10-30") refers, respectively to all values in the series, or the endpoints of the range.

The terms "administer," "administering" or "administration" as used herein refer to administering a compound or pharmaceutically acceptable salt of the compound or a composition or formulation comprising the compound or pharmaceutically acceptable salt of the compound to a patient.

The term "treating" as used herein with regard to a patient or subject, refers to improving at least one symptom of the patient's or subject's disorder. In some embodiments, treating can be improving, or at least partially ameliorating a disorder or one or more symptoms of a disorder.

The term "therapeutically effective" applied to dose or amount refers to that quantity of a compound or pharmaceutical formulation that is sufficient to result in a desired clinical benefit after administration to a patient or subject in need thereof.

The term "pharmaceutically acceptable salts" includes both acid and base addition salts. Pharmaceutically acceptable salts include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. The acids that may be used to prepare pharmaceutically acceptable acid addition salts of such basic compounds are those that form non-toxic acid addition salts, i.e., salts containing pharmaceutically acceptable anions, including but not limited to malate, oxalate, chloride, bromide, iodide, nitrate, acetate, tartrate, oleate, fumarate, formate, benzoate, glutamate, methanesulfonate, benzenesulfonate, and p-toluenesulfonate salts. Base addition salts include but are not limited to, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris-(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e. g., lysine and arginine dicyclohexylamine and the like. Examples of metal salts include lithium, sodium, potassium, magnesium, calcium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like. Those skilled in the art will further recognize that acid addition salts may be prepared by reaction of the compounds with the appropriate inorganic or organic acid via any of a number of known methods.

When a range of values is listed, it is intended to encompass each value and sub-range within the range. For example, "$C_1$-$C_6$ alkyl" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" or "alkyl group" refers to a fully saturated, straight or branched hydrocarbon chain having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Cycloalkyl" refers to a stable non-aromatic monocyclic or polycyclic fully saturated hydrocarbon consisting solely of carbon and hydrogen atoms, which can include fused, bridged, or spirocyclic ring systems, having from three to twenty carbon atoms (e.g., having from three to ten carbon atoms) and which is attached to the rest of the molecule by a single bond. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, 7,7-dimethyl-bicyclo[2.2.1]heptanyl, and the like. Unless otherwise stated specifically in the specification, a cycloalkyl group can be optionally substituted.

"Haloalkyl" refers to an alkyl, as defined above, that is substituted by one or more halo radicals, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group can be optionally substituted.

"Heterocyclyl," "heterocyclic ring" or "heterocycle" refers to a stable saturated, unsaturated, or aromatic 3- to 20-membered ring which consists of two to nineteen carbon atoms and from one to six heteroatoms selected from the group consisting of nitrogen, oxygen and sulfur, and which is attached to the rest of the molecule by a single bond. Heterocyclyl or heterocyclic rings include heteroaryls, heterocyclylalkyls, heterocyclylalkenyls, and hetercyclylalkynyls. Unless otherwise specifically in the specification, the heterocyclyl can be a monocyclic, bicyclic, tricyclic or tetracyclic ring system, which can include fused, bridged, or spirocyclic ring systems; and the nitrogen, carbon or sulfur atoms in the heterocyclyl can be optionally oxidized; the nitrogen atom can be optionally quaternized; and the heterocyclyl can be partially or fully saturated. Examples of such heterocyclyl include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group can be optionally substituted.

"The term "substituted" used herein means any of the groups described herein (e.g., alkyl, alkenyl, alkynyl, alkoxy, aryl, cycloalkyl, cycloalkenyl, cycloalkynyl, haloalkyl, heterocyclyl, and/or heteroaryl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)$ORh, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$C(=O)$ $NR_gR_h$, —$CH_2SO_2R_g$, —$CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

Compounds

In one aspect, the present disclosure provides compounds which act as agonists of the 5-HT2A receptor. In some embodiments, the compounds are full agonists of the 5-HT2A receptor. In some embodiments, the compounds are partial agonists of the 5-HT2A receptor. In some embodiments, the compounds display selectivity for 5-HT2A receptor.

Activation of 5-HT2A receptors located in cortical and subcortical structures of the brain are thought to mediate the subjective, behavioral and psychological effects of psychedelics in both animals and humans. In rodents, psychedelics have shown to elicit a 'head twitch response' which has been demonstrated to be a direct and selective consequence of 5-HT2A activation over other similar serotonin receptors including both 5-HT2C and 5-HT2B (Halberstadt, A. L., Behav. Brain Res. 277, 99-120 (2015); Winter et al., Pharmacol. Biochem. Behav. 87, 472-480 (2007); Benneyworth et al., Psychopharmacology 179, 854-862 (2005); Titeler et al, Psychopharmacology, 94, 213-216 (1988)). Similar observations have been made in humans where the administration of ketanserin, a 5-HT2A receptor antagonist, blocked the majority of subjective effects induced by DMT, psilocyin and LSD (Preller, Curr. Biol. 27, 451-457 (2017); Preller, J. Neurosci. 38, 3603-3611 (2018); Kraehenmann, Front. Pharmacol. 8, 814 (2017); Kraehenmann, Psychopharmacology 234, 2031-2046 (2017); Vollenweider, Neuroreport 9, 3897-3902 (1998); Preller, Acad. Sci. USA 11 3, 5119-5124 (2016); Valle, Eur. Neuropsychopharm 26, 1161-1175 (2016)). In addition, psychedelic effects elicited by psilocybin have correlated with 5-HT2A receptor occupancy as measured by positron emission tomography in the prefrontal cortex (PFC) and other cortical regions in humans (Madsen, Neuropsychopharmacology 44, 1328-1334 (2019)). While 5-HT2A is the predominant driver of psychedelic effects in humans, other serotonin receptors, like 5-HT1A, are likely contributing to the overall psychedelic experience including both visual and attention-disrupting effects in humans (Pokorny et al., Eur. Neuropsychopharmacol. 26, 756-766 (2016); Carter et al., Neuropsychopharmacology 30, 1154-1162 (2005)).

Biased signaling consequences of 5-HT2A activation by various agonists strongly impact whether or not a compound will be hallucinogenic or non-hallucinogenic. For example, LSD and lisuride both activate the 5-HT2A receptor but in slightly different ways which result in the activation of different intracellular signaling cascades. LSD and lisuride have been shown to active canonical Gq-based signaling downstream of 5-HT2A, but only LSD stimulated the expression of early growth response proteins (EGR1 and EGR2) by activating Gi/o subunits and the SRC protein kinase (Gonzalez-Maeso et al, Neuron 53, 439-452 (2007)). Differential functional selectivity has been shown for several phenalkylamine pyschedelics which were found to be biased 5-HT2A agonists (Pottie et al, Biochemical pharmacology, 182, 114251, 2020). The compounds, including 25H—NBF, 25H—NBMD, 25H—NBOH and 25H—NBOMe showed a statistically significant preference towards the recruitment of β-arrestin 2 over miniGaq, as compared to the reference psychedelic substance LSD.

Differential biased agonism elicited across multiple classes of psychedelics warrants further investigation to identify whether this functional selectivity may provide compounds with greater selectivity, fewer side effects, greater neuroplastic effects and improved therapeutic benefit.

In some embodiments, the present disclosure provides a compound of Formula (I):

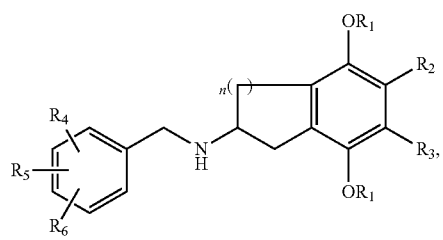

(I)

or a pharmaceutically acceptable salt thereof, wherein,
$R_1$ is independently at each position hydrogen, $C_1$-$C_6$ alkyl, or $C_1$-$C_6$ haloalkyl;
$R_2$ and $R_3$ are independently hydrogen, $C_1$-$C_6$ alkyl, $C_1$-$C_6$ haloalkyl, halogen, cyano, $OR_1$ or $SR_1$, wherein at least one of $R_2$ and $R_3$ is hydrogen;

$R_4$, $R_5$ and $R_6$ are independently hydrogen, $C_1$-$C_6$ alkyl, $C_1$-$C_6$ haloalkyl, halogen, cyano, $OR_1$, $SR_1$, $O(C=O)(R_{12})$, or $NH(C=O)(R_{12})$, wherein $R_{12}$ is $C_1$-$C_6$ alkyl; and
n is an integer from 0-3.

In some embodiments, the compound of Formula (I) is a compound of Formula (I-A)

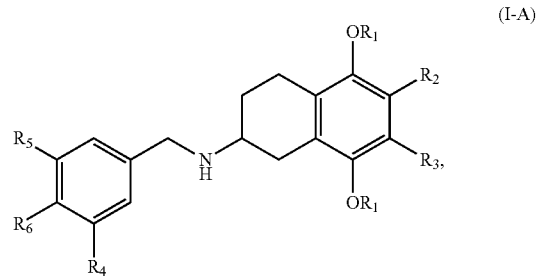

(I-A)

or a pharmaceutically acceptable salt thereof, wherein, $R_1$, $R_2$, $R_3$ $R_4$, $R_5$ and $R_6$ are defined herein.

In some embodiments of the compounds of Formula (I) or (I-A), $R_1$ is independently at each position hydrogen, $C_1$-$C_6$ alkyl, or $C_1$-$C_6$ haloalkyl.

In some embodiments of the compounds of Formula (I) or (I-A), $R_1$ is independently at each position hydrogen or $C_1$-$C_6$ alkyl.

In some embodiments of the compounds of Formula (I) or (I-A), $R_1$ is independently at each position $C_1$-$C_6$ alkyl.

In some embodiments of the compounds of Formula (I) or (I-A), $R_1$ is independently at each position $C_1$-$C_6$ haloalkyl. In some embodiments, $R_1$ is independently at each position $C_1$-$C_3$ haloalkyl. In some embodiments, $R_1$ is independently at each position $CF_3$.

In some embodiments of the compounds of Formula (I) or (I-A), $R_1$ is independently at each position $C_1$-$C_3$ alkyl.

In some embodiments of the compounds of Formula (I) or (I-A), $R_1$ is independently at each position methyl, ethyl, propyl, or isopropyl.

In some embodiments of the compounds of Formula (I) or (I-A), $R_1$ is methyl.

In some embodiments of the compounds of Formula (I) or (I-A), $R_2$ and $R_3$ are independently hydrogen, $C_1$-$C_6$ alkyl, $C_1$-$C_6$ haloalkyl, halogen, cyano, $OR_1$ or $SR_1$, wherein at least one of $R_2$ and $R_3$ is hydrogen.

In some embodiments of the compounds of Formula (I) or (I-A), $R_2$ and $R_3$ are independently hydrogen, $C_1$-$C_6$ alkyl, halogen, cyano, $OR_1$ or $SR_1$, wherein at least one of $R_2$ and $R_3$ is hydrogen.

In some embodiments of the compounds of Formula (I) or (I-A), $R_2$ and $R_3$ are independently hydrogen, halogen. $C_1$-$C_6$ alkyl, or $C_1$-$C_6$ haloalkyl, wherein at least one of $R_2$ and $R_3$ is hydrogen.

In some embodiments of the compounds of Formula (I) or (I-A), $R_2$ and $R_3$ are independently hydrogen, halogen, $C_1$-$C_3$ alkyl, or $C_1$-$C_3$ haloalkyl, wherein at least one of $R_2$ and $R_3$ is hydrogen.

In some embodiments of the compounds of Formula (I) or (I-A), $R_2$ and $R_3$ are independently hydrogen, $C_1$-$C_6$ alkyl, or $C_1$-$C_6$ haloalkyl, wherein at least one of $R_2$ and $R_3$ is hydrogen.

In some embodiments of the compounds of Formula (I) or (I-A), $R_2$ and $R_3$ are independently hydrogen, $C_1$-$C_3$ alkyl, or $C_1$-$C_3$ haloalkyl, wherein at least one of $R_2$ and $R_3$ is hydrogen.

In some embodiments of the compounds of Formula (I) or (I-A), $R_2$ and $R_3$ are independently hydrogen, or $C_1$-$C_6$ alkyl, wherein at least one of $R_2$ and $R_3$ is hydrogen.

In some embodiments of the compounds of Formula (I) or (I-A), $R_2$ and $R_3$ are independently hydrogen, or $C_1$-$C_3$ alkyl, wherein at least one of $R_2$ and $R_3$ is hydrogen.

In some embodiments of the compounds of Formula (I) or (I-A), $R_2$ and $R_3$ are independently hydrogen, —$CF_3$, methyl or ethyl, wherein at least one of $R_2$ and $R_3$ is hydrogen.

In some embodiments of the compounds of Formula (I) or (I-A), $R_2$ and $R_3$ are independently hydrogen, methyl or ethyl, wherein at least one of $R_2$ and $R_3$ is hydrogen.

In some embodiments of the compounds of Formula (I) or (I-A), $R_2$ and $R_3$ are independently hydrogen or methyl, wherein at least one of $R_2$ and $R_3$ is hydrogen.

In some embodiments of the compounds of Formula (I) or (I-A), $R_2$ is hydrogen, —$CF_3$, methyl or ethyl and $R_3$ is hydrogen.

In some embodiments of the compounds of Formula (I) or (I-A), $R_2$ is hydrogen, methyl or ethyl and $R_3$ is hydrogen.

In some embodiments of the compounds of Formula (I) or (I-A), $R_3$ is hydrogen.

In some embodiments of the compounds of Formula (I) or (I-A), $R_2$ is hydrogen.

In some embodiments of the compounds of Formula (I) or (I-A), $R_2$ is hydrogen and $R_3$ is hydrogen, —$CF_3$, methyl or ethyl.

In some embodiments of the compounds of Formula (I) or (I-A), $R_2$ is hydrogen and $R_3$ is hydrogen, methyl or ethyl.

In some embodiments of the compounds of Formula (I) or (I-A), $R_2$ and $R_3$ are hydrogen.

In some embodiments of the compounds of Formula (I) or (I-A), $R_2$ is halogen and $R_3$ is hydrogen.

In some embodiments of the compounds of Formula (I) or (I-A), $R_2$ is iodo and $R_3$ is hydrogen.

In some embodiments of the compounds of Formula (I) or (I-A), $R_2$ is hydrogen and $R_3$ is halogen.

In some embodiments of the compounds of Formula (I) or (I-A), $R_2$ is hydrogen and $R_3$ is iodo.

In some embodiments of the compounds of Formula (I) or (I-A), $R_4$, $R_5$ and $R_6$ are independently hydrogen, $C_1$-$C_6$ alkyl, $C_1$-$C_6$ haloalkyl, halogen, cyano, $OR_1$, $SR_1$, $O(C=O)(R_{12})$, or $NH(C=O)(R_{12})$, wherein $R_{12}$ is $C_1$-$C_6$ alkyl.

In some embodiments of the compounds of Formula (I) or (I-A), $R_4$, $R_5$ and $R_6$ are independently hydrogen, $C_1$-$C_6$ alkyl, halogen, cyano, $OR_1$, $SR_1$, $O(C=O)(R_{12})$, or $NH(C=O)(R_{12})$, wherein $R_{12}$ is $C_1$-$C_6$ alkyl.

In some embodiments of the compounds of Formula (I) or (I-A), $R_4$ is $C_1$-$C_6$alkyl or $C_1$-$C_6$haloalkyl.

In some embodiments of the compounds of Formula (I) or (I-A), $R_4$ is $C_1$-$C_6$alkyl.

In some embodiments of the compounds of Formula (I) or (I-A), $R_4$ is —$CF_3$ or methyl.

In some embodiments of the compounds of Formula (I) or (I-A), $R_4$ is methyl.

In some embodiments of the compounds of Formula (I) or (I-A), $R_5$ is halogen.

In some embodiments of the compounds of Formula (I) or (I-A), $R_5$ is chloro.

In some embodiments of the compounds of Formula (I) or (I-A), $R_6$ is hydrogen.

In some embodiments of the compounds of Formula (I), n is an integer from 0-3 (i.e. 0, 1, 2, or 3). In some embodiments, n is 1 or 2. In some embodiments, n is 0. In some embodiments n is 1. In some embodiments n is 2. In some embodiments n is 3.

In one aspect, provided herein is a compound of Formula (II):

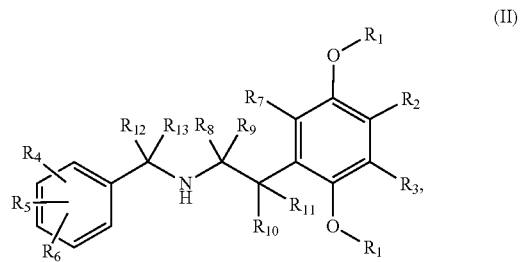

or a pharmaceutically acceptable salt thereof, wherein,
$R_1$ is independently at each position hydrogen, $C_1$-$C_6$ alkyl, or $C_1$-$C_6$ haloalkyl;
$R_2$, $R_3$ and $R_7$ are independently hydrogen, heterocycle, $C_1$-$C_6$ alkyl, $C_1$-$C_6$ haloalkyl, halogen, cyano, $OR_1$, $S(O)(=NH)R_1$, $S(O)_2R_1$, $S(O)R_1$ or $SR_1$, wherein at least one of $R_2$ and $R_3$ is hydrogen;
$R_4$, $R_5$ and $R_6$ are independently hydrogen, $C_1$-$C_6$ alkyl, $C_1$-$C_6$ haloalkyl, halogen, cyano, $OR_1$, $SR_1$, $(C=O)(R_{14})$, $O(C=O)(R_{14})$, $NO_2$, or $NH(C=O)(R_{14})$, wherein $R_{14}$ is $C_1$-$C_6$ alkyl, OH, or $OC_1$-$C_6$ alkyl;
$R_8$ and $R_9$ are independently hydrogen, $C_1$-$C_6$ alkyl, $C_1$-$C_4$ alkyl, $C_3$-$C_6$ cycloalkyl, $C_3$-$C_{10}$ cycloalkyl, $CH_2OH$, or $CH_2O$—$C_1$-$C_4$ alkyl;
$R_{10}$ and $R_{11}$ are independently hydrogen, halogen, $C_1$-$C_6$ alkyl, OH, $C_1$-$C_4$ alkyl, $C_3$-$C_6$ cycloalkyl, or $CH_2O$—$C_1$-$C_4$ alkyl;
$R_{12}$ is hydrogen, $CH_2OH$, $CH_2O$—$C_1$-$C_9$ alkyl, $C_3$-$C_{10}$ cycloalkyl, $CH_2OH$, or $CH_2O$—$C_1$-$C_4$ alkyl; and
$R_{13}$ is hydrogen, $C_1$-$C_9$ alkyl, $C_3$-$C_{10}$ cycloalkyl, or $CH_2OH$, $CH_2O$—$C_1$-$C_4$ alkyl.

In some embodiments, the compound of Formula (II) is:

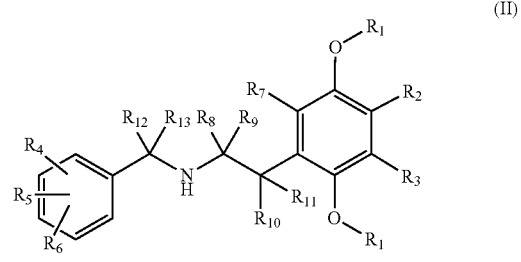

or a pharmaceutically acceptable salt thereof, wherein,
$R_1$ is independently at each position hydrogen, $C_1$-$C_6$ alkyl, or $C_1$-$C_6$ haloalkyl;
$R_2$, $R_3$ and $R_7$ are independently hydrogen, $C_1$-$C_6$ alkyl, $C_1$-$C_6$ haloalkyl, halogen, cyano, $OR_1$ or $SR_1$, wherein at least one of $R_2$ and $R_3$ is hydrogen;
$R_4$, $R_5$ and $R_6$ are independently hydrogen, $C_1$-$C_6$ alkyl, $C_1$-$C_6$ haloalkyl, halogen, cyano, $OR_1$, $SR_1$, $O(C=O)(R_{14})$, or $NH(C=O)(R_{14})$, wherein $R_{14}$ is $C_1$-$C_6$ alkyl;
$R_8$ and $R_9$ are independently hydrogen or $C_1$-$C_6$ alkyl;
$R_{10}$, and $R_{11}$ are independently hydrogen, halogen or $C_1$-$C_6$ alkyl;
$R_{12}$ is hydrogen, $CH_2OH$, $CH_2O$—$C_1$-$C_9$ alkyl, $C_3$-$C_{10}$ cycloalkyl, $CH_2OH$, $CH_2O$—$C_1$ to $C_4$ alkyl; and
$R_{13}$ is hydrogen, $C_1$-$C_9$ alkyl, $C_3$-$C_{10}$ cycloalkyl, $CH_2OH$, $CH_2O$—$C_1$ to $C_4$ alkyl.

In some embodiment, the compound of Formula (II) is a compound of Formula (II-A):

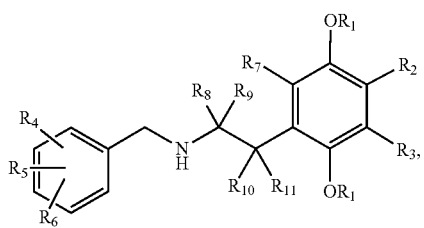

or a pharmaceutically acceptable salt thereof;
wherein,
$R_1$ is independently at each position hydrogen, $C_1$-$C_6$ alkyl, or $C_1$-$C_6$ haloalkyl;
$R_2$, $R_3$ and $R_7$ are independently hydrogen, $C_1$-$C_6$ alkyl, $C_1$-$C_6$ haloalkyl, halogen, cyano, $OR_1$ or $SR_1$, wherein at least one of $R_2$ and $R_3$ is hydrogen;
$R_4$, $R_5$ and $R_6$ are independently hydrogen, $C_1$-$C_6$ alkyl, $C_1$-$C_6$ haloalkyl, halogen, cyano, $OR_1$, $SR_1$, $O(C=O)(R_{12})$, or $NH(C=O)(R_{12})$, wherein $R_{12}$ is $C_1$-$C_6$ alkyl;
$R_8$ and $R_9$ are independently hydrogen or $C_1$-$C_6$ alkyl; and
$R_{10}$ and $R_{11}$ are independently hydrogen, halogen or $C_1$-$C_6$ alkyl.

In some embodiments, the compound of Formula (II) is a compound of Formula (II-B):

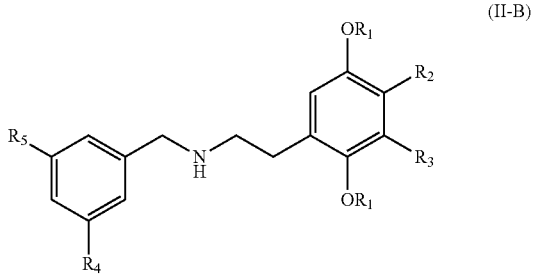

or a pharmaceutically acceptable salt thereof, wherein:
$R_1$, $R_2$, $R_3$ $R_4$, and $R_5$ are defined herein.

In some embodiments of the compounds of Formula (II), (II-A), or (II-B), $R_1$ is independently at each position hydrogen, $C_1$-$C_6$ alkyl, or $C_1$-$C_6$ haloalkyl.

In some embodiments of the compounds of Formula (II), (II-A), or (II-B), $R_1$ is independently at each position hydrogen or $C_1$-$C_6$ alkyl.

In some embodiments of the compounds of Formula (II), (II-A), or (II-B), $R_1$ is independently at each position $C_1$-$C_6$ alkyl.

In some embodiments of the compounds of Formula (II), (II-A), or (II-B), $R_1$ is independently at each position $C_1$-$C_3$ alkyl.

In some embodiments of the compounds of Formula (II), (II-A), or (II-B), $R_1$ is independently at each position methyl, ethyl, propyl, or isopropyl.

In some embodiments of the compounds of Formula (II), (II-A), or (II-B), $R_1$ is independently at each position $C_1$-$C_6$ haloalkyl. In some embodiments, $R_1$ is independently at each position $C_1$-$C_3$ haloalkyl. In some embodiments, $R_1$ is independently at each position $CF_3$.

In some embodiments of the compounds of Formula (II), (II-A), or (II-B), $R_1$ is methyl.

In some embodiments of the compounds of Formula (II), (II-A), or (II-B), $R_2$, and $R_3$ are independently hydrogen, $C_1$-$C_6$ alkyl, $C_1$-$C_6$ haloalkyl, halogen, cyano, $OR_1$ or $SR_1$, wherein at least one of $R_2$ and $R_3$ is hydrogen.

In some embodiments of the compounds of Formula (II), (II-A), or (II-B), $R_2$, and $R_3$ are independently hydrogen, $C_1$-$C_6$ alkyl, halogen, cyano, $OR_1$ or $SR_1$, wherein at least one of $R_2$ and $R_3$ is hydrogen.

In some embodiments of the compounds of Formula (II), (II-A), or (II-B), $R_2$ and $R_3$ are independently hydrogen, halogen. $C_1$-$C_6$ alkyl, or $C_1$-$C_6$ haloalkyl, wherein at least one of $R_2$ and $R_3$ is hydrogen.

In some embodiments of the compounds of Formula (II), (II-A), or (II-B), $R_2$ and $R_3$ are independently hydrogen, halogen, $C_1$-$C_3$ alkyl, or $C_1$-$C_3$ haloalkyl, wherein at least one of $R_2$ and $R_3$ is hydrogen.

In some embodiments of the compounds of Formula (II), (II-A), or (II-B), $R_2$ and $R_3$ are independently hydrogen, $C_1$-$C_6$ alkyl, or $C_1$-$C_6$ haloalkyl, wherein at least one of $R_2$ and $R_3$ is hydrogen.

In some embodiments of the compounds of Formula (II), (II-A), or (II-B), $R_2$ and $R_3$ are independently hydrogen, $C_1$-$C_3$ alkyl, or $C_1$-$C_3$ haloalkyl, wherein at least one of $R_2$ and $R_3$ is hydrogen.

In some embodiments of the compounds of Formula (II), (II-A), or (II-B), $R_2$ and $R_3$ are independently hydrogen, or $C_1$-$C_6$ alkyl, wherein at least one of $R_2$ and $R_3$ is hydrogen.

In some embodiments of the compounds of Formula (II), (II-A), or (II-B). $R_2$ and $R_3$ are independently hydrogen, or $C_1$-$C_3$ alkyl, wherein at least one of $R_2$ and $R_3$ is hydrogen.

In some embodiments of the compounds of Formula (II), (II-A), or (II-B), $R_2$ and $R_3$ are independently hydrogen, —$CF_3$, methyl or ethyl, wherein at least one of $R_2$ and $R_3$ is hydrogen.

In some embodiments of the compounds of Formula (II), (II-A), or (II-B), $R_2$ and $R_3$ are independently hydrogen, methyl or ethyl, wherein at least one of $R_2$ and $R_3$ is hydrogen.

In some embodiments of the compounds of Formula (II), (II-A), or (II-B), $R_2$ and $R_3$ are independently hydrogen or methyl, wherein at least one of $R_2$ and $R_3$ is hydrogen.

In some embodiments of the compounds of Formula (II), (II-A), or (II-B), $R_2$ is hydrogen, —$CF_3$, methyl or ethyl and $R_3$ is hydrogen.

In some embodiments of the compounds of Formula (II), (II-A), or (II-B), $R_2$ is hydrogen, methyl or ethyl and $R_3$ is hydrogen.

In some embodiments of the compounds of Formula (II), (II-A), or (II-B), $R_3$ is hydrogen.

In some embodiments of the compounds of Formula (II), (II-A), or (II-B), $R_2$ is hydrogen.

In some embodiments of the compounds of Formula (II), (II-A), or (II-B), $R_2$ is hydrogen and $R_3$ is hydrogen, —$CF_3$, methyl or ethyl.

In some embodiments of the compounds of Formula (II), (II-A), or (II-B), $R_2$ is hydrogen and $R_3$ is hydrogen, methyl or ethyl.

In some embodiments of the compounds of Formula (II), (II-A), or (II-B), $R_2$ and $R_3$ are hydrogen.

In some embodiments of the compounds of Formula (II), (II-A), or (II-B), $R_2$ is halogen and $R_3$ is hydrogen.

In some embodiments of the compounds of Formula (II), (II-A), or (II-B), $R_2$ is hydrogen and $R_3$ is halogen.

In some embodiments of the compounds of Formula (II), (II-A), or (II-B), $R_4$, $R_5$ and $R_6$ are independently hydrogen, $C_1$-$C_6$ alkyl, $C_1$-$C_6$ haloalkyl, halogen, cyano, $OR_1$, $SR_1$, $O(C=O)(R_{12})$, or $NH(C=O)(R_{12})$, wherein $R_{12}$ is $C_1$-$C_6$ alkyl.

In some embodiments of the compounds of Formula (II), (II-A), or (II-B), $R_4$ and $R_5$ are independently hydrogen, $C_1$-$C_6$ alkyl, halogen, cyano, $OR_1$, $SR_1$, $O(C=O)(R_{12})$, or $NH(C=O)(R_{12})$, wherein $R_{12}$ is $C_1$-$C_6$ alkyl.

In some embodiments of the compounds of Formula (II), (II-A), or (II-B), $R_4$ is $C_1$-$C_6$alkyl or $C_1$-$C_6$haloalkyl.

In some embodiments of the compounds of Formula (II), (II-A), or (II-B), $R_4$ is $C_1$-$C_6$alkyl.

In some embodiments of the compounds of Formula (II), (II-A), or (II-B), $R_4$ is —$CF_3$ or methyl.

In some embodiments of the compounds of Formula (II), (II-A), or (II-B), $R_4$ is methyl.

In some embodiments of the compounds of Formula (II), (II-A), or (II-B), $R_5$ is halogen.

In some embodiments of the compounds of Formula (II), (II-A), or (II-B), $R_5$ is chloro.

In some embodiments of the compounds of Formula (II) or (II-A), $R_6$ is hydrogen.

In some embodiments of the compounds of Formula (II) or (II-A), $R_7$ is hydrogen.

In some embodiments of the compounds of Formula (II) or (II-A), $R_8$ and $R_9$ are hydrogen.

In some embodiments of the compounds of Formula (II) or (II-A), $R_{10}$ and $R_{11}$ are hydrogen.

In some embodiments of the compounds of Formula (II) or (II-A), $R_{10}$ and $R_1$ are fluoro.

In some embodiments of the compounds of Formula (II), $R_{11}$ and $R_{12}$ are hydrogen.

In some embodiments, provided herein is one or more compounds selected from Table 1.

In some embodiments, provided herein is one or more pharmaceutically acceptable salts of a compound selected from Table 1.

TABLE 1

Compounds of the Present Disclosure

| No. | Structure |
|---|---|
| 1-1 | (structure) |
| 1-2 | (structure) |
| 1-2A | (structure) |
| 1-2B | (structure) |
| 1-3 | (structure) |
| 1-4 | (structure) |
| 1-5 | (structure) |

TABLE 1-continued

Compounds of the Present Disclosure

| No. | Structure |
|---|---|
| 1-6 | 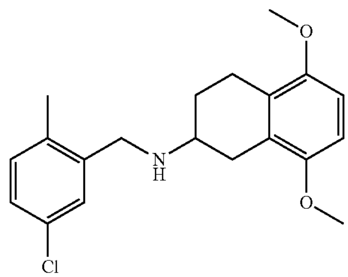 [SMILES: COc1ccc(OC)c2c1CCC(NCc1cc(Cl)ccc1C)C2] |
| 1-7 | 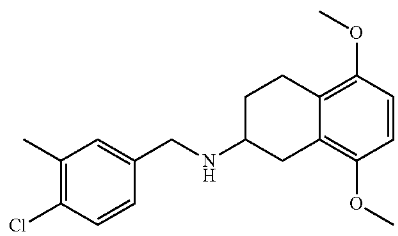 [SMILES: COc1ccc(OC)c2c1CCC(NCc1ccc(Cl)c(C)c1)C2] |
| 1-8 | 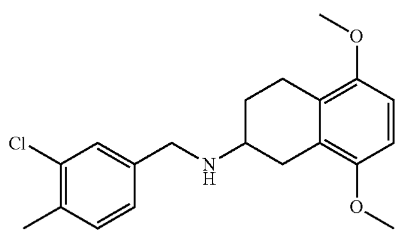 |
| 1-9 | 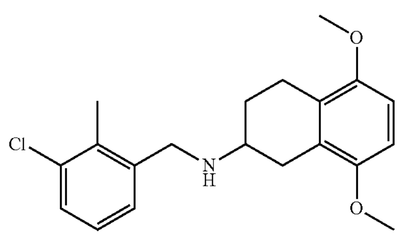 [SMILES: COc1ccc(OC)c2c1CCC(NCc1cccc(Cl)c1C)C2] |
| 1-10 | 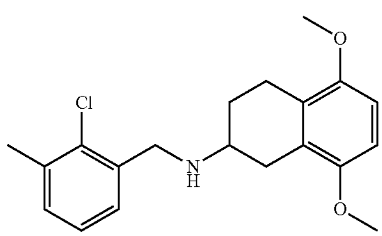 |
| 1-11 | 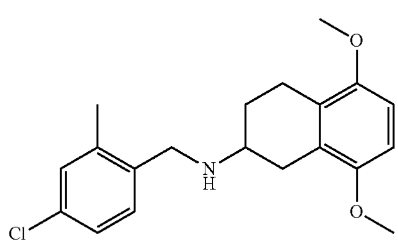 [SMILES: COc1ccc(OC)c2c1CCC(NCc1ccc(Cl)cc1C)C2] |
| 1-12 | |
| 1-13 | |
| 1-14 | |
| 1-15 | |
| 1-16 | |
| 1-17 | |

TABLE 1-continued

Compounds of the Present Disclosure

| No. | Structure |
|---|---|
| 1-18 | 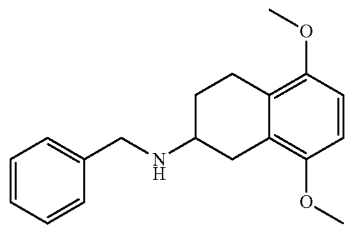 [SMILES: COc1ccc(OC)c2c1CCC(NCc1ccccc1)C2] |
| 1-19 | 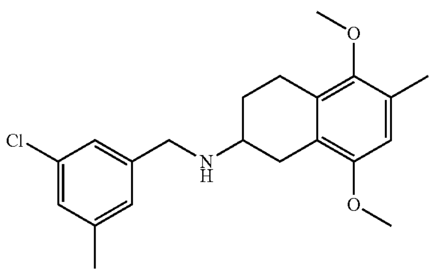 [SMILES: COc1cc(C)c(OC)c2c1CC(NCc1cc(C)cc(Cl)c1)CC2] |
| 1-20 | 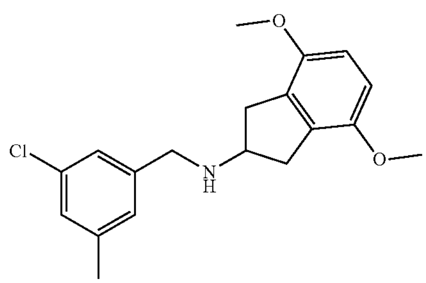 [SMILES: COc1ccc(OC)c2c1CC(NCc1cc(C)cc(Cl)c1)C2] |
| 1-21 | 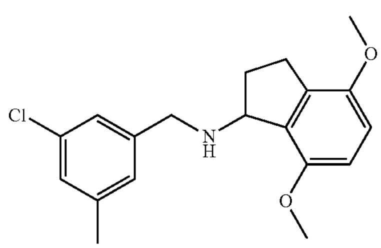 [SMILES: COc1ccc(OC)c2c1CCC2NCc1cc(C)cc(Cl)c1] |

In some embodiments, provided herein is the compound:

(1-1 HCl)

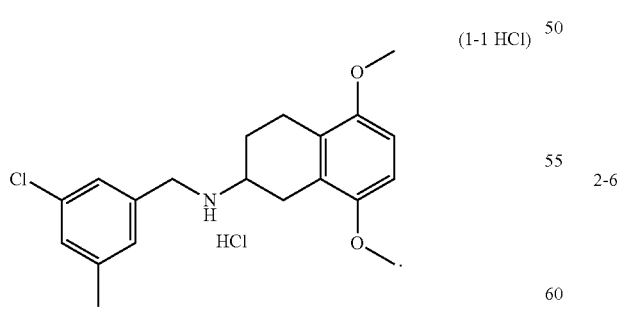

In some embodiments, provided herein is one or more compounds selected from Table 2.

In some embodiments, provided herein is one or more pharmaceutically acceptable salts of a compound selected from Table 2.

TABLE 2

Compounds of the Present Disclosure

| No. | Structure |
|---|---|
| 2-1 | 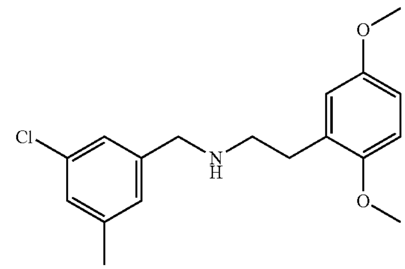 [SMILES: COc1ccc(OC)c(CCNCc2cc(C)cc(Cl)c2)c1] |
| 2-2 | 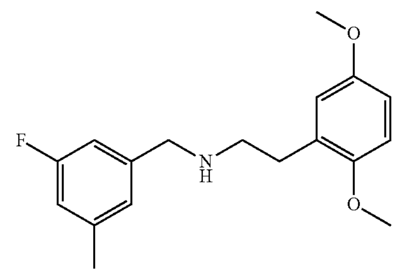 |
| 2-3 | ·HCl |
| 2-4 | 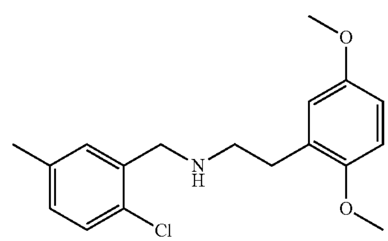 |
| 2-5 | 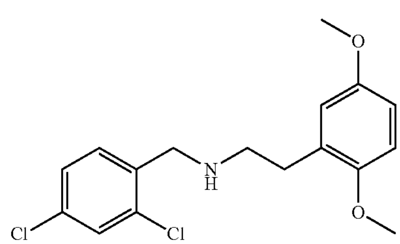 [SMILES: COc1ccc(OC)c(CCNCc2ccc(Cl)cc2Cl)c1] |
| 2-6 | 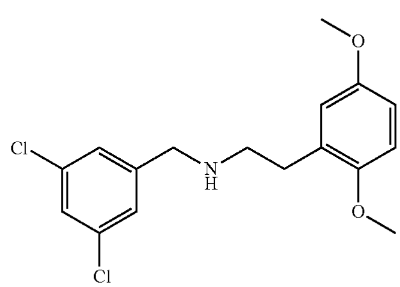 [SMILES: COc1ccc(OC)c(CCNCc2cc(Cl)cc(Cl)c2)c1] |

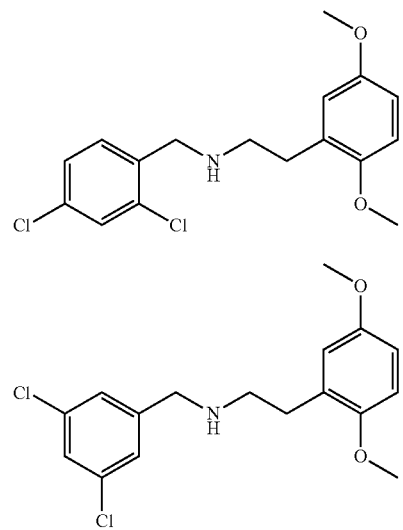

TABLE 2-continued
Compounds of the Present Disclosure
| No. | Structure |
|---|---|
| 2-7 | 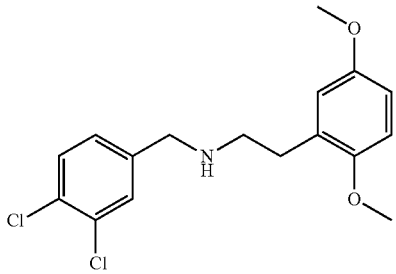 [SMILES: COc1ccc(OC)c(CCNCc2ccc(Cl)c(Cl)c2)c1] |
| 2-8 | 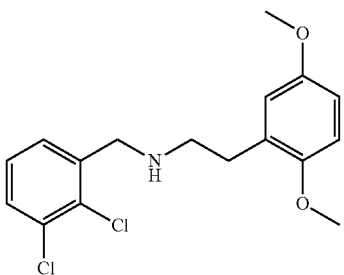 |
| 2-9 | 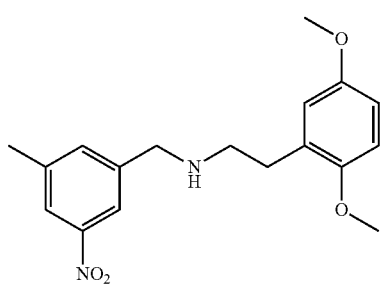 [SMILES: COc1ccc(OC)c(CCNCc2cc(C)cc([N+](=O)[O-])c2)c1] |
| 2-10 | 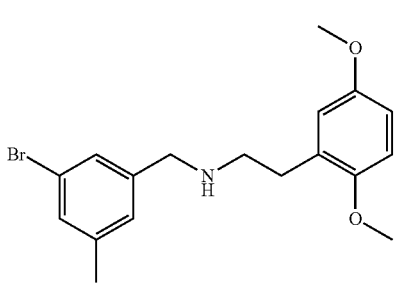 [SMILES: COc1ccc(OC)c(CCNCc2cc(C)cc(Br)c2)c1] |
| 2-11 | 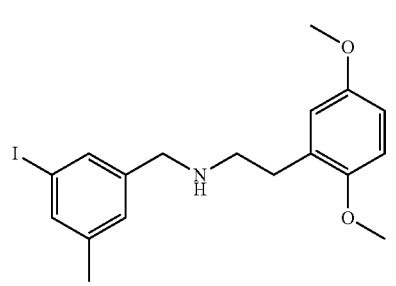 [SMILES: COc1ccc(OC)c(CCNCc2cc(C)cc(I)c2)c1] |
| 2-12 | 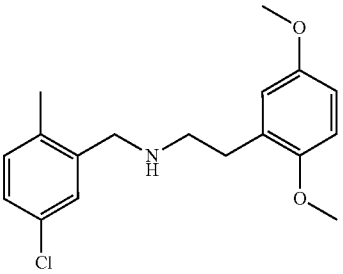 [SMILES: COc1ccc(OC)c(CCNCc2cc(Cl)ccc2C)c1] |
| 2-13 | 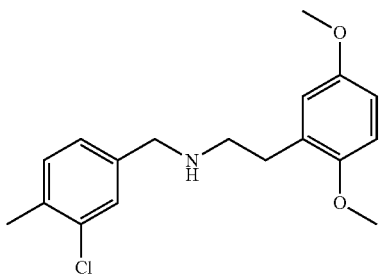 |
| 2-14 | 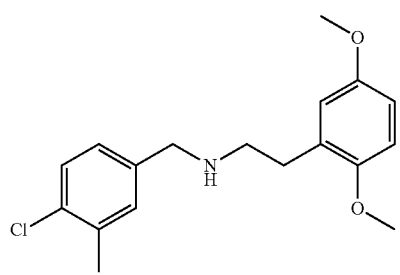 [SMILES: COc1ccc(OC)c(CCNCc2ccc(Cl)c(C)c2)c1] |
| 2-15 | 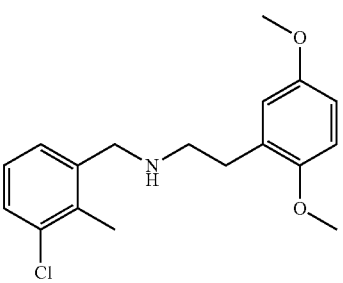 [SMILES: COc1ccc(OC)c(CCNCc2cccc(Cl)c2C)c1] |
| 2-16 | 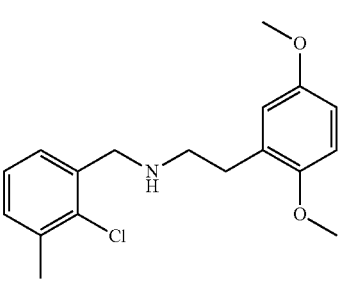 |

TABLE 2-continued
Compounds of the Present Disclosure
| No. | Structure |
|---|---|
| 2-17 | 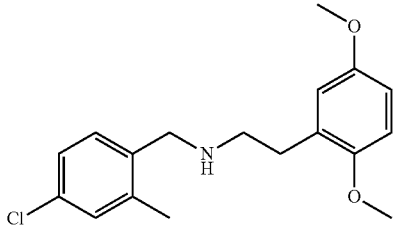 |
| 2-18 | 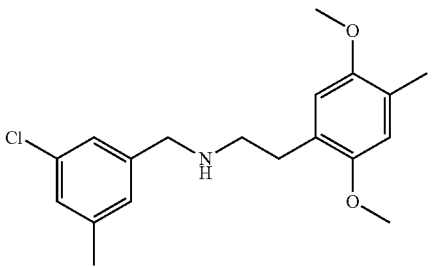 [SMILES: COc1cc(CCNCc2cc(C)cc(Cl)c2)c(OC)cc1C] |
| 2-19 | 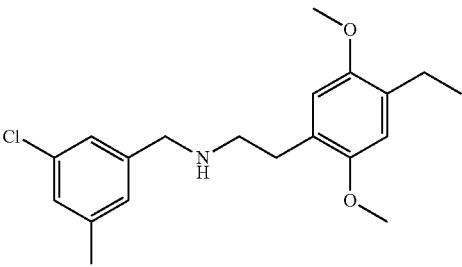 [SMILES: CCc1cc(OC)c(CCNCc2cc(C)cc(Cl)c2)cc1OC] |
| 2-20 | 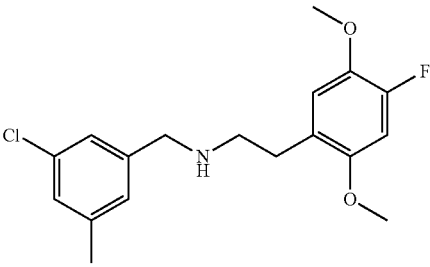 [SMILES: COc1cc(CCNCc2cc(C)cc(Cl)c2)c(OC)cc1F] |
| 2-21 | 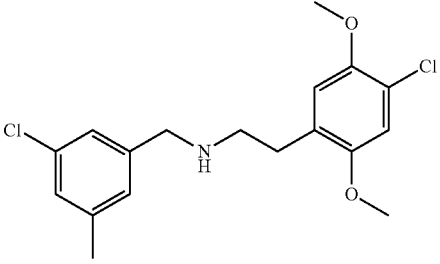 [SMILES: COc1cc(CCNCc2cc(C)cc(Cl)c2)c(OC)cc1Cl] |
| 2-22 | 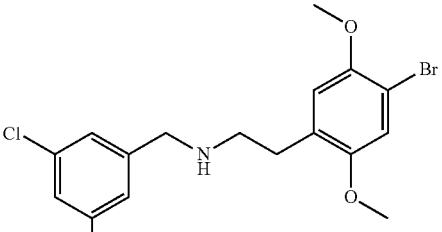 |
| 2-23 | 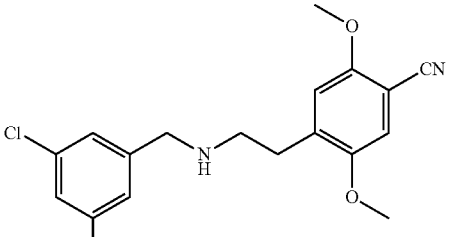 |
| 2-24 | 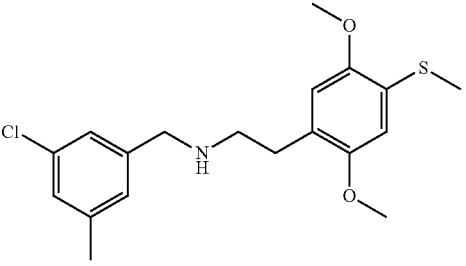 [SMILES: COc1cc(SC)c(OC)cc1CCNCc1cc(C)cc(Cl)c1] |
| 2-25 | 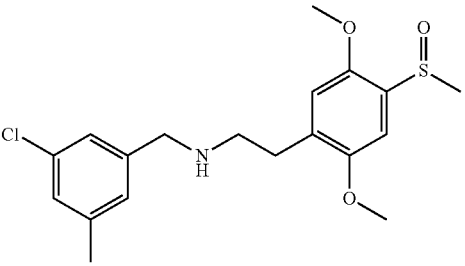 [SMILES: COc1cc(S(C)=O)c(OC)cc1CCNCc1cc(C)cc(Cl)c1] |
| 2-26 | 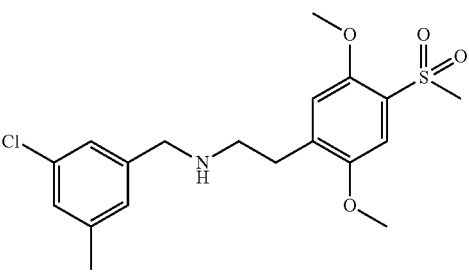 [SMILES: COc1cc(S(C)(=O)=O)c(OC)cc1CCNCc1cc(C)cc(Cl)c1] |

TABLE 2-continued
Compounds of the Present Disclosure
| No. | Structure |
|---|---|
| 2-27 | 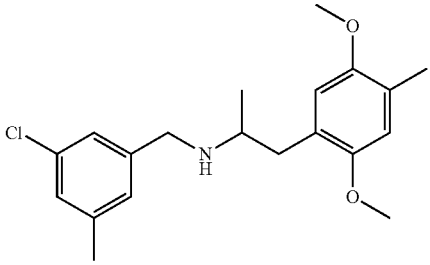 [SMILES: COc1cc(CC(C)NCc2cc(C)cc(Cl)c2)c(OC)cc1C] |
| 2-28 | 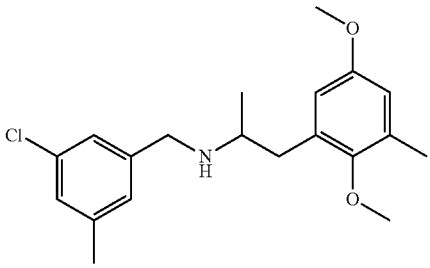 [SMILES: COc1cc(C)c(OC)c(CC(C)NCc2cc(C)cc(Cl)c2)c1] |
| 2-29 | 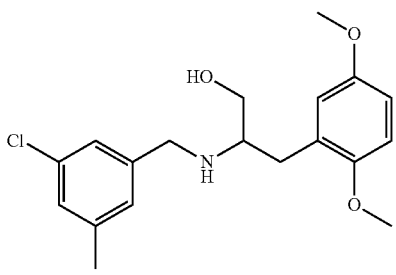 [SMILES: COc1ccc(OC)c(CC(CO)NCc2cc(C)cc(Cl)c2)c1] |
| 2-30 | 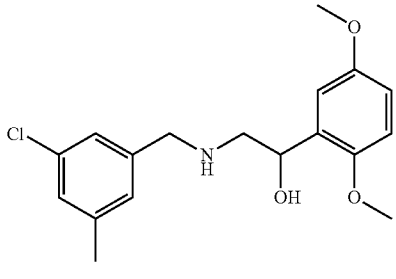 [SMILES: COc1ccc(OC)c(C(O)CNCc2cc(C)cc(Cl)c2)c1] |
| 2-31 | 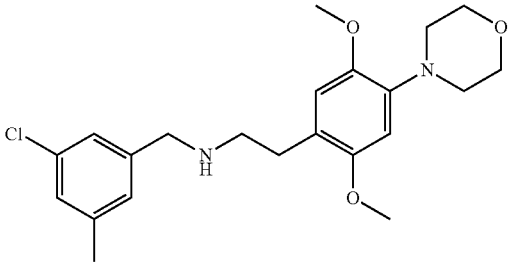 [SMILES: COc1cc(N2CCOCC2)c(OC)cc1CCNCc1cc(C)cc(Cl)c1] |
| 2-32 | 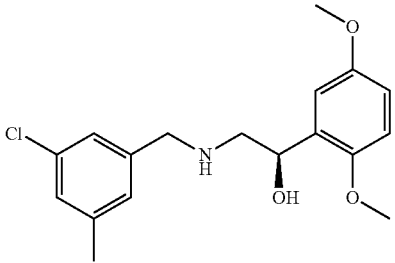 [SMILES: COc1ccc(OC)c([C@@H](O)CNCc2cc(C)cc(Cl)c2)c1] |
| 2-33 | 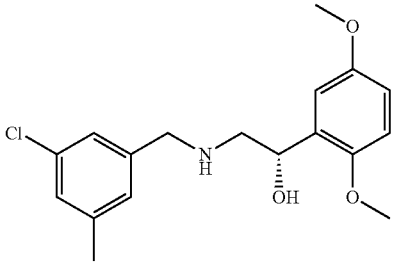 [SMILES: COc1ccc(OC)c([C@H](O)CNCc2cc(C)cc(Cl)c2)c1] |
| 2-34 | 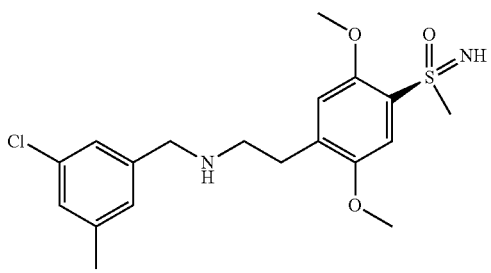 [SMILES: COc1cc([S@](C)(=N)=O)c(OC)cc1CCNCc1cc(C)cc(Cl)c1] |
| 2-35 | 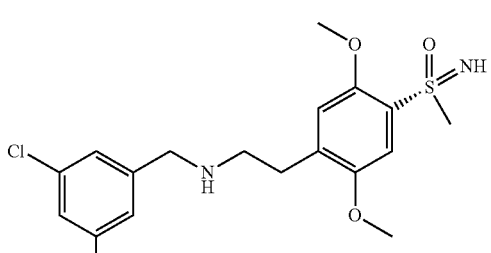 |
| 2-36 | 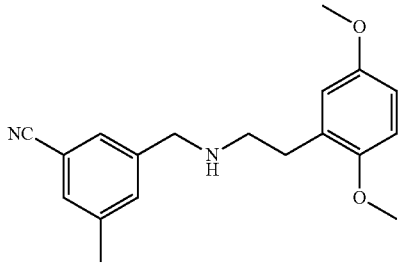 [SMILES: COc1ccc(OC)c(CCNCc2cc(C)cc(C#N)c2)c1] |

TABLE 2-continued

Compounds of the Present Disclosure

| No. | Structure |
|---|---|
| 2-37 | 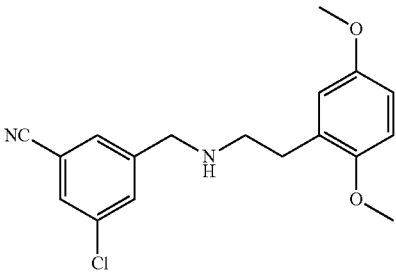 |
| 2-38 | 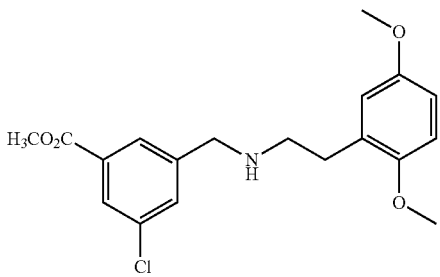 [SMILES: COC(=O)c1cc(Cl)cc(CNCCc2cc(OC)ccc2OC)c1] |
| 2-39 | 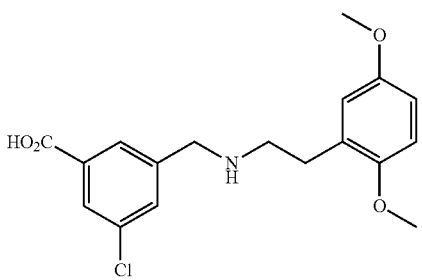 [SMILES: COc1ccc(OC)c(CCNCc2cc(Cl)cc(C(=O)O)c2)c1] |
| 2-40 | 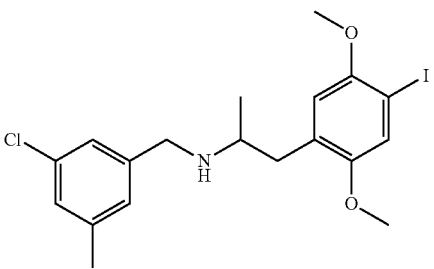 [SMILES: COc1cc(CC(C)NCc2cc(C)cc(Cl)c2)c(OC)cc1I] |
| 2-41 | 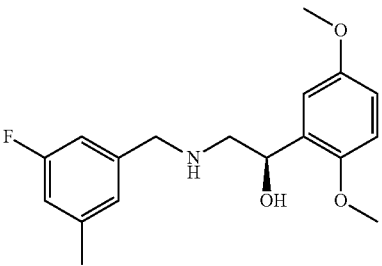 [SMILES: COc1ccc(OC)c([C@@H](O)CNCc2cc(C)cc(F)c2)c1] |
| 2-42 | 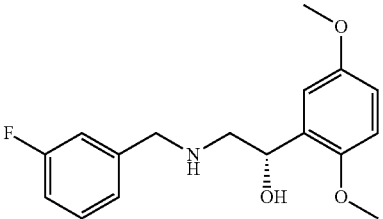 |

Compositions

In some embodiments of the present disclosure, a pharmaceutical composition comprising a therapeutically effective amounts of one or more compounds of the present disclosure (e.g., a compound of Formula (I), (I-A) (II), (II-A), (II-B), Table 1 or Table 2) or a pharmaceutically acceptable salt thereof and a pharmaceutically acceptable excipient is provided.

The pharmaceutically acceptable excipients and adjuvants are added to the composition or formulation for a variety of purposes. In some embodiments, a pharmaceutical composition comprising one or more compounds disclosed herein, or a pharmaceutically acceptable salt thereof, further comprise a pharmaceutically acceptable carrier. In some embodiments, a pharmaceutically acceptable carrier includes a pharmaceutically acceptable excipient, binder, and/or diluent. In some embodiments, suitable pharmaceutically acceptable carriers include, but are not limited to, inert solid fillers or diluents and sterile aqueous or organic solutions. In some embodiments, suitable pharmaceutically acceptable excipients include, but are not limited to, water, salt solutions, alcohol, polyethylene glycols, gelatin, lactose, amylase, magnesium stearate, talc, silicic acid, viscous paraffin, and the like.

For the purposes of this disclosure, the compounds of the present disclosure can be formulated for administration by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters.

Methods of Treatment

The compounds of the present disclosure find use, for example, in methods for modulating a serotonin receptor, e.g., 5-HT2A receptor. Accordingly, in some embodiments, the present disclosure provides the use of any one of compounds of the present disclosure (e.g., a compound of Formula (I), (I-A), (II), (II-A), (II-B), Table 1 or Table 2) or a pharmaceutically acceptable salt thereof, for modulating serotonin receptor activity. Modulating serotonin (e.g., 5-HT2A) receptor activity can be in a subject in need thereof (e.g., a mammalian subject, such as a human) and for treatment of any of the described conditions or diseases. In some embodiments, modulating is activating or agonizing a serotonin receptor, e.g., 5-HT2A receptor. In some embodiments, the subject is a human.

In some embodiments, the present disclosure provides methods of treating a disease or disorder that is treatable by administration of a serotonin receptor agonist, e.g., 5-HT2A receptor agonist. In some embodiments, the agonist is a partial agonist of the 5-HT2A receptor. In some embodiments, the agonist is a full agonist of the 5-HT2A receptor.

In some embodiments, the compounds of the present disclosure are used for treating, a mental health disease or disorder in a subject in need thereof, the method comprising administering to the subject a therapeutically effective amount of a compound of the present disclosure (e.g., e.g., a compound of Formula (I), (I-A), (II), (II-A), (II-B) Table 1 or Table 2 or a pharmaceutically acceptable salt thereof) or a pharmaceutical composition comprising a compound of the present disclosure (e.g., e.g., a compound of Formula (I), (I-A), (II), (II-A), (II-B), Table 1 or Table 2 or a pharmaceutically acceptable salt thereof) and a pharmaceutically acceptable excipient.

In some embodiments, the mental health disease or disorder is selected from the group consisting of depression, substance use disorders (SUD) and eating disorders.

In some embodiments, the mental health disease or disorder is an eating disorder. Eating disorders include illnesses such as anorexia nervosa, bulimia nervosa, and other disorders related to eating (e.g., binge eating).

In some embodiments, the mental health disease or disorder is a mood disorder. Mood disorders include e.g., depressive disorders, such as major depressive disorder or treatment resistant depression.

In some embodiments, the mental health disorder is a substance abuse disorder. In some embodiments, substance use related disorders are disorders of maladaptive patterns of substance use, and include criteria, such as recurrent substance use related problems, tolerance to a substance, withdrawal upon discontinuing use, an inability to cut down or control use of the substance, and giving up important social, occupational, or recreational activities because of using the substance. See e.g., the Diagnostic and Statistical Manual of Mental Disorders (DSM-5). In some embodiments, the substance use related disorder is a disorder resulting from the use of: alcohol; caffeine; cannabis; hallucinogens (such as phencyclidine or similarly acting arylcyclohexylamines, and other hallucinogens, such as LSD); inhalants; opioids; sedatives, hypnotics, or anxiolytics; stimulants (including amphetamine-type substances, cocaine, and other stimulants); tobacco; and other substances.

EXAMPLES

Unless otherwise noted, all materials/reagents were obtained from commercial suppliers and used without further purification. Reactions were monitored by LC-MS and/or thin layer chromatography (TLC) on silica gel 60 F254 (0.2 mm) pre-coated aluminum foil or glass-backed and visualized using UV light. $^1$HNMR (400 MHz) spectra was recorded on Broker spectrometers at RT with TMS or the residual solvent peak as the internal standard. Chemical shifts are given in (6) and the coupling constants (J) are given as absolute values in Hertz (Hz). The multiplicities in $^1$HNMR spectra are abbreviated as follows: s (singlet), d (doublet), t (triplet), q (quartet), m (multiplet), br or broad (broadened). Preparative HPLC purifications were performed on Shimadzu LC-6AD. All purification work was completed using a Shim-pack PREP-DDS(H)KIT Column. The mobile phases were water (with 0.1% $HCO_2H$) and acetonitrile; all reagents used were of HPLC grade. The flow rate was 10 ml/min. LC-MS analyses were performed on Shimadzu LCMS-2020 equipped with LC-20AD or 30AD pumps, SPD-M20A PDA and Alltech 3300 ELSD; Mobile Phase: A: Water (0.1% Formic acid), B: ACN; 5 minute run; Column: Sepax BR-C18 4.6*50 mm, 3 um; Flow Rate: 1.0 ml/min; Oven Temperature: 40° C.; Gradient: 20% B for 0.2 min, increase to 70% B within 1.8 min, 70% B for 2.8 min, back to 20% B within 0.2 min, 20% B for 2 min). Preparative TLC was performed on Whatman LK6F Silica Gel 60A size 20×20 cm plates with a thickness of 1000 μm or equivalent.

Example 1: Synthesis of N-(3-chloro-5-methylbenzyl)-5,8-dimethoxy-1,2,3,4-tetrahydronaphthalen-2-amine hydrochloride (1-1·HCl)

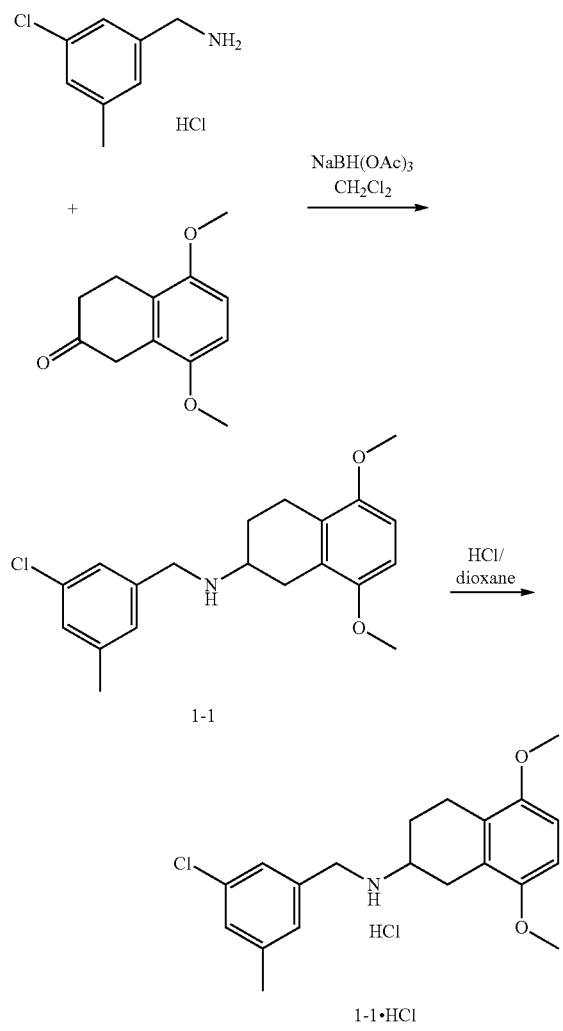

To a solution of 5,8-dimethoxy-3,4-dihydronaphthalen-2 (1H)-one (400 mg, 1.94 mmol, 1.0 eq.) and (3-chloro-5-methylphenyl) methanamine hydrochloride (380 mg, 1.94 mmol, 1.0 eq.) in $CH_2Cl_2$ (10 ml) was added $NaBH(OAc)_3$ (600 mg, 2.83 mmol, 1.5 eq.). The resulting mixture was stirred at room temperature overnight. The reaction mixture was quenched with aqueous sodium bicarbonate solution, extracted with DCM (2×10 mL), dried over anhydrous sodium sulfate and concentrated under reduced pressure to give a crude residue which was purified through a silica gel flash chromatography column (eluted with 1% methanol in dichloromethane containing 1% ammonium hydroxide) to afford compound 1-1 as free the amine. The amine was converted to its HCl salt as a pale solid (400 mg, yield 60%) after treatment with hydrochloric acid in 1,4-Dioxane. Formula: $C_{20}H_{24}ClNO_2$; MW: 345.15. LCMS: (ES$^+$): m/z 347.0 [M+H]$^+$. $t_R$=2.1 min. $^1$HNMR (400 MHz, DMSO-d$_6$): δ 9.37-9.51 (br, 2H), 7.55 (s, 1H), 7.40 (s, 1H), 7.33 (s, 1H), 6.76 (s, 2H), 4.23-2.24 (br, 2H), 3.74 (s, 3H), 3.72 (s, 3H), 3.19-3.25 (m, 1H), 2.87-2.92 (m, 1H), 2.50-2.68 (m, 1H), 2.43-2.48 (m, 1H), 2.33 (s, 4H), 1.71-1.75 (m, 1H).

Example 2: Synthesis of N-(3-chloro-5-methylbenzyl)-6-iodo-5,8-dimethoxy-1,2,3,4-tetrahydronaphthalen-2-amine (1-2A) and N-(3-chloro-5-methylbenzyl)-7-iodo-5,8-dimethoxy-1,2,3,4-tetrahydronaphthalen-2-amine (1-2B)

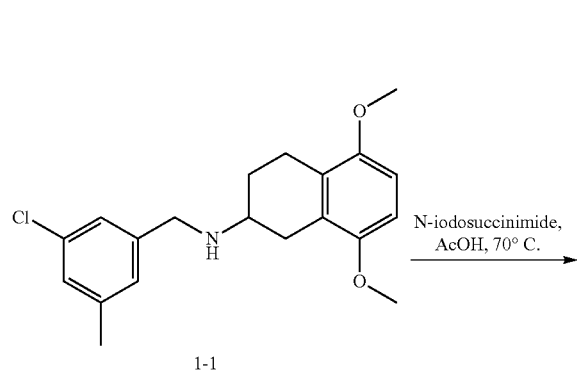

A solution of 1-1 (300 mg, 0.78 mmol, 1.0 eq.) and N-iodosuccinimide (350 mg, 1.5 mmol, 2.0 eq.) in AcOH (6 ml) was stirred at 70° C. for 48 h. The reaction was quenched with aqueous sodium bicarbonate solution, extracted with $CH_2Cl_2$ (2×10 ml), dried over anhydrous sodium sulfate and concentrated under reduced pressure to give a crude residue which was purified through preparative-HPLC to afford 1-2 as a mixture of 6/7 iodo-isomers 1-2A and 1-2B (ratio 1:1, 5.0 mg, brown solid, yield 2%). Formula: $C_{20}H_{23}ClINO_2$; MW: 471.76, LCMS: (ES$^+$): m/z 372.2 [M+H]$^+$. $t_R$=2.3 min. $^1$HNMR (400 MHz, DMSO-d$_6$): δ 7.42 (s, 1H), 7.35 (s, 1H), 7.32 (s, 1H), 7.19 (s, 1H), 4.33-4.34 (s, 2H), 3.81-3.83 (s, 3H), 3.74-3.76 (s, 3H), 3.52-3.58 (m, 1H), 3.43-3.48 (m, 1H), 3.13-3.19 (m, 1H), 3.52-3.58 (m, 1H), 2.98-3.04 (m, 1H), 2.76-2.83 (m, 1H), 2.56-2.67 (m, 1H), 2.41 (s, 3H), 1.74-1.84 (m, 1H).

Example 3: N-(3-fluoro-5-methylbenzyl)-5,8-dimethoxy-1,2,3,4-tetrahydronaphthalen-2-amine (1-3)

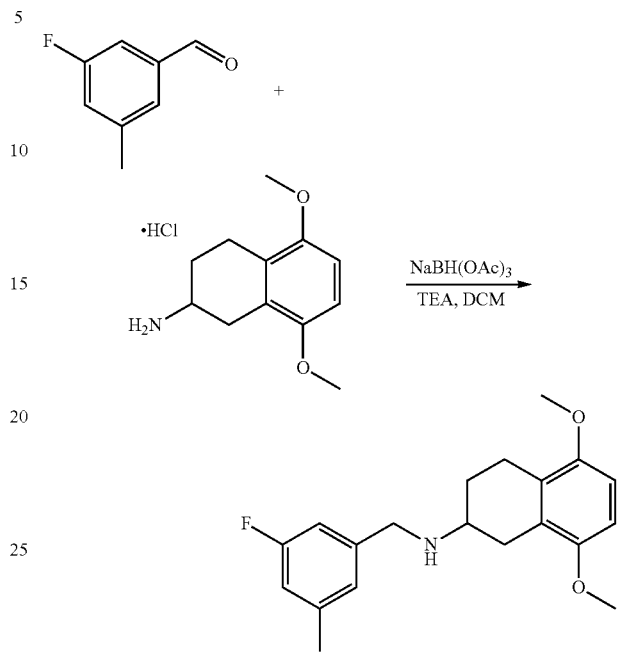

To a solution of 5,8-dimethoxy-1,2,3,4-tetrahydronaphthalen-2-amine hydrochloride (141 mg, 0.58 mmol, 1 eq) in DCM (5 mL) was added 3-fluoro-5-methylbenzaldehyde (80 mg, 0.58 mmol, 1 eq), TEA (110 mg, 1.16 mmol, 1.5 eq) and NaBH(OAc)$_3$ (369 mg, 1.74 mmol, 3 eq) at RT. And the resulting mixture was stirred overnight. The reaction was quenched with aqueous NaHCO$_3$ solution and extracted with EA (3×50 mL). The combined organic layers were washed with brine, dried over Na$_2$SO$_4$, filtered and concentrated to give a crude product which was purified by silica gel column chromatography (DCM:MeOH=100:1) to afford the title compound as a colorless oil (162 mg, 84%). LCMS: 2.325 min, m/z 330.40 [M+H]$^+$. $^1$H NMR (400 MHz, Methanol-d$_4$) δ 7.74-7.62 (m, 2H), 7.57-7.43 (m, 1H), 6.79 (s, 2H), 4.52 (s, 2H), 3.81 (s, 3H), 3.80 (s, 3H), 3.72-3.57 (m, 1H), 3.48-3.39 (m, 1H), 3.14-3.03 (m, 1H), 2.77-2.60 (m, 2H), 2.51-2.38 (m, 1H), 1.84 (qd, J=11.7, 5.6 Hz, 1H).

Example 4: N-(3-bromo-5-methylbenzyl)-5,8-dimethoxy-1,2,3,4-tetrahydronaphthalen-2-amine (1-4)

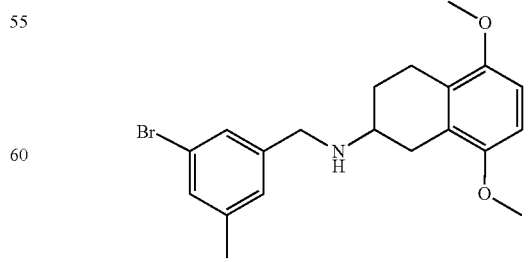

The same procedure used for the preparation of 1-3 was applied to afford the title compound as a colorless oil (111 mg, 71%). LCMS: 2.510 min, m/z 391.65 [M+H]+. 1H NMR (400 MHz, Methanol-d4) δ 7.58 (s, 1H), 7.51 (s, 1H), 7.37 (s, 1H), 6.78 (s, 2H), 4.33 (s, 2H), 3.81 (s, 3H), 3.79 (s, 3H), 3.59-3.46 (m, 1H), 3.44-3.35 (m, 1H), 3.13-3.02 (m, 1H), 2.74-2.54 (m, 2H), 2.48-2.33 (m, 4H), 1.79 (qd, J=12.0, 5.5 Hz, 1H).

Example 5: N-(3-iodo-5-methylbenzyl)-5,8-dimethoxy-1,2,3,4-tetrahydronaphthalen-2-amine (1-5)

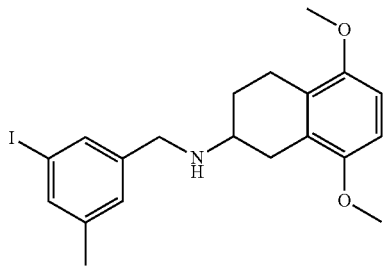

The same procedure used for the preparation of 1-3 was applied to afford the title compound as a colorless oil (125 mg, 84%). LCMS: 2.440 min, m/z 438.50 [M+H]+. 1H NMR (400 MHz, Methanol-d4) δ 7.77 (s, 1H), 7.71 (s, 1H), 7.39 (s, 1H), 6.78 (s, 2H), 4.29 (s, 2H), 3.81 (s, 3H), 3.79 (s, 3H), 3.59-3.47 (m, 1H), 3.43-3.35 (m, 1H), 3.12-2.99 (m, 1H), 2.72-2.55 (m, 2H), 2.46-2.34 (m, 4H), 1.78 (qd, J=12.0, 5.5 Hz, 1H).

Example 6: N-(2-chloro-5-methylbenzyl)-5,8-dimethoxy-1,2,3,4-tetrahydronaphthalen-2-amine (1-6)

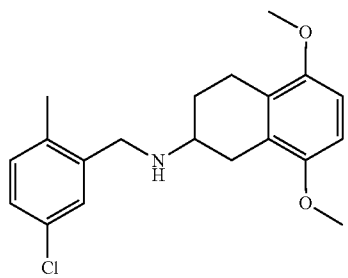 [SMILES: COc1ccc(OC)c2c1CCC(NCc1cc(Cl)ccc1C)C2]

The same procedure used for the preparation of 1-3 was applied to afford the title compound as a colorless oil (130 mg, 72%). LCMS: 2.463 min, m/z 346.15 [M+H]+. 1H NMR (400 MHz, Methanol-d4) δ 7.57 (d, J=2.1 Hz, 1H), 7.45-7.30 (m, 2H), 6.79 (s, 2H), 4.40 (s, 2H), 3.82 (s, 3H), 3.80 (s, 3H), 3.71-3.55 (m, 1H), 3.49-3.38 (m, 1H), 3.18-2.99 (m, 1H), 2.77-2.58 (m, 2H), 2.52-2.37 (m, 4H), 1.82 (qd, J=11.9, 5.5 Hz, 1H).

Example 7: N-(4-chloro-3-methylbenzyl)-5,8-dimethoxy-1,2,3,4-tetrahydronaphthalen-2-amine (1-7)

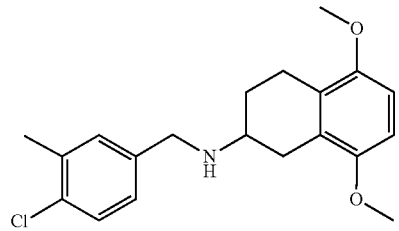 [SMILES: COc1ccc(OC)c2c1CCC(NCc1ccc(Cl)c(C)c1)C2]

The same procedure used for the preparation of 1-3 was applied to afford the title compound which was converted to the HCl salt EGX-13-6·HCl (35 mg, 30%) as a white solid after treatment with HCl in dioxane. LCMS: m/z 345.9 [M+H]+. 1H NMR (400 MHz, CD3OD) 7.53 (d, J=1.7 Hz, 1H), 7.48 (d, J=8.2 Hz, 1H), 7.39 (dd, J=8.2, 2.0 Hz, 1H), 6.77 (s, 2H), 4.33 (s, 2H), 3.81 (s, 3H), 3.79 (s, 3H), 3.60-3.47 (m, 1H), 3.39 (dd, J=17.2, 4.7 Hz, 1H), 3.06 (ddd, J=17.7, 5.3, 3.0 Hz, 1H), 2.72-2.57 (m, 2H), 2.44 (s, 3H), 2.41 (dd, J=6.2, 3.5 Hz, 1H), 1.81 (qd, J=11.9, 5.6 Hz, 1H).

Example 8: N-(3-chloro-4-methylbenzyl)-5,8-dimethoxy-1,2,3,4-tetrahydronaphthalen-2-amine (1-8)

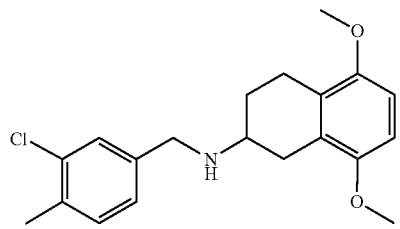

The same procedure used for the preparation of 1-3 was applied to afford the title compound (35 mg, 30%) as a white solid after treatment with HCl in dioxane. LCMS: m/z 346 [M+H]+. 1H NMR (400 MHz, Solvent: CD3OD) ppm 7.63 (s, 1H), 7.43 (d, J=7.1 Hz, 2H), 6.77 (s, 2H), 4.34 (s, 2H), 3.81 (s, 3H), 3.79 (s, 3H), 3.53 (tdd, J=11.3, 5.4, 2.9 Hz, 1H), 3.44-3.35 (m, 1H), 3.06 (ddd, J=17.7, 5.4, 3.1 Hz, 1H), 2.72-2.57 (m, 2H), 2.42 (s, 3H), 2.40 (dd, J=5.6, 2.6 Hz, 1H), 1.80 (qd, J=11.8, 5.6 Hz, 1H).

Example 9: N-(3-chloro-2-methylbenzyl)-5,8-dimethoxy-1,2,3,4-tetrahydronaphthalen-2-amine (1-9)

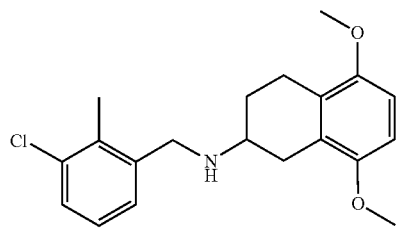 [SMILES: COc1ccc(OC)c2c1CCC(NCc1cccc(Cl)c1C)C2]

The same procedure used for the preparation of 3-1 was applied to afford the title compound (20 mg, 20%) as a white solid after treatment with HCl in dioxane. LCMS: (ES+): m/z 346.3 [M+H]+. ¹H NMR (400 MHz, MeOD) δ 7.50 (d, J=7.9 Hz, 1H), 7.46 (d, J=7.5 Hz, 1H), 7.30 (t, J=7.8 Hz, 1H), 6.76 (s, 2H), 4.45 (s, 2H), 3.79 (s, 3H), 3.78 (s, 3H), 3.64 (d, J=11.4 Hz, 1H), 3.43 (dd, J=16.4, 4.4 Hz, 1H), 3.07 (d, J=18.1 Hz, 1H), 2.66 (dd, J=15.8, 10.3 Hz, 2H), 2.52 (s, 3H), 2.45 (d, J=12.7 Hz, 1H), 1.81 (qd, J=11.6, 5.4 Hz, 1H).

Example 10: N-(2-chloro-3-methylbenzyl)-5,8-dimethoxy-1,2,3,4-tetrahydronaphthalen-2-amine (1-10)

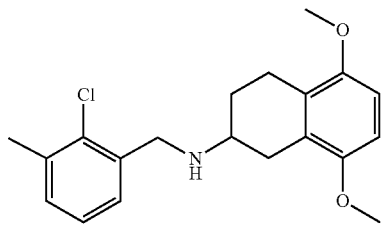

The same procedure used for the preparation of 3-1 was applied to afford the title compound (50 mg, 42%) as a white solid after treatment with HCl in dioxane. LCMS: m/z 346 [M+H]+. ¹H NMR (400 MHz, Solvent: CD₃OD) 7.54-7.44 (m, 2H), 7.36 (t, J=7.6 Hz, 1H), 6.78 (s, 2H), 4.54 (s, 2H), 3.82 (s, 3H), 3.80 (s, 3H), 3.69-3.58 (m, 1H), 3.43 (dd, J=17.2, 4.7 Hz, 1H), 3.09 (ddd, J=17.8, 5.6, 3.2 Hz, 1H), 2.68 (ddd, J=17.0, 10.8, 4.5 Hz, 2H), 2.48 (s, 3H), 2.47-2.42 (m, 1H), 1.84 (qd, J=11.9, 5.5 Hz, 1H).

Example 11: N-(4-chloro-2-methylbenzyl)-5,8-dimethoxy-1,2,3,4-tetrahydronaphthalen-2-amine (1-11)

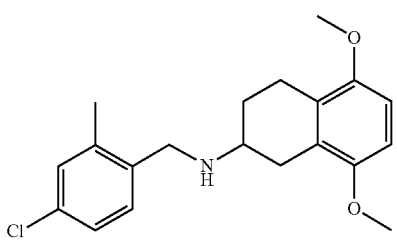 [SMILES: COc1ccc(OC)c2c1CCC(NCc1ccc(Cl)cc1C)C2]

The same procedure used for the preparation of 3-1 was applied to afford the title compound (40 mg, 36%) as a white solid after treatment with HCl in dioxane. LCMS: m/z 346 [M+H]+. ¹H NMR (400 MHz, Solvent: CD₃OD) 7.51 (d, J=8.2 Hz, 1H), 7.39 (d, J=1.5 Hz, ¹H), 7.34 (dd, J=8.2, 2.0 Hz, 1H), 6.78 (s, 2H), 4.39 (s, 2H), 3.81 (s, 3H), 3.80 (s, 3H), 3.68-3.57 (m, 1H), 3.44 (dd, J=16.7, 4.4 Hz, 1H), 3.09 (ddd, J=17.8, 5.4, 3.0 Hz, 1H), 2.75-2.61 (m, 2H), 2.49 (s, 3H), 2.48-2.42 (m, 1H), 1.83 (qd, J=11.9, 5.6 Hz, 1H).

Example 12: N-(2-chloro-4-methylbenzyl)-5,8-dimethoxy-1,2,3,4-tetrahydronaphthalen-2-amine 3-12

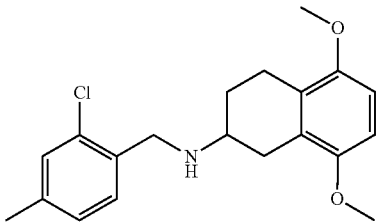 [SMILES: COc1ccc(OC)c2c1CCC(NCc1ccc(C)cc1Cl)C2]

The same procedure used for the preparation of 3-1 was applied to afford the title compound (35 mg, 30% yield) as a white solid after treatment with HCl in dioxane. LCMS: m/z 346 [M+H]+. ¹H NMR (400 MHz, Solvent: CD₃OD) 7.53 (d, J=7.8 Hz, 1H), 7.44 (s, 1H), 7.29 (d, J=7.7 Hz, 1H), 6.78 (s, 2H), 4.48 (s, 2H), 3.81 (s, 3H), 3.80 (s, 3H), 3.67-3.55 (m, 1H), 3.47-3.36 (m, 1H), 3.08 (ddd, J=17.8, 5.6, 3.3 Hz, 1H), 2.74-2.61 (m, 2H), 2.48-2.42 (m, 1H), 2.41 (s, 3H), 1.83 (ddd, J=23.9, 11.7, 5.6 Hz, 1H).

Example 13: N-(2-chloro-5-methylbenzyl)-5,8-dimethoxy-1,2,3,4-tetrahydronaphthalen-2-Amine (1-13)

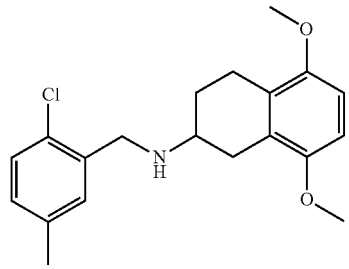 [SMILES: COc1ccc(OC)c2c1CCC(NCc1cc(C)ccc1Cl)C2]

The same procedure used for the preparation of 3-1 was applied to afford the title compound E (26 mg, 30% yield) as a white solid after treatment with HCl in dioxane. LCMS: (ES+): m/z 347.1 [M+H]+. ¹H NMR (400 MHz, MeOD) δ 7.50 (d, J=1.7 Hz, 1H), 7.46 (d, J=8.2 Hz, 1H), 7.32 (dd, J=8.2, 1.7 Hz, 1H), 6.78 (s, 2H), 4.49 (s, 2H), 3.81 (s, 3H), 3.80 (s, 3H), 3.66-3.58 (m, 1H), 3.43 (dd, J=16.5, 4.0 Hz, 1H), 3.08 (ddd, J=17.8, 5.5, 3.0 Hz, 1H), 2.74-2.63 (m, 2H), 2.50-2.39 (m, 4H), 1.84 (qd, J=11.9, 5.6 Hz, 1H).

Example 14: N-(2,4-dichlorobenzyl)-5,8-dimethoxy-1,2,3,4-tetrahydronaphthalen-2-amine (1-14)

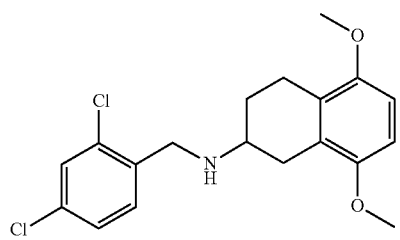 [SMILES: COc1ccc(OC)c2c1CCC(NCc1ccc(Cl)cc1Cl)C2]

The same procedure used for the preparation of 3-1 was applied to afford the title compound as a colorless oil (148 mg, 88%). LCMS: 2.465 min, m/z 368.00 [M+H]$^+$. $^1$H NMR (400 MHz, Methanol-d$_4$) δ 7.73-7.64 (m, 2H), 7.55-7.49 (m, 1H), 6.79 (s, 2H), 4.52 (s, 2H), 3.81 (s, 3H), 3.80 (s, 3H), 3.70-3.58 (m, 1H), 3.47-3.38 (m, 1H), 3.14-3.03 (m, 1H), 2.77-2.61 (m, 2H), 2.50-2.38 (m, 1H), 1.85 (tt, J=11.8, 5.9 Hz, 1H).

Example 15: N-(3,5-dichlorobenzyl)-5,8-dimethoxy-1,2,3,4-tetrahydronaphthalen-2-amine (1-15)

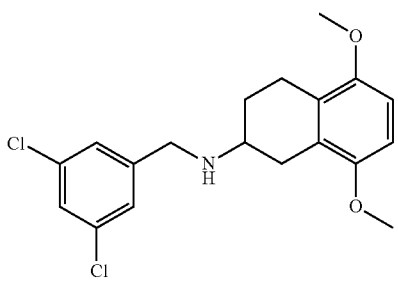 [SMILES: COc1ccc(OC)c2c1CCC(NCc1cc(Cl)cc(Cl)c1)C2]

The same procedure used for the preparation of 3-1 was applied to afford the title compound as a colorless oil (138 mg, 82%). LCMS: 2.458 min, m/z 366.15 [M+H]$^+$. $^1$H NMR (400 MHz, Methanol-d$_4$) δ 7.61 (s, 3H), 6.78 (s, 2H), 4.39 (s, 2H), 3.81 (s, 3H), 3.80 (s, 3H), 3.62-3.52 (m, 1H), 3.44-3.36 (m, 1H), 3.12-3.02 (m, 1H), 2.72-2.59 (m, 2H), 2.46-2.36 (m, 1H), 1.80 (qd, J=11.9, 5.5 Hz, 1H).

Example 16: N-(3,4-dichlorobenzyl)-5,8-dimethoxy-1,2,3,4-tetrahydronaphthalen-2-amine (1-16)

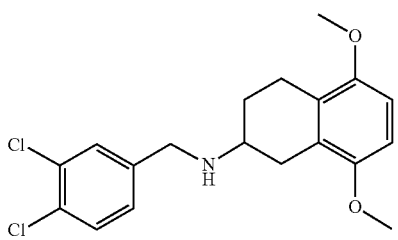 [SMILES: COc1ccc(OC)c2c1CCC(NCc1ccc(Cl)c(Cl)c1)C2]

The same procedure used for the preparation of 3-1 was applied to afford the title compound (20 mg, 20%) as a white solid after treatment with HCl in dioxane. LCMS: (ES$^+$): m/z 367.3 [M+H]$^+$. $^1$H NMR (400 MHz, MeOD) δ 7.79 (d, J=1.9 Hz, 1H), 7.66 (d, J=8.3 Hz, 1H), 7.50 (dd, J=8.3, 2.0 Hz, 1H), 6.76 (s, 2H), 4.37 (s, 2H), 3.79 (s, 3H), 3.78 (s, 3H), 3.61-3.50 (m, 1H), 3.37 (dd, J=16.7, 4.4 Hz, 1H), 3.10-3.00 (m, 1H), 2.71-2.58 (m, 2H), 2.44-2.35 (m, 1H), 1.79 (qd, J=11.8, 5.6 Hz, 1H).

Example 17: N-(2,3-dichlorobenzyl)-5,8-dimethoxy-1,2,3,4-tetrahydronaphthalen-2-amine (1-17)

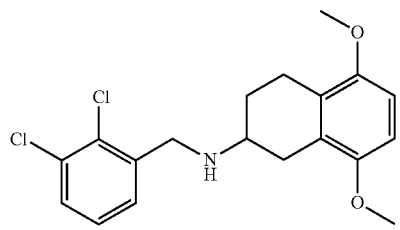 [SMILES: COc1ccc(OC)c2c1CCC(NCc1cccc(Cl)c1Cl)C2]

The same procedure used for the preparation of 3-1 was applied to afford the title compound as a colorless oil (111 mg, 66%). LCMS: m/z 367.65 [M+H]$^+$. $^1$H NMR (400 MHz, Methanol-d$_4$) δ 7.71 (dd, J=8.1, 1.5 Hz, 1H), 7.64 (dd, J=7.7, 1.5 Hz, 1H), 7.47 (t, J=7.9 Hz, 1H), 6.79 (s, 2H), 3.82 (s, 3H), 3.80 (s, 3H), 3.73-3.57 (m, 1H), 3.49-3.37 (m, 1H), 3.15-3.03 (m, 1H), 2.77-2.60 (m, 2H), 2.53-2.40 (m, 1H), 1.85 (qd, J=11.9, 5.5 Hz, 1H).

Example 18: N-benzyl-5,8-dimethoxy-1,2,3,4-tetrahydronaphthalen-2-amine (1-18)

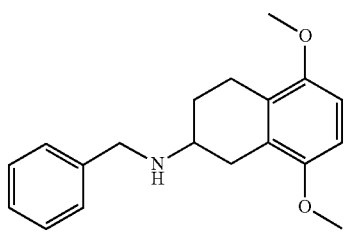 [SMILES: COc1ccc(OC)c2c1CCC(NCc1ccccc1)C2]

The same procedure used for the preparation of 3-1 was applied to afford the title compound as a colorless oil (3.93 g, 90%). LCMS: (ES−): m/z 298.6 [M+H]$^+$. $^1$H NMR (400 MHz, Methanol-d$_4$) δ 7.62-7.54 (m, 2H), 7.55-7.45 (m, 3H), 6.78 (s, 2H), 4.37 (s, 2H), 3.81 (s, 3H), 3.79 (s, 3H), 3.59-3.48 (m, 1H), 3.44-3.36 (m, 1H), 3.11-3.03 (m, 1H), 2.76-2.56 (m, 1H), 2.45-2.38 (m, 1H), 1.80 (qd, J=11.8, 5.6 Hz, 1H).

Example 19: N-(3-chloro-5-methylbenzyl)-5,8-dimethoxy-6-methyl-1,2,3,4-tetrahydro-naphthalen-2-amine hydrochloride (1-19)

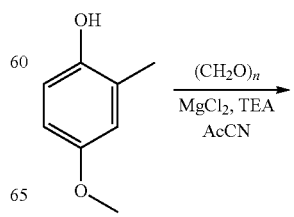

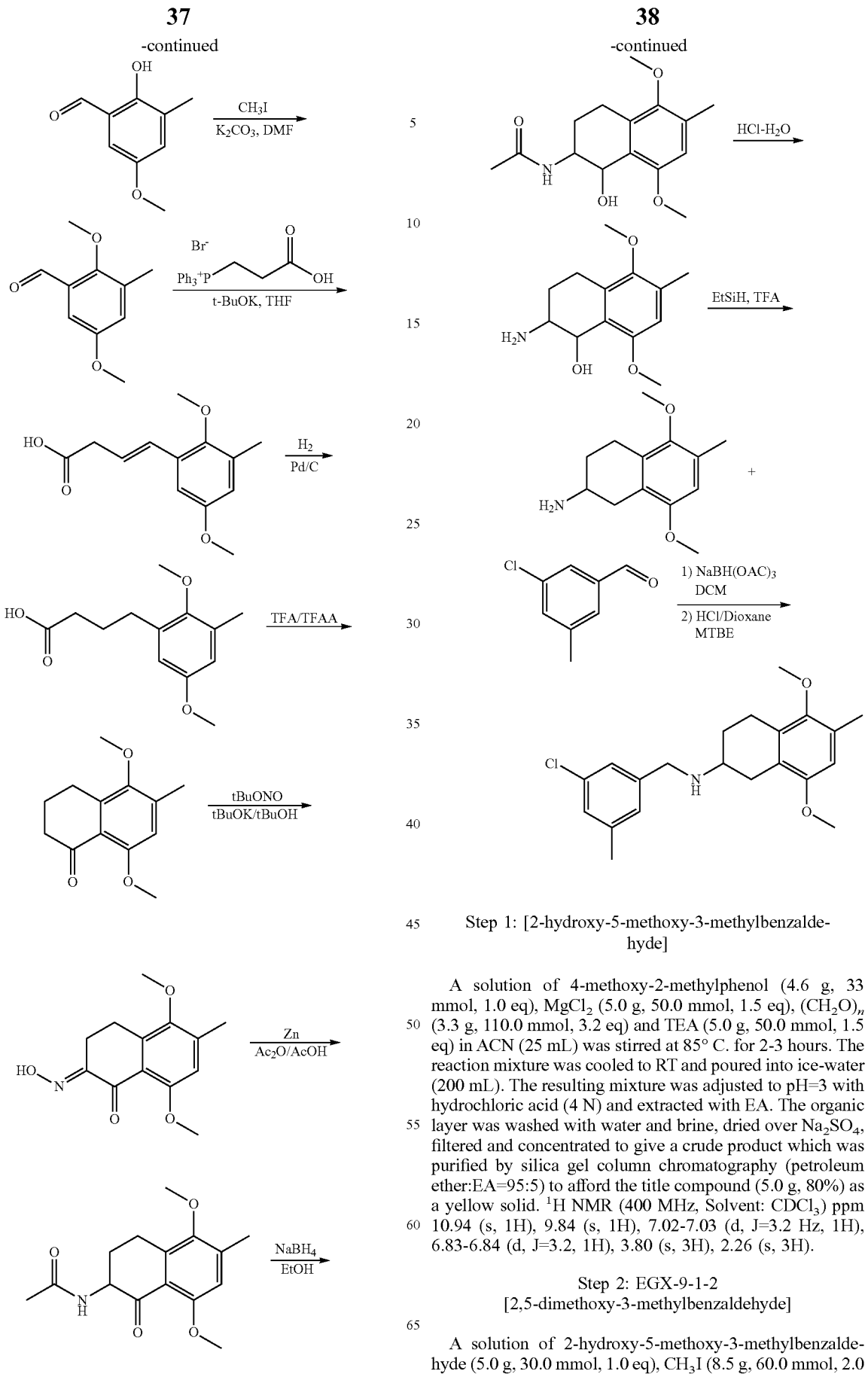

Step 1: [2-hydroxy-5-methoxy-3-methylbenzaldehyde]

A solution of 4-methoxy-2-methylphenol (4.6 g, 33 mmol, 1.0 eq), MgCl$_2$ (5.0 g, 50.0 mmol, 1.5 eq), (CH$_2$O)$_n$ (3.3 g, 110.0 mmol, 3.2 eq) and TEA (5.0 g, 50.0 mmol, 1.5 eq) in ACN (25 mL) was stirred at 85° C. for 2-3 hours. The reaction mixture was cooled to RT and poured into ice-water (200 mL). The resulting mixture was adjusted to pH=3 with hydrochloric acid (4 N) and extracted with EA. The organic layer was washed with water and brine, dried over Na$_2$SO$_4$, filtered and concentrated to give a crude product which was purified by silica gel column chromatography (petroleum ether:EA=95:5) to afford the title compound (5.0 g, 80%) as a yellow solid. $^1$H NMR (400 MHz, Solvent: CDCl$_3$) ppm 10.94 (s, 1H), 9.84 (s, 1H), 7.02-7.03 (d, J=3.2 Hz, 1H), 6.83-6.84 (d, J=3.2, 1H), 3.80 (s, 3H), 2.26 (s, 3H).

Step 2: EGX-9-1-2
[2,5-dimethoxy-3-methylbenzaldehyde]

A solution of 2-hydroxy-5-methoxy-3-methylbenzaldehyde (5.0 g, 30.0 mmol, 1.0 eq), CH$_3$I (8.5 g, 60.0 mmol, 2.0 eq) and K$_2$CO$_3$ (10.0 g) in DMF (20 mL) was stirred at RT overnight. TLC was monitored until the starting material was consumed. The reaction mixture was poured into water (30 mL) and extracted with MTBE (50 mL×3). The combined organic layers were washed with water (25 mL), brine (25 mL), dried over Na$_2$SO$_4$ and concentrated to give a crude product which was purified by silica gel column chromatography (petroleum ether:EA=95:5) to afford the title compound (5.2 g, 90%) as a yellow solid. $^1$H NMR (400 MHz, Solvent: CDCl$_3$) ppm 10.35 (s, 1H), 7.14-7.15 (d, J=3.2 Hz, 1H), 7.01-7.02 (d, J=3.2, 1H), 3.84 (s, 3H), 3.80 (s, 3H), 2.31 (s, 3H).

Step 3: (E)-4-(2,5-dimethoxy-3-methylphenyl)but-3-enoic acid

To a solution of 2,5-dimethoxy-3-methylbenzaldehyde (2.4 g, 13.3 mmol) in THF (40 mL) was added (2-carboxyethyl)triphenylphosphonium (8.3 g, 20 mmol, 1.5 eq) and t-BuOK solution in THF (40 mL, 40 mmol, 3 eq) at 0° C. The reaction mixture was stirred at room temperature overnight. The solvent was removed, the residue was diluted with water, basified with sodium hydroxide and extracted with EtOAc (50 mL). The aqueous phase was adjusted to pH=2 with hydrochloric acid solution and extracted with DCM (30 mL×3). The combined organic layers were washed with water (25 mL) and then brine (25 mL), dried over Na$_2$SO$_4$, filtered and concentrated to give a crude product (4.48 g) and was used in the next step without further purification.

Step 4: 4-(2,5-dimethoxy-3-methylphenyl)butanoic acid

To a solution of (E)-4-(2,5-dimethoxy-3-methylphenyl)but-3-enoic acid (4.48 g, 13.2 mmol) in MeOH (20 mL) was added Pd/C (250 mg) at room temperature. The reaction mixture was stirred at room temperature overnight. The suspension was filtered and the filtrate was concentrated to afford a crude product which was used in next step without further purification (3.88 g, 100%).

Step 5: 5,8-dimethoxy-6-methyl-3,4-dihydronaphthalen-1(2H)-one

To a solution of 4-(2,5-dimethoxy-3-methylphenyl)butanoic acid (3.88 g, 13.3 mmol) in TFA (10 mL) was added TFAA (8.5 mL, 66.6 mmol, 5 eq) at RT and the reaction mixture was stirred overnight. The reaction was diluted with EtOAc and washed with water (25 mL), brine (25 mL), dried over Na$_2$SO$_4$, filtered and concentrated to give a crude product which was purified by silica gel chromatography (petroleum ether:EtOAc=5:1) to afford the title compound as a colorless oil (1.2 g, 56%).

Step 6: (E)-2-(hydroxyimino)-5,8-dimethoxy-6-methyl-3,4-dihydronaphthalen-1(2H)-one To a solution of 5,8-dimethoxy-6-methyl-3,4-dihydronaphthalen-1(2H)-one (1.2 g, 5.45 mmol) in t-BuOH/Et$_2$O (10 mL/10 mL) was added t-BuOK (911 mg, 8.12 mmol, 1.5 eq) and tert-butyl nitrite (842.7 mg, 8.12 mmol, 1.5 eq) at room temperature. The reaction mixture was stirred overnight. The reaction was quenched with water (25 mL), adjusted to pH=2 with hydrochloric acid solution and extracted with DCM (30 mL×3). The combined organic layers were washed with water (25 mL), brine (25 mL), dried over Na$_2$SO$_4$, filtered and concentrated to give a crude product which was purified by silica gel chromatography (DCM:MeOH=100:1) to afford the title compound as a yellow solid (700 mg, 51%).

Step 7: N-(5,8-dimethoxy-6-methyl-1-oxo-1,2,3,4-tetrahydronaphthalen-2-yl)acetamide To a solution of (E)-2-(hydroxyimino)-5,8-dimethoxy-6-methyl-3,4-dihydronaphthalen-1(2H)-one (500 mg, 2.27 mmol, 1.3 eq) in AcOH (6 mL) was added Zn (445 mg, 6.81 mmol, 3 eq) and Ac$_2$O (4 mL) at room temperature under N$_2$. The reaction mixture was stirred at room temperature overnight. The suspension was filtered, the filtrate diluted with water, adjusted to pH=8 with sodium hydroxide (4 M in water) and extracted with EtOAc. The extract was washed with water (25 mL), brine (25 mL), dried over Na$_2$SO$_4$, filtered and concentrated to give a crude product which was purified by silica gel column chromatography (DCM:MeOH=100:1) to afford the title compound as a colorless oil (180 mg, 40%).

Step 8: N-(1-hydroxy-5,8-dimethoxy-6-methyl-1,2,3,4-tetrahydronaphthalen-2-yl)acetamide To a solution of N-(5,8-dimethoxy-6-methyl-1-oxo-1,2,3,4-tetrahydronaphthalen-2-yl)acetamide (184 mg, 0.664 mmol) in MeOH (10 mL) was added NaBH$_4$ (75.6 g, 2.0 mmol, 3 eq) at 0° C. The reaction mixture was stirred at room temperature overnight. The reaction was diluted with EtOAc, washed with water (25 mL), brine (25 mL), dried over Na$_2$SO$_4$, filtered and concentrated to give a crude product which was used in next step without further purification (203 mg, 100%).

Step 9: 2-amino-5,8-dimethoxy-6-methyl-1,2,3,4-tetrahydronaphthalen-1-ol

To a solution of N-(1-hydroxy-5,8-dimethoxy-6-methyl-1,2,3,4-tetrahydronaphthalen-2-yl)acetamide (158 mg, 0.565 mmol) in H$_2$O (5 mL) was added concentrated hydrochloric acid (12 M in water) (0.8 mL) at room temperature. The reaction mixture was stirred at reflux for 2 h, cooled to room temperature and adjusted to pH=8 with sodium hydroxide (4 M in water). The reaction mixture was extracted with EtOAc. The organic layer was washed with water (25 mL), brine (25 mL), dried over Na$_2$SO$_4$, filtered and concentrated to give a crude product which was used in next step without further purification (143 mg, 56%). $^1$H NMR (400 MHz, methanol-d$_4$) δ 6.74 (s, 1H), 5.03 (dd, J=3.7, 1.3 Hz, 1H), 3.85 (s, 3H), 3.69 (s, 3H), 3.38-3.34 (m, 1H), 3.16-3.10 (m, 1H), 2.76-2.67 (m, 1H), 2.30 (s, 3H), 2.14-2.04 (m, 1H), 1.99-1.92 (m, 1H).

Step 10: 5,8-dimethoxy-6-methyl-1,2,3,4-tetrahydronaphthalen-2-amine

To a solution of 2-amino-5,8-dimethoxy-6-methyl-1,2,3,4-tetrahydronaphthalen-1-ol (80 mg, 0.33 mmol) in TFA (6 mL) was added Et$_3$SiH (206 mg, 1.65 mmol, 5 eq) at room temperature and the reaction mixture was stirred. The reaction was diluted with water (25 mL), adjust to pH=10 with sodium hydroxide (4 M in water). The reaction mixture was extracted with EtOAc. The organic layer was washed with water and then brine (25 mL), dried over Na$_2$SO$_4$, filtered and concentrated to give a crude product which was purified by silica gel column chromatography (DCM:MeOH=100:1)

to afford the title compound as a colorless oil (64 mg, 86%). ¹H NMR (400 MHz, methanol-d₄) δ 6.65 (s, 1H), 3.80 (s, 3H), 3.69 (s, 3H), 3.50 (m, 1H), 3.19 (dd, J=17.2 Hz, 6.0 Hz, 1H), 3.06 (dt, J=17.5, 4.8 Hz, 1H), 2.81 (m, 1H), 2.53 (dd, J=16.8, 9.8 Hz, 1H), 2.28 (s, 3H), 2.25-2.14 (m, 1H), 1.90-1.65 (m, 1H).

Step 11: N-(3-chloro-5-methylbenzyl)-5,8-dimethoxy-6-methyl-1,2,3,4-tetrahydronaphthalen-2-amine To a solution of 3-chloro-5-methylbenzaldehyde (33.5 mg, 0.217 mmol, 1.2 eq) in DCM (5 mL) was added 5,8-dimethoxy-6-methyl-1,2,3,4-tetrahydronaphthalen-2-amine (38 mg, 0.18 mmol) and NaBH(OAc)₃ (137.8 mg, 0.65 mmol, 3 eq) at room temperature ands the reaction mixture was stirred overnight. The reaction was quenched with aqueous NaHCO₃ solution and extracted with EA (50 mL×3). The combined organic layers were washed with brine, dried over Na₂SO₄, filtered and concentrated to give a crude product which was purified by silica gel column chromatography (DCM:MeOH=100/1) to afford the title compound as a colorless oil (41 mg, 67%). LCMS: (ES-): m/z 360.4 [M+H]⁺.

Step 12: N-(3-chloro-5-methylbenzyl)-5,8-dimethoxy-6-methyl-1,2,3,4-tetrahydronaphthalen-2-amine hydrochloride To a solution of N-(3-chloro-5-methylbenzyl)-5,8-dimethoxy-6-methyl-1,2,3,4-tetrahydronaphthalen-2-amine (41 mg, 0.1 mmol) in MTBE (5 mL) was added 4M HCl in dioxane (0.1 mL, 0.4 mmol, 4 eq) at room temperature. The mixture was stirred at room temperature for 2 h. The suspension was filtered to afford the title compound as white solid (39 mg, 86%). LCMS: (ES-): m/z 360.4 [M+H]⁺. ¹H NMR (400 MHz, Methanol-d₄) δ 7.43 (s, 1H), 7.34 (d, J=7.9 Hz, 2H), 6.67 (s, 1H), 4.33 (s, 2H), 3.82 (s, 3H), 3.69 (s, 3H), 3.62-3.46 (m, 1H), 3.37-3.34 (m, 1H), 3.17-3.10 (m, 1H), 2.82-2.70 (m, 1H), 2.60 (dd, J=16.6, 10.4 Hz, 1H), 2.46-2.40 (m, 1H), 2.28 (s, 3H), 1.78 (qd, J=12.0, 5.3 Hz, 1H).

Example 20: N-(3-chloro-5-methylbenzyl)-4,7-dimethoxy-2,3-dihydro-1H-inden-2-amine hydrochloride (1-20)

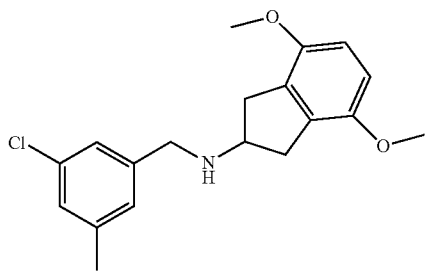 [SMILES: COc1ccc(OC)c2c1CC(NCc1cc(C)cc(Cl)c1)C2]

The same procedure as for the preparation of 1-19 was applied to afford the title compound as a white solid (153 mg, 81%). LCMS: (ES-): m/z 332.3 [M+H]⁺. ¹H NMR (400 MHz, solvent: CD₃OD) ppm 7.40 (s, 1H), 7.34 (s, 1H), 7.30 (s, 1H), 6.80 (s, 2H), 4.27 (s, 2H), 4.19-4.15 (m, 1H), 3.81 (s, 6H), 3.47-3.41 (m, 2H), 3.10 (d, J=6.0 Hz, 1H), 3.06 (d, J=6.0 Hz, 1H), 2.41 (s, 3H).

Example 21: N-(3-chloro-5-methylbenzyl)-4,7-dimethoxy-2,3-dihydro-1H-inden-1-amine (1-21)

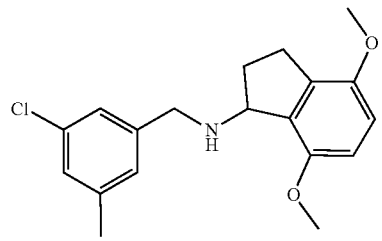 [SMILES: COc1ccc(OC)c2c1CCC2NCc1cc(C)cc(Cl)c1]

The same procedure as for the preparation of 1-19 was applied to afford the title compound as a colorless oil (174 mg, 78%). LCMS: (ES-): m/z 332.3 [M+H]⁺. ¹H NMR (400 MHz, solvent: CDCl₃) ppm 7.17 (s, 1H), 7.04 (d, J=4.8 Hz, 2H), 6.65 (dd, J=15.6 Hz, 8.8 Hz, 2H), 4.50 (dd, J=7.6 Hz, 4.4 Hz, 1H), 3.78 (d, J=5.2 Hz, 6H), 3.71 (dd, J=20.8 Hz, 13.2 Hz, 2H), 3.05-2.97 (m, 1H), 2.57-2.50 (m, 1H), 2.82-2.74 (m, 1H), 2.33-2.24 (m, 4H), 2.05-1.97 (m, 1H).

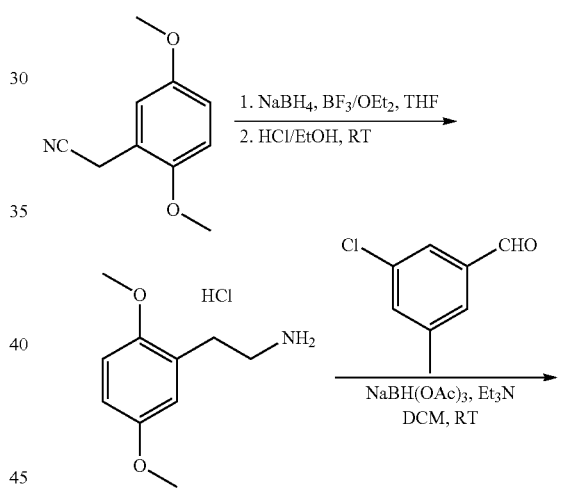

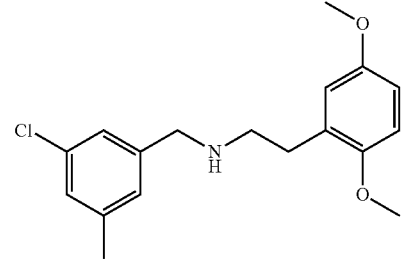

2-1

Example 22: Synthesis of N-(3-chloro-5-methylbenzyl)-2-(2,5-dimethoxyphenyl)ethan-1-amine (2-1)

Step 1: Preparation of 2-(2,5-dimethoxyphenyl)ethan-1-amine hydrochloride

A mixture of 2-(2,5-dimethoxyphenyl)acetonitrile (2.0 g, 11 mmol, 1.0 eq.) and NaBH₄ (1.24 g, 33 mmol, 3.0 eq.) in THF (30 ml) was stirred at 0° C. for 0.5 h, followed by addition of boron fluoride/ethyl ether (5.4 g, 38.5 mmol, 3.5 eq.); the resulting mixture was warmed to 50° C. and stirred overnight. TLC was monitored until the starting material was consumed. The reaction mixture was diluted with water (100 ml) and extracted with ethyl acetate (3×50 ml). The combined organic layers were dried over Na₂SO₄, and concentrated under reduced pressure to give a crude product which was purified by column chromatography (eluting with 5% MeOH in DCM gradient) to afford 2-(2,5-dimethoxyphenyl)ethan-1-amine hydrochloride (1.7 g, 85% yield) as a colorless oil. The free amine was converted to the HCl salt EGX-4-14-HCl (2.0 g, 90% yield) as a white solid after treatment with HCl in dioxane (4.0M). LCMS: (ES+): m/z 182 [M+H]⁺. ¹H NMR (400 MHz, DMSO-d6) ppm 8.10 (s, 2H), 6.90-6.92 (d, 1H), 6.79-9.61 (m, 2H), 3.74 (s, 3H), 3.70 (s, 3H), 2.93-2.97 (m, 2H), 2.81-2.85 (m, 2H).

Step 2: [N-(3-chloro-5-methylbenzyl)-2-(2,5-dimethoxyphenyl)ethan-1-amine]

A suspension of 2-(2,5-dimethoxyphenyl)ethan-1-amine hydrochloride (510 mg, 2.3 mmol, 1 eq), 3-chloro-5-methylbenzaldehyde (350 mg, 2.3 mmol, 1 eq), NaBH(OAc)₃ (2.44 g, 11.5 mmol, 5 eq), and TEA (0.35 g mg, 3.4 mmol, 1.5 eq) in DCM (5 ml) was stirred at RT overnight. The reaction was monitored by TLC until the reaction was completed. The resulting mixture was poured into water (15 ml), followed by addition of aqueous Na₂CO₃ solution to adjust to pH 9. The reaction mixture was extracted with ethyl acetate (3×10 ml). The combined organic layers were dried over Na₂SO₄ and concentrated under reduced pressure to give a crude product which was purified by column chromatography (eluting with 2% MeOH in a DCM gradient) to afford the compound 2-1 which was converted to the HCl salt (200 mg, 27% yield) as a white solid after treatment with HCl in dioxane (4.0 M). LMS: (ES+): m/z 320 [M+H]⁺. ¹H NMR (400 MHz, Solvent: CDCl₃) ppm 9.26 (s, 2H), 7.47 (s, 1H), 7.33-7.31 (d, 2H), 6.91-6.94 (d, 1H), 6.79-6.82 (m, 2H), 4.14 (s, 2H), 3.74 (s, 3H), 3.71 (s, 3H), 3.051-3.07 (m, 2H), 2.93-2.95 (m, 2H), 2.34 (s, 3H).

Example 23: Synthesis of 2-(2,5-dimethoxyphenyl)-N-(3-fluoro-5-methylbenzyl)ethan-1-amine (2-2)

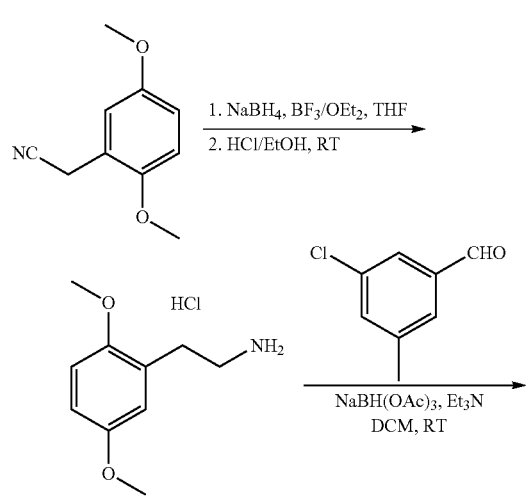

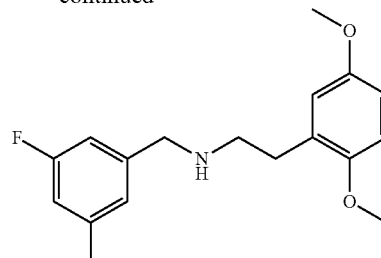

Step 1: 2-(2,5-dimethoxyphenyl)-N-(3-fluoro-5-methylbenzyl)ethan-1-amine

To a solution of 3-fluoro-5-methylbenzaldehyde (80 mg, 0.58 mmol) in DCM (5 mL) was added 2-(2,5-dimethoxyphenyl)ethan-1-amine hydrochloride (105 mg, 0.58 mmol, 1.0 eq), Et3N (110 mg) and NaBH(OAc)3 (368.9 mg, 1.74 mmol, 3 eq.) at room temperature. The resulting mixture was stirred at room temperature overnight. The reaction was quenched with aqueous NaHCO₃ solution, and then extracted with EA (3×50 mL). The combined organic layers were washed with brine, dried over Na₂SO₄, filtered and concentrated to give a crude product which was purified by silica gel column chromatography (DCM:MeOH=100/1) to afford the title compound as a colorless oil (94 mg, 54%). LCMS: (ES-): m/z 304.6 [M+H]+. tR=2.190 min;

Step 2: 2-(2,5-dimethoxyphenyl)-N-(3-fluoro-5-methylbenzyl)ethan-1-amine hydrochloride To a solution of 2-(2,5-dimethoxyphenyl)-N-(3-fluoro-5-methylbenzyl)ethan-1-amine (94 mg, 0.31 mmol) in MTBE (5 mL) was added 4M HCl in dioxane (0.2 mL) at room temperature. The reaction mixture was stirred at room temperature for 2 h. The suspension was filtered and dried to afford the title compound as white solid (93 mg, 89%). 1H NMR (400 MHz, Methanol-d4) δ 7.16 (s, 1H), 7.07 (t, J=9.6 Hz, 2H), 6.94 (d, J=8.6 Hz, 1H), 6.89-6.79 (m, 2H), 4.21 (s, 2H), 3.81 (s, 3H), 3.77 (s, 3H), 3.29-3.19 (m, 2H), 3.05-3.00 (m, 2H), 2.42 (s, 3H).

Example 24: Synthesis of N-(2-chloro-4-methylbenzyl)-2-(2,5-dimethoxyphenyl)ethan-1-amine 2-3)

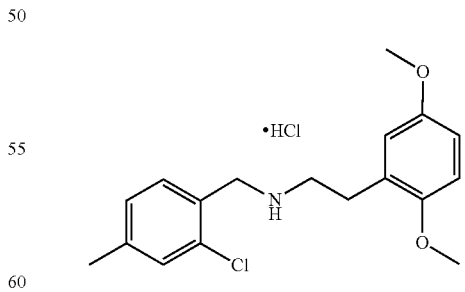

The same procedure used for the preparation of 2-2 was applied to afford the title compound EGX-2-3 which was converted to the HCl salt (60 mg, 42%) as a white solid after treatment with HCl in dioxane. LCMS: m/z 321[M+H]+. 1H NMR (400 MHz, solvent: DMSO) δ 9.38 (d, J=1.2 Hz, 2H), 7.62 (d, J=7.9 Hz, 1H), 7.40 (s, 1H), 7.26 (d, J=7.8 Hz, 1H), 6.96-6.88 (m, 1H), 6.84-6.77 (m, 2H), 4.25 (s, 2H), 3.73 (s, 3H), 3.70 (s, 3H), 3.13 (d, J=3.7 Hz, 2H), 2.97 (dd, J=9.8, 6.3 Hz, 2H), 2.33 (s, 3H).

Example 25: Synthesis of N-(2-chloro-5-methylbenzyl)-2-(2,5-dimethoxyphenyl)ethan-1-amine (2-4)

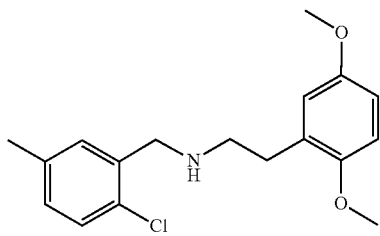 [SMILES: COc1ccc(OC)c(CCNCc2cc(C)ccc2Cl)c1]

The same procedure used for the preparation of 2-2 was applied to afford the title compound EGX-12-11 which was converted to the HCl salt (54 mg, 37% yield) as a white solid after treatment with HCl in dioxane. LCMS: m/z 320 [M+H]+. 1H NMR (400 MHz, solvent: DMSO) 9.40 (s, 2H), 7.58 (d, J=1.5 Hz, 1H), 7.44 (d, J=8.2 Hz, 1H), 7.28 (dd, J=8.2, 1.6 Hz, 1H), 6.93 (d, J=9.7 Hz, 1H), 6.82 (dd, J=5.9, 2.9 Hz, 2H), 4.25 (s, 2H), 3.74 (s, 3H), 3.71 (s, 3H), 3.14 (d, J=8.7 Hz, 2H), 2.98 (dd, J=9.8, 6.3 Hz, 2H), 2.33 (s, 3H).

Example 26: N-(2,4-dichlorobenzyl)-2-(2,5-dimethoxyphenyl)ethan-1-amine (2-5)

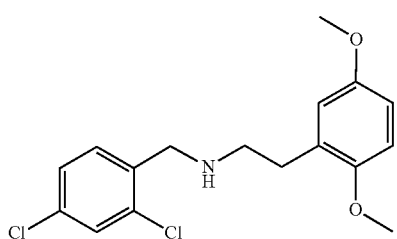 [SMILES: COc1ccc(OC)c(CCNCc2ccc(Cl)cc2Cl)c1]

The same procedure used for the preparation of 2-2 was applied to afford the title compound EGX-12-12 which was converted to the HCl salt (180 mg, 58%) as a white solid after treatment with HCl in dioxane. LCMS: m/z 341 [M+H]+. 1H NMR (400 MHz, solvent: DMSO) 9.42 (s, 2H), 7.80-7.75 (m, 2H), 7.58 (dd, J=8.3, 2.2 Hz, 1H), 6.96-6.90 (m, 1H), 6.82 (dd, J=7.3, 2.7 Hz, 2H), 4.29 (s, 2H), 3.74 (s, 3H), 3.70 (s, 3H), 3.21-3.12 (m, 2H), 2.96 (dd, J=9.6, 6.5 Hz, 2H).

Example 27: N-(3,5-dichlorobenzyl)-2-(2,5-dimethoxyphenyl)ethan-1-amine (2-6)

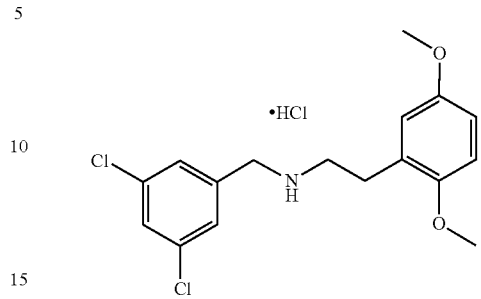

3.18 (m, 2H), 3.05-2.93 (m, 2H).

Example 28: N-(3,4-dichlorobenzyl)-2-(2,5-dimethoxyphenyl)ethan-1-amine (2-7)

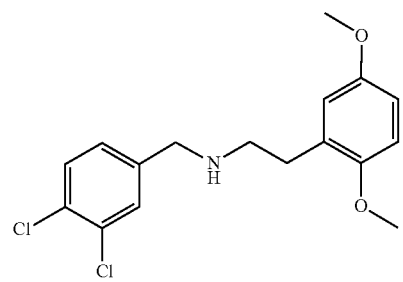 [SMILES: COc1ccc(OC)c(CCNCc2ccc(Cl)c(Cl)c2)c1]

The same procedure used for the preparation of 2-2 was applied to the title compound which was converted to the HCl salt (50 mg, 32%) as a white solid after treatment with HCl in dioxane. LCMS: m/z 341 [M+H]+. 1H NMR (400 MHz, solvent: DMSO) 9.49 (s, 2H), 7.91 (d, J=1.9 Hz, 1H), 7.72 (d, J=8.3 Hz, 1H), 7.58 (dd, J=8.3, 2.0 Hz, 1H), 6.92 (d, J=8.5 Hz, 1H), 6.81 (dd, J=11.8, 3.1 Hz, 2H), 4.19 (s, 2H), 3.73 (s, 3H), 3.70 (s, 3H), 3.12-3.02 (m, 2H), 2.99-2.90 (m, 2H).

Example 29: N-(2,3-dichlorobenzyl)-2-(2,5-dimethoxyphenyl)ethan-1-amine (2-8)

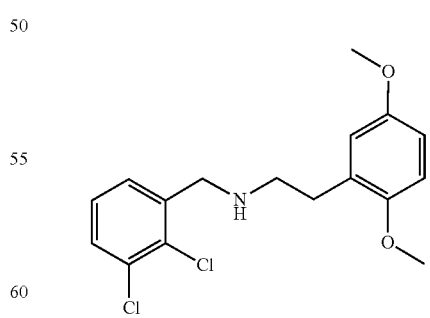

The same procedure used for the preparation of 2-2 was applied to afford the title compound which was converted to the HCl salt (185 mg, 64%) as a white solid after treatment with HCl in dioxane. LCMS: m/z 341[M+H]+. 1H NMR (400 MHz, solvent: DMSO) 9.61 (s, 2H), 7.80-7.69 (m, 2H), 7.48 (t, J=7.9 Hz, 1H), 6.97-6.90 (m, 1H), 6.81 (dd, J=7.2, 2.6 Hz, 2H), 4.35 (s, 2H), 3.74 (s, 3H), 3.70 (s, 3H), 3.18 (dd, J=9.7, 6.4 Hz, 2H), 2.99 (dd, J=9.7, 6.4 Hz, 2H).

Example 30: 2-(2,5-dimethoxyphenyl)-N-(3-methyl-5-nitrobenzyl)ethan-1-amine (2-9)

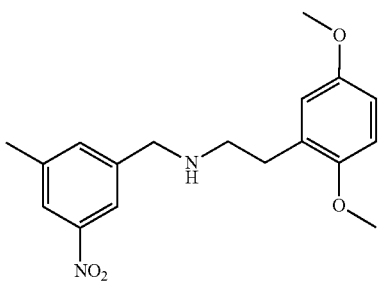 [SMILES: COc1ccc(OC)c(CCNCc2cc(C)cc([N+](=O)[O-])c2)c1]

The same procedure used for the preparation of 2-2 was applied to afford the title compound which was converted to the HCl salt (50 mg, 33%) as a white solid after treatment with HCl in dioxane. LCMS: m/z 331 [M+H]+. 1H NMR (400 MHz, solvent: DMSO) 9.40 (d, J=0.7 Hz, 1H), 8.30 (s, 1H), 8.13 (s, 1H), 7.85 (s, 1H), 6.92 (d, J=8.7 Hz, 1H), 6.86-6.75 (m, 2H), 4.29 (d, J=4.3 Hz, 2H), 3.73 (s, 3H), 3.70 (s, 3H), 3.10 (d, J=3.8 Hz, 2H), 2.99-2.90 (m, 2H), 2.47 (s, 3H).

Example 31: N-(3-bromo-5-methylbenzyl)-2-(2,5-dimethoxyphenyl)ethan-1-amine (2-10)

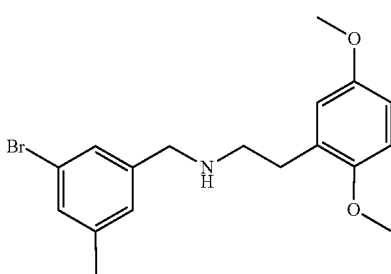 [SMILES: COc1ccc(OC)c(CCNCc2cc(C)cc(Br)c2)c1]

The same procedure used for the preparation of 2-2 was applied to afford the title compound as a colorless oil (45 mg, 31%) LCMS: (ES−): m/z 365.9 [M+H]+. tR=2.432 min; (40 mg, 80%). 1H NMR (400 MHz, Methanol-$d_4$) δ 7.50 (s, 2H), 7.29 (s, 1H), 6.94 (d, J=8.8 Hz, 1H), 6.89-6.79 (m, 2H), 4.19 (s, 2H), 3.82 (s, 3H), 3.77 (s, 3H), 3.29-3.21 (m, 2H), 3.06-2.99 (m, 2H), 2.40 (s, 3H).

Example 32: 2-(2,5-dimethoxyphenyl)-N-(3-iodo-5-methylbenzyl)ethan-1-amine (2-11)

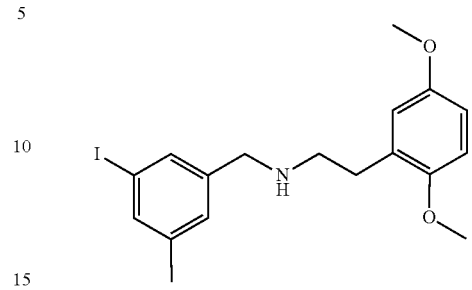

The same procedure used for the preparation of 2-2 was applied to afford the title compound as a white solid hydrochloride salt (40 mg, 80%). LCMS: (ES−): m/z 412.35 [M+H]+. $t_R$=2.419 min; 1H NMR (400 MHz, Methanol-$d_4$) δ 7.70 (s, 2H), 7.32 (s, 1H), 6.94 (d, J=8.8 Hz, 1H), 6.88-6.80 (m, 2H), 4.15 (s, 2H), 3.82 (s, 3H), 3.77 (s, 3H), 3.28-3.21 (m, 2H), 3.01 (d, J=8.3 Hz, 2H), 2.37 (s, 3H).

Example 33 N-(5-chloro-2-methylbenzyl)-2-(2,5-dimethoxyphenyl)ethan-1-amine (2-12

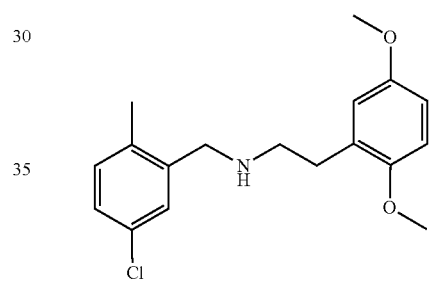

The same procedure used for the preparation of 2-2 was applied to afford the title compound which was converted to the HCl salt (80 mg, 62%) as a white solid after treatment with HCl in dioxane. LCMS: m/z 321 [M+H]+. 1H NMR (400 MHz, Solvent: DMSO) δ 9.39 (d, J=0.5 Hz, 2H), 7.66 (d, J=2.2 Hz, 1H), 7.37 (dd, J=8.2, 2.2 Hz, 1H), 7.29 (d, J=8.3 Hz, 1H), 6.97-6.90 (m, 1H), 6.86-6.78 (m, 2H), 4.16 (s, 2H), 3.75 (s, 3H), 3.71 (s, 3H), 3.17 (d, J=4.8 Hz, 2H), 3.00 (dd, J=10.0, 6.3 Hz, 2H), 2.37 (s, 3H).

Example 34: N-(3-chloro-4-methylbenzyl)-2-(2,5-dimethoxyphenyl)ethan-1-amine (2-13)

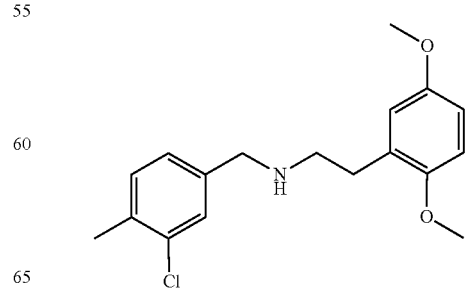

The same procedure used for the preparation of 2-2 which was converted to the HCl salt (80 mg, 61%) as a white solid after treatment with HCl in dioxane. LCMS: m/z 321 [M+H]⁺. ¹H NMR (400 MHz, Solvent: DMSO) 9.46 (s, 2H), 7.67 (d, J=1.1 Hz, 1H), 7.48-7.38 (m, 2H), 6.91 (d, J=8.7 Hz, 1H), 6.80 (dt, J=8.9, 3.0 Hz, 2H), 4.13 (s, 2H), 3.72 (s, 3H), 3.70 (s, 3H), 3.05 (d, J=19.6 Hz, 2H), 2.94 (dd, J=9.6, 5.2 Hz, 2H), 2.34 (s, 3H).

Example 35: N-(4-chloro-3-methylbenzyl)-2-(2,5-dimethoxyphenyl)ethan-1-amine (2-14)

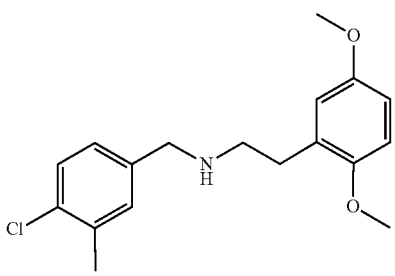 [SMILES: COc1ccc(OC)c(CCNCc2ccc(Cl)c(C)c2)c1]

The same procedure used for the preparation of 2-2 was applied to afford the title compound which was converted to the HCl salt EGX-12-6-HCl (80 mg, 61%) as a white solid after treatment with HCl in dioxane. LCMS: m/z 321 [M+H]+. 1H NMR (400 MHz, solvent: d6-DMSO) 9.37 (s, 1H), 7.54 (d, J=1.4 Hz, 1H), 7.49 (d, J=8.2 Hz, 1H), 7.41 (dd, J=8.2, 1.8 Hz, 1H), 6.92 (d, J=8.8 Hz, 1H), 6.80 (dt, J=7.1, 3.0 Hz, 2H), 4.12 (t, J=4.6 Hz, 2H), 3.72 (s, 3H), 3.70 (s, 3H), 3.12-3.00 (m, 2H), 2.93 (dd, J=9.8, 5.9 Hz, 2H), 2.34 (s, 3H).

Example 36: N-(3-chloro-2-methylbenzyl)-2-(2,5-dimethoxyphenyl)ethan-1-amine (2-15)

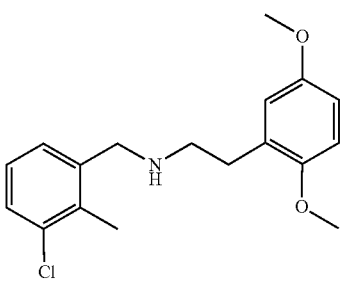 [SMILES: COc1ccc(OC)c(CCNCc2cccc(Cl)c2C)c1]

The same procedure used for the preparation of 2-2 was applied to afford the title compound which was converted to the HCl salt (82 mg, 62%) as a white solid after treatment with HCl in dioxane. LCMS: m/z 321 [M+H]⁺. ¹H NMR (400 MHz, solvent: DMSO) δ 9.35 (d, J=29.0 Hz, 2H), 7.51 (t, J=7.7 Hz, 2H), 7.30 (t, J=7.9 Hz, 1H), 6.93 (d, J=9.7 Hz, 1H), 6.82 (dd, J=6.6, 3.0 Hz, 2H), 4.25 (d, J=5.1 Hz, 2H), 3.75 (s, 3H), 3.71 (s, 3H), 3.17 (d, J=4.9 Hz, 2H), 2.98 (dd, J=9.8, 6.4 Hz, 2H), 2.43 (s, 3H).

Example 37: N-(2-chloro-3-methylbenzyl)-2-(2,5-dimethoxyphenyl)ethan-1-amine (2-16)

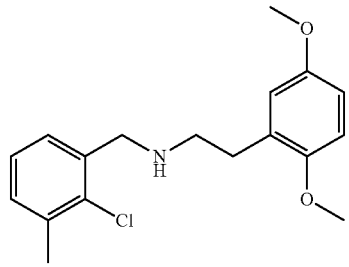 [SMILES: COc1ccc(OC)c(CCNCc2cccc(C)c2Cl)c1]

The same procedure used for the preparation of 2-2 was applied to afford the title compound which was converted to the HCl (80 mg, 61%) as a white solid after treatment with HCl in dioxane. LCMS: m/z 321 [M+H]⁺. ¹H NMR (400 MHz, solvent: DMSO) δ 9.43 (s, 1H), 7.58 (d, J=7.5 Hz, 1H), 7.44 (d, J=6.8 Hz, 1H), 7.34 (t, J=7.6 Hz, 1H), 6.96-6.89 (m, 1H), 6.84-6.78 (m, 2H), 4.31 (s, 2H), 3.74 (s, 3H), 3.70 (s, 3H), 3.21-3.11 (m, 2H), 2.98 (dd, J=9.9, 6.3 Hz, 2H), 2.38 (s, 3H).

Example 38: N-(4-chloro-2-methylbenzyl)-2-(2,5-dimethoxyphenyl)ethan-1-amine (2-17)

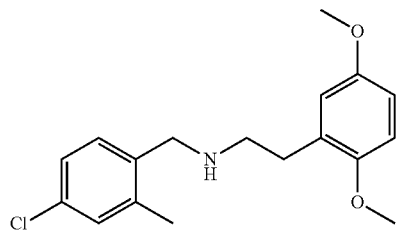

The same procedure used for the preparation of 2-2 was applied to afford the title compound which was converted to the HCl salt (80 mg, 61%) as a white solid after treatment with HCl in dioxane. LCMS: m/z 321 [M+H]⁺. ¹H NMR (400 MHz, solvent: DMSO) δ 9.31 (d, J=0.7 Hz, 2H), 7.56 (d, J=8.2 Hz, 1H), 7.37 (s, 1H), 7.37-7.33 (m, 1H), 6.96-6.90 (m, 1H), 6.82 (dd, J=6.3, 3.0 Hz, 2H), 4.15 (s, 2H), 3.74 (s, 3H), 3.70 (s, 3H), 3.15 (dd, J=1.6, 0.8 Hz, 2H), 2.98 (dd, J=9.8, 6.3 Hz, 2H), 2.40 (s, 3H).

Example 39: N-(3-chloro-5-methylbenzyl)-2-(2,5-dimethoxy-4-methylphenyl)ethan-1-amine (2-18)

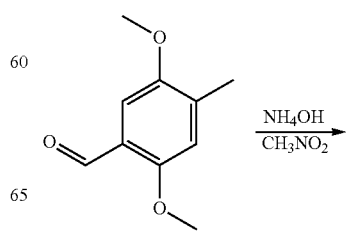

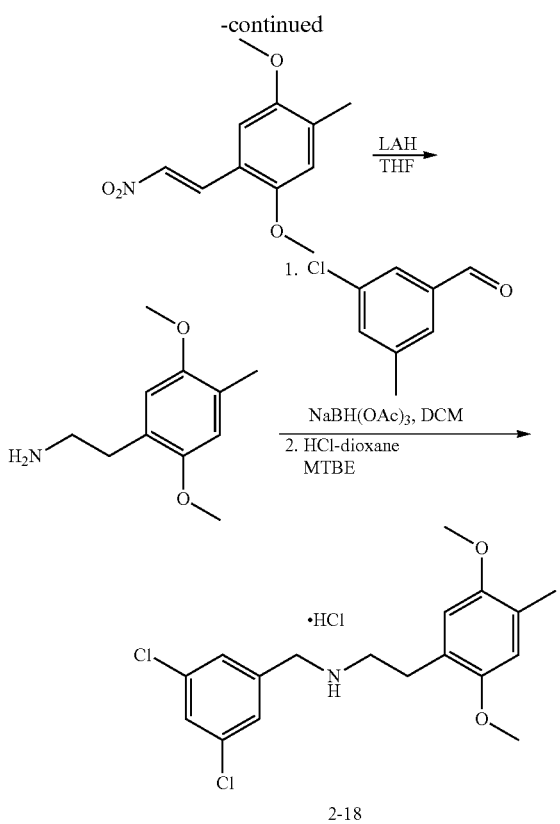

Step 1: 1,4-dimethoxy-2-methyl-5-(2-nitrovinyl)benzene

A suspension of 2,5-dimethoxy-4-methylbenzaldehyde (300 mg, 1.66 mmol, 2.5 eq) and ammonium acetate (51.3 mg, 0.67 mmol, 1 eq) in nitromethane (10 mL) was stirred at room temperature overnight. After the reaction was complete which was confirmed by TLC, some yellow solid appeared. Water and 5 mL EtOH were added and the mixture was stirred for 30 min at RT. The resulting yellow solid was filtered, washed by water (10 mL×3) and dried at 50° C. to afford the title compound (400 mg 100% yield) as a yellow solid. LCMS: 3.143 min, m/z 224.00 [M+H]$^+$

Step 2: 2-(2,5-dimethoxy-4-methylphenyl)ethan-1-amine

A suspension of LAH (190 mg, 5.01 mmol, 3 eq) in 5 mL THF was cooled to 0° C. under the protection of nitrogen, then 1,4-dimethoxy-2-methyl-5-(2-nitrovinyl)benzene (400 mg, 1.66 mmol, 1 eq) dissolved in 5 mL THF was added in. The resulting mixture was heated to reflux. After the reaction was complete which was confirmed by TLC, 2 mL water was added to quench the LAH. Na2CO3 was added to adjust the pH to 11. The resulting mixture was filtered and the filtrate was concentrated under reduced pressure to afford the crude product which was purified by flash chromatography (DCM/CH3OH=20) to afford the title compound (352 mg, 100%) as a colorless oil. LCMS: 1.872 min, m/z 196.30 [M+H]+. 1H NMR (400 MHz, Methanol-d4) δ 6.83 (s, 1H), 6.77 (s, 1H), 3.82 (s, 3H), 3.80 (s, 3H), 3.14 (t, J=7.4 Hz, 2H), 2.94 (t, J=7.4 Hz, 2H), 2.20 (s, 3H).

Step 3: EGX-15-2 N-(3-chloro-5-methylbenzyl)-2-(2,5-dimethoxy-4-methylphenyl)ethan-1-amine (2-28)

To a stirred solution of 2-(2,5-dimethoxy-4-methylphenyl)ethan-1-amine (150 mg, 0.77 mmol, 1.0 eq) and 3-chloro-5-methylbenzaldehyde (119 mg, 0.77 mmol, 1.0 eq) in dichloromethane (5 mL) was added NaBH(OAc)$_3$ (488 mg, 2.3 mmol, 3.0 eq). The resulting mixture was stirred at room temperature overnight. The reaction mixture was quenched with aqueous sodium bicarbonate solution and extracted with ethyl acetate. The organic layer was dried over anhydrous sodium sulfate and concentrated under reduced pressure to give a crude residue which was purified by flash chromatography (eluted with petroleum ether/ EA=1:1) to afford the title compound which was converted to the HCl salt EGX-15-1-HCl (100 mg, 35%) as a white solid after treatment with HCl in dioxane. LCMS: 2.637 min, m/z 333.95 [M+H]$^+$. $^1$H NMR (400 MHz, Methanol-d$_4$) δ 7.34 (s, 2H), 7.25 (s, 1H), 6.83 (s, 1H), 6.79 (s, 1H), 4.19 (s, 2H), 3.80 (s, 3H), 3.80 (s, 3H), 3.29-3.19 (m, 2H), 3.04-2.96 (m, 2H), 2.40 (s, 3H), 2.20 (s, 3H).

Example 40: N-(3-chloro-5-methylbenzyl)-2-(4-ethyl-2,5-dimethoxyphenyl)ethan-1-amine (2-19)

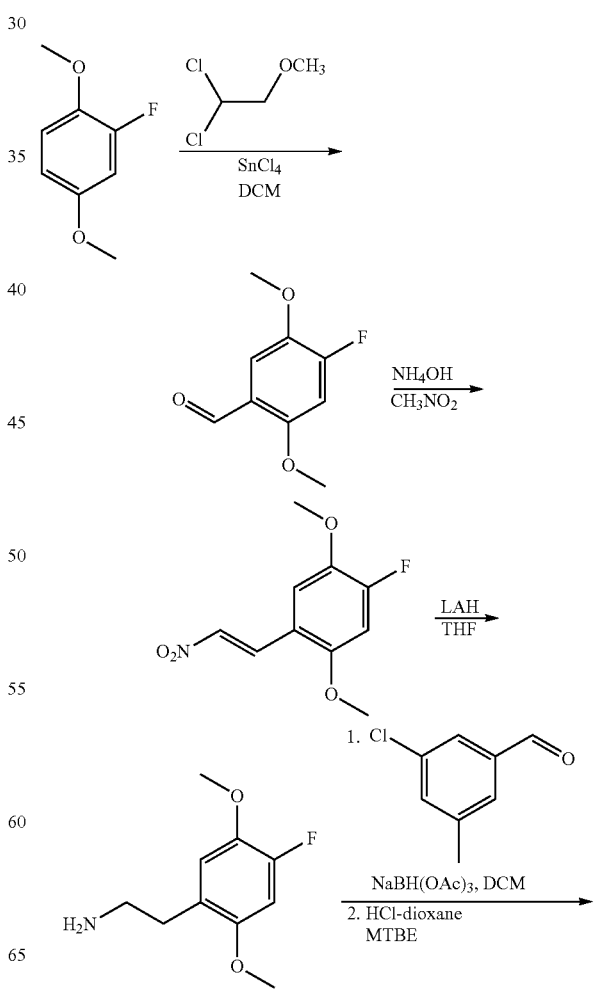

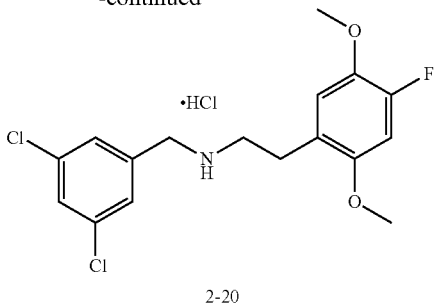

2-20

The same procedure used for the preparation of 2-18 was applied to afford the title compound which was converted to the HCl salt EGX-15-2-HCl (90 mg, 32% yield) as white solid after treatment with HCl in dioxane. LCMS: 2.730 min, m/z 348.25 [M+H]$^+$. $^1$H NMR (400 MHz, Methanol-d$_4$) δ 7.41-7.32 (m, 2H), 7.25 (s, 1H), 6.82 (d, J=7.9 Hz, 2H), 4.19 (s, 2H), 3.82 (s, 3H), 3.80 (s, 3H), 3.24 (dd, J=9.0, 6.4 Hz, 2H), 3.01 (dd, J=9.0, 6.4 Hz, 2H), 2.63 (q, J=7.5 Hz, 2H), 2.40 (s, 3H), 1.18 (t, J=7.5 Hz, 3H).

Example 41: N-(3-chloro-5-methylbenzyl)-2-(4-fluoro-2,5-dimethoxyphenyl)ethan-1-amine (2-20)

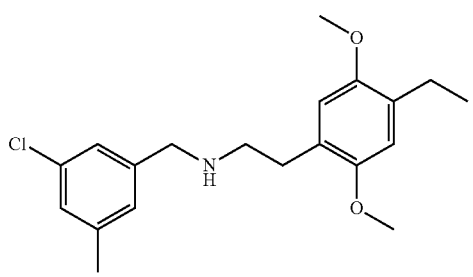

Step 1: 4-fluoro-2,5-dimethoxybenzaldehyde

To a solution of 2-fluoro-1,4-dimethoxybenzene (1 g, 6.41 mmol, 1 eq) in DCM (5 mL) was added dichloro(methoxy)methane (0.80 g, 7 mmol, 1.1 eq), followed by addition of SnCl4 (3.34 g, 12.82 mmol, 2 eq) at 0° C. The resulting mixture was stirred at room temperature overnight. The reaction was quenched with water and then extracted with EA (50 mL×3). The organic layer was washed with brine, dried over Na$_2$SO$_4$, filtered and concentrated to give a crude product which was purified via silica gel chromatography (eluted with petroleum ether/EA=1:1) to afford the title compound as a colorless oil. (1.36 g, 100%). LCMS: 2.602 min, m/z 185.10 [M+H]+.

Step 2: 1-fluoro-2,5-dimethoxy-4-(2-nitrovinyl)benzene

The same procedure used for the preparation of 2-18 was applied to afford the title compound EGX-15-5-2 (858 mg, 51%) as a yellow solid. LCMS: 2.963 min, m/z 491.20 [M+H]+

Step 3: 2-(4-fluoro-2,5-dimethoxyphenyl)ethan-1-amine hydrochloride

The same procedure used for the preparation of 2-18 was applied to afford the title compound which was converted to the HCl salt (328 mg, 79%) as a white solid after treatment with HCl in dioxane. LCMS: 1.435 min, m/z 200.30 [M+H]$^+$. $^1$H NMR (400 MHz, Methanol-d$_4$) δ 7.00 (d, J=9.4 Hz, 1H), 6.88 (d, J=13.0 Hz, 1H), 3.85 (s, 3H), 3.83 (s, 3H), 3.17-3.12 (m, 2H), 2.94 (t, J=7.4 Hz, 2H).

Step 4: N-(3-chloro-5-methylbenzyl)-2-(4-fluoro-2,5-dimethoxyphenyl)ethan-1-amine (2-20)

The same procedure used for the preparation of 2-18 was applied to afford the title compound which was converted to the HCl salt (136 mg, 57%) as a white solid after treatment with HCl in dioxane. LCMS: 2.417 min, m/z 338.35 [M+H]+.

Example 42: 2-(4-chloro-2,5-dimethoxyphenyl)-N-(3-chloro-5-methylbenzyl)ethan-1-amine (2-21)

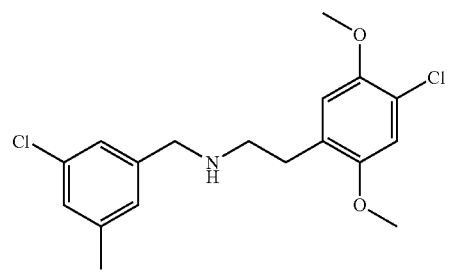 [SMILES: COc1cc(CCNCc2cc(C)cc(Cl)c2)c(OC)cc1Br]

The same procedure as for the preparation of 2-20 was applied to afford the title compound which was converted to the HCl salt (86 mg, 36%) as a white solid after treatment with HCl in dioxane. LCMS: 2.470 min, m/z 354.45 [M+H]$^+$. $^1$H NMR (400 MHz, Methanol-d$_4$) δ 7.36 (s, 1H), 7.35 (s, 1H), 7.26 (s, 1H), 7.07 (s, 1H), 6.99 (s, 1H), 4.21 (s, 2H), 3.86 (s, 3H), 3.83 (s, 3H), 3.30-3.22 (m, 2H), 3.07-2.99 (m, 2H), 2.42-2.36 (s, 3H).

Example 43: 2-(4-bromo-2,5-dimethoxyphenyl)-N-(3-chloro-5-methylbenzyl)ethan-1-amine (2-22)

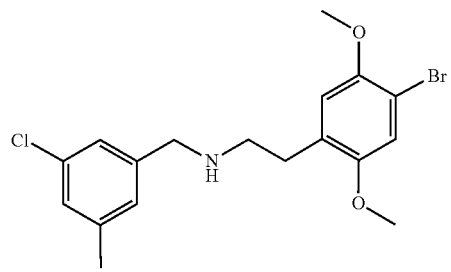

The same procedure as for the preparation of 2-18 was applied to afford the title compound which was converted to the HCl salt (40 mg, 35%) as a white solid after treatment with HCl in dioxane. LCMS: m/z 399.04[M+H]$^+$. $^1$H NMR (400 MHz, Solvent: DMSO) δ 9.33 (s, 2H), 7.48 (s, 1H), 7.33 (s, 2H), 7.21 (s, 1H), 7.02 (s, 1H), 4.13 (s, 2H), 3.80 (s, 3H), 3.76 (s, 3H), 3.14-3.02 (m, 2H), 3.01-2.92 (m, 2H), 2.33 (s, 3H).

Example 44 4-(2-((3-chloro-5-methylbenzyl)amino)ethyl)-2,5-dimethoxybenzonitrile (2-23)

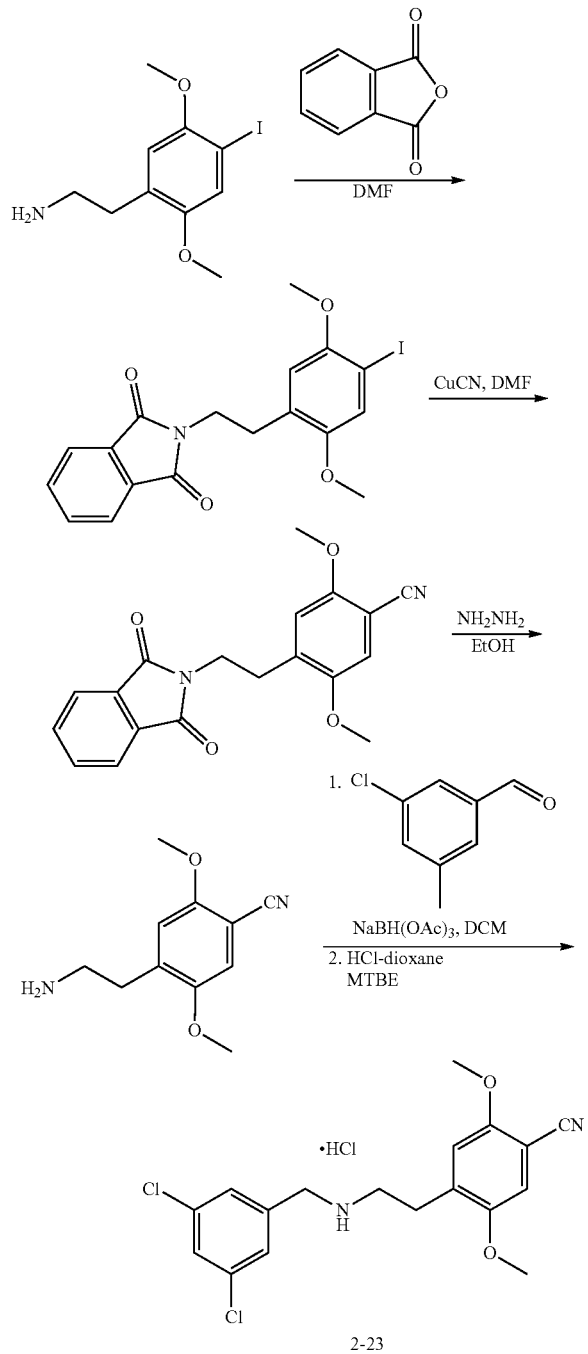

Step 1: 2-(4-iodo-2,5-dimethoxyphenethyl)isoindoline-1,3-dione

A suspension of 2-(4-iodo-2,5-dimethoxyphenyl)ethan-1-amine (1 g, 3.25 mmol, 1 eq) and phthalic anhydride (0.53 g, 3.58 mmol, 1.1 eq) in 3 mL DMF was heated to reflux overnight. After the reaction was completed as confirmed by TLC, 30 mL water was added and a white solid formed. The solid was filtered and washed with EtOH (5 mL×3) and petroleum ether (5 mL×3) to afford the title compound (1 g, 64%) as a white solid. 1H NMR (400 MHz, DMSO) δ 7.83 (d, J=1.2 Hz, 5H), 7.19 (s, 1H), 6.77 (s, 1H), 3.81 (t, 2H), 3.61 (s, 3H), 3.54 (s, 3H), 2.87 (t, 2H).

Step 2: 4-(2-(1,3-dioxoisoindolin-2-yl)ethyl)-2,5-dimethoxybenzonitrile

A suspension of 2-(4-iodo-2,5-dimethoxyphenethyl)isoindoline-1,3-dione (600 mg, 1.37 mmol, 1 eq) and copper cyanide (135 mg, 1.5 mmol, 1.1 eq) in 1.5 mL DMF was heated to reflux overnight. A solid formed as the reaction was cooled to RT. The solid was filtered and washed with petroleum ether (10 mL×3) to afford the title compound (550 mg, 89%) as a white solid. LCMS: m/z 337.05. $^1$H NMR (400 MHz, DMSO) δ 7.83 (s, 5H), 7.21 (s, 1H), 7.05 (s, 1H), 3.91-3.80 (t, 2H), 3.72 (s, 3H), 3.56 (s, 3H), 2.96 (t, J=6.5 Hz, 2H).

Step 3: 4-(2-aminoethyl)-2,5-dimethoxybenzonitrile

A suspension of 4-(2-(1,3-dioxoisoindolin-2-yl)ethyl)-2,5-dimethoxybenzonitrile (200 mg, 0.59 mmol, 1 eq) and hydrazine hydrate (59 mg, 1.48 mmol, 2.5 eq) in 5 mL EtOH was heated to reflux for 20 min. The solvent was evaporated in vacuo and the residue was purified by flash chromatography (eluted with DCM/CH3OH=20:1) to afford the title compound (35 mg, 28%). LCMS: m/z 207.24 [M+H]+. 1H NMR (400 MHz, CDCl3) δ 6.97 (s, 1H), 6.82 (s, 1H), 3.89 (s, 3H), 3.79 (s, 3H), 2.94 (s, 2H), 2.80 (t, J=6.9 Hz, 2H).

Step 4: 4-(2-((3-chloro-5-methylbenzyl)amino)ethyl)-2,5-dimethoxybenzonitrile (2-23)

The same procedure as for the preparation of 2-18 was applied to afford the title compound which was converted to the HCl salt EGX-15-8-HCl (20 mg, 34%) as a white solid after treatment with HCl in dioxane. LCMS: m/z 346.2[M+H]$^+$. $^1$H NMR (400 MHz, CDCl$_3$) δ 7.17 (s, 1H), 7.07 (s, 1H), 6.96 (s, 1H), 6.87 (s, 1H), 6.76 (s, 1H), 3.88 (s, 3H), 3.86 (s, 2H), 3.78 (s, 3H), 3.03 (d, J=8.3 Hz, 2H), 2.74-2.59 (m, 2H), 2.18 (s, 3H).

Example 45: N-(3-chloro-5-methylbenzyl)-2-(2,5-dimethoxy-4-(methylthio)phenyl)ethan-1-amine (2-24)

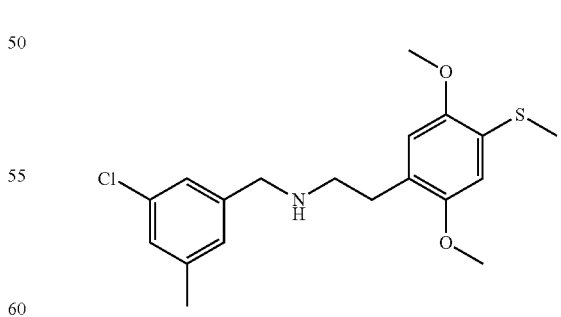

Step 1: 2,5-dimethoxy-4-(methylthio)benzaldehyde

The same procedures used for the preparation of 2-20 was applied to afford the title compound as a colorless oil. (1.45 g, 100%). LCMS: 2.717 min, m/z 213.30 [M+H]$^+$.

Step 2: EGX-15-10-2 (2,5-dimethoxy-4-(2-nitrovinyl)phenyl)(methyl)sulfane

The same procedures used for the preparation of 2-20 was applied to afford the title compound (385 mg, 22%) as a yellow solid. LCMS: 1.818 min, m/z 228.40 [M+H]$^+$.

Step 3: 2-(2,5-dimethoxy-4-(methylthio)phenyl)ethan-1-amine hydrochloride

The same procedures used for the preparation of 2-20 was applied to afford the title compound which was converted to the HCl salt (332 mg, 83%) as a white solid after treatment with HCl in dioxane. LCMS: m/z 212 [M+H]$^+$. $^1$NMR (400 MHz, CDCl$_3$) δ 6.74 (s, 1H), 6.52 (s, 1H), 3.88 (s, 3H), 3.83 (s, 3H), 3.80 (s, 3H), 3.00 (s, 2H), 2.80 (s, 2H).

Step 4: N-(3-chloro-5-methylbenzyl)-2-(2,5-dimethoxy-4-(methylthio)phenyl)ethan-1-amine The same procedures used for the preparation of 2-20 was applied to afford the title compound which was converted to the HCl salt (86 mg, 36%) as a white solid after treatment with HCl in dioxane. LCMS: 2.483 min, m/z 366.35 [M+H]$^+$. $^1$H NMR (400 MHz, Methanol-d$_4$) δ 7.40-7.31 (m, 2H), 7.25 (s, 1H), 6.84 (d, J=5.6 Hz, 2H), 4.20 (s, 2H), 3.86 (s, 3H), 3.84 (s, 3H), 3.29-3.21 (m, 2H), 3.05-2.97 (m, 2H), 2.44 (s, 3H), 2.41 (s, 3H).

Example 46: N-(3-chloro-5-methylbenzyl)-2-(2,5-dimethoxy-4-(methylsulfinyl)phenyl)-ethan-1-amine (2-25)

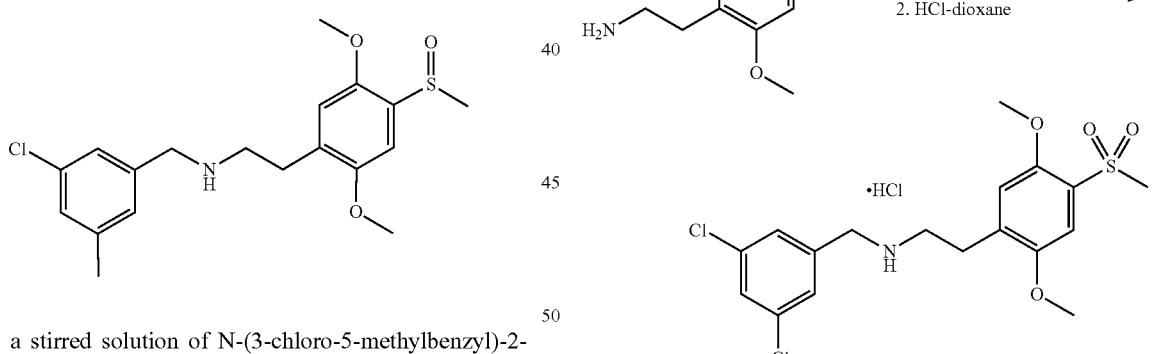

To a stirred solution of N-(3-chloro-5-methylbenzyl)-2-(2,5-dimethoxy-4-(methylthio)phenyl)ethan-1-amine (2-24 (50 mg, 0.14 mmol, 1.0 eq) in dichloromethane (5 mL) was added m-CPBA (28 mg, 0.14 mmol, 1.0 eq) at 0° C. The resulting mixture was stirred at room temperature overnight. The reaction mixture was quenched with aqueous Na2S2O4, and extracted with ethyl acetate; the combined organic layer was dried over anhydrous sodium sulfate, and concentrated under reduced pressure to give a crude residue which was purified by flash chromatography (eluted with petroleum ether/EA=1:1) to afford the title compound which was converted to the HCl salt (40 mg, 42%) as a white solid after treatment with HCl in dioxane. LCMS: 2.192 min, m/z 382.25 [M+H]+. 1H NMR (400 MHz, Methanol-d4) δ 7.38-7.33 (m, 3H), 7.29-7.23 (m, 1H), 7.05 (s, 1H), 4.22 (s, 2H), 3.92 (s, 3H), 3.90 (s, 3H), 3.32-3.26 (m, 2H), 3.14-3.07 (m, 2H), 2.81 (s, 3H), 2.41 (s, 3H).

Example 47: (3-chloro-5-methylbenzyl)-2-(2,5-dimethoxy-4-(methylsulfonyl)phenyl)ethan-1-amine (2-26)

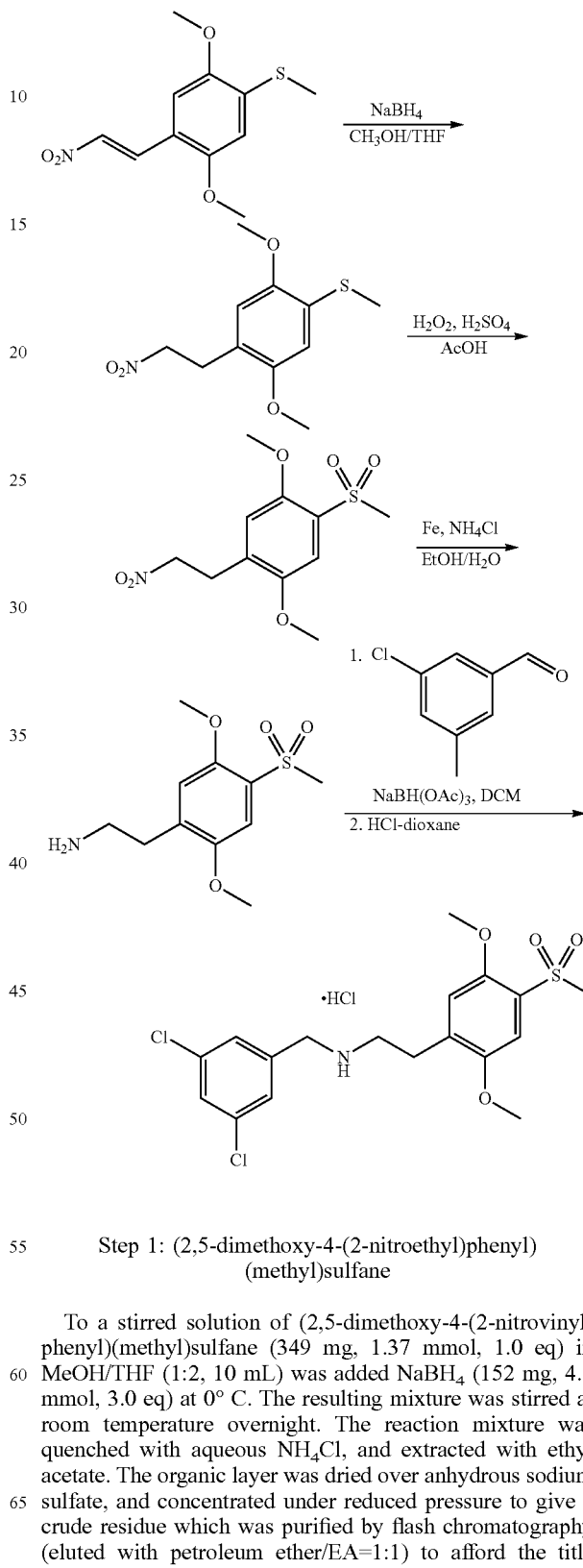

Step 1: (2,5-dimethoxy-4-(2-nitroethyl)phenyl)(methyl)sulfane

To a stirred solution of (2,5-dimethoxy-4-(2-nitrovinyl)phenyl)(methyl)sulfane (349 mg, 1.37 mmol, 1.0 eq) in MeOH/THF (1:2, 10 mL) was added NaBH$_4$ (152 mg, 4.1 mmol, 3.0 eq) at 0° C. The resulting mixture was stirred at room temperature overnight. The reaction mixture was quenched with aqueous NH$_4$Cl, and extracted with ethyl acetate. The organic layer was dried over anhydrous sodium sulfate, and concentrated under reduced pressure to give a crude residue which was purified by flash chromatography (eluted with petroleum ether/EA=1:1) to afford the title compound (216 mg, 62%) as a yellow oil. $^1$H NMR (400 MHz, Chloroform-d) δ 6.74 (s, 1H), 6.66 (s, 1H), 4.59 (t, J=7.2 Hz, 2H), 3.27 (t, J=7.2 Hz, 2H), 2.44 (s, 3H).

Step 2 1,4-dimethoxy-2-(methylsulfonyl)-5-(2-nitroethyl)benzene

To a stirred solution of (2,5-dimethoxy-4-(2-nitroethyl) phenyl)(methyl)sulfane (100 mg, 0.39 mmol, 1.0 eq) in AcOH (2 mL) was added $H_2O_2$ (132 mg, 1.17 mmol, 3.0 eq) and $H_2SO_4$ (1 drop) at 0° C. The resulting mixture was stirred at 75° C. overnight. The reaction mixture was diluted with water and extracted with ethyl acetate. The combined organic layer was dried over anhydrous sodium sulfate and concentrated under reduced pressure to give a crude residue which was purified by flash chromatography (eluted with petroleum ether/EA=1:1) to afford the title compound (110 mg, 98%) as a colorless oil. $^1$H NMR (400 MHz, chloroform-d) δ 7.47 (s, 1H), 6.90 (s, 1H), 4.64 (t, J=6.9 Hz, 2H), 3.95 (s, 3H), 3.88 (s, 3H), 3.34 (t, J=6.9 Hz, 2H), 3.22 (s, 3H).

Step 3 2-(2,5-dimethoxy-4-(methylsulfonyl)phenyl)ethan-1-amine

To a stirred solution of 1,4-dimethoxy-2-(methylsulfonyl)-5-(2-nitroethyl)benzene (110 mg, 0.39 mmol, 1.0 eq) in EtOH/$H_2O$ (2.5/1 mL) was added Fe (65 mg, 1.17 mmol, 3.0 eq) and $NH_4Cl$ (65 mg, 1.17 mmol, 3.0 eq) at room temperature. The resulting mixture was stirred at reflux overnight. The reaction mixture was filtered and the filtrate was concentrated under reduced pressure to give a crude residue which was purified by flash chromatography (eluted with MeOH/DCM=1:100) to afford the title compound (104 mg, 100%) as a colorless oil. $^1$H NMR (400 MHz, Chloroform-d) δ 7.43 (s, 1H), 6.89 (s, 1H), 3.95 (s, 3H), 3.84 (s, 3H), 3.22 (s, 3H), 2.95 (t, J=6.9 Hz, 2H), 2.81 (t, J=6.9 Hz, 2H).

Step 4: (3-chloro-5-methylbenzyl)-2-(2,5-dimethoxy-4-(methylsulfonyl)phenyl)ethan-1-amine The same procedure as for the preparation of 2-2 was applied to afford the title compound which was converted to the HCl salt (35 mg, 20%) as white solid after treatment with HCl in dioxane. LCMS: 2.112 min, m/z 398.35 [M+H]$^+$. $^1$H NMR (400 MHz, Methanol-d$_4$) δ 7.46 (s, 1H), 7.35 (s, 1H), 7.32 (s, 1H), 7.26 (s, 1H), 7.19 (s, 1H), 4.20 (s, 2H), 3.97 (s, 3H), 3.88 (s, 3H), 3.30-3.26 (m, 2H), 3.22 (s, 3H), 3.17-3.05 (m, 2H), 2.39 (s, 3H).

Example 48 N-(3-chloro-5-methylbenzyl)-2-(2,5-dimethoxy-4-methylphenyl)propan-1-amine (2-27)

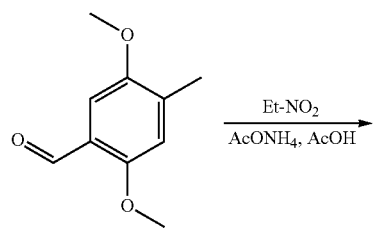

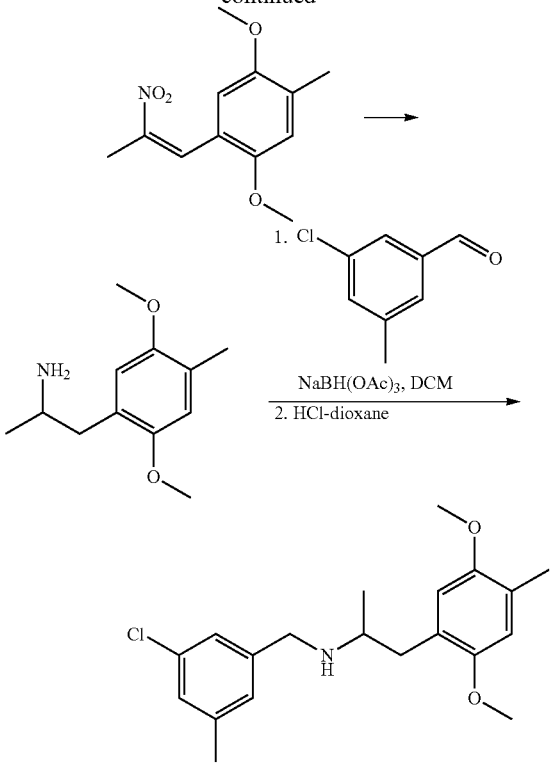

Step 1: 1,4-dimethoxy-2-methyl-5-(2-nitroprop-1-en-1-yl)benzene

A suspension of 2,5-dimethoxy-4-methylbenzaldehyde (3 g, 17 mmol, 1 eq), nitroethane (3.12 g, 42 mmol, 2.5 eq) and $NH_4OAc$ (6.4 g, 83 mmol, 5 eq) in 30 mL AcOH, was stirred at 80° C. overnight. The reaction was monitored by TLC until the reaction was complete. The resulting mixture was poured into water (20 mL). A yellow solid formed which was filtered and recrystallized from EtOH to afford the title compound (0.84 g, 21%) as a yellow solid. $^1$HNMR (400 MHz, CDCl$_3$): ppm 8.28 (s, 1H), 6.76 (s, 1H), 6.75 (s, 1H), 3.83 (s, 3H), 3.80 (s, 3H), 2.41 (s, 3H), 2.27 (s, 3H).

Step 2: 1-(2,5-dimethoxy-4-methylphenyl)propan-2-amine 1,4-dimethoxy-2-methyl-5-(2-nitroprop-1-en-1-yl)benzene (300 mg, 1 eq) dissolved in THF (5 mL) was added dropwise to a suspension of LiAlH$_4$ (192 mg, 4 eq) in THF (4 mL) at 0° C. The reaction was stirred at 0° C. for another 30 min. Water (1 mL) was added to quench the reaction, followed by the addition of NaOH/$H_2O$ (3 mL). The resulting mixture was extracted with DCM (5 mL×3). The combined organic layers were dried over $Na_2SO_4$ and concentrated under reduced pressure to afford the crude product which was purified by column chromatography (eluting with DCM/MeOH=10:1) afford the title compound (94 mg, 34%) as a brown oil. LC_MS: (ES+): m/z 210[M+H]$^+$. $^1$H NMR (400 MHz, solvent: CDCl$_3$) ppm 6.68 (s, 1H), 6.64 (s, 1H), 3.78 (s, 3H), 3.76 (s, 3H), 3.27-3.22 (m, 1H), 2.75-2.71 (m, 1H), 2.60-2.54 (m, 1H), 1.15 (d, J=8.0 Hz, 3H).

Step 3: N-(3-chloro-5-methylbenzyl)-2-(2,5-dimethoxy-4-methylphenyl)propan-2-amine The same procedure as for the preparation of 2-2 was applied to afford the title compound as a colorless oil. The free amine was converted to its HCl salt (30 mg, 64%) as a white solid after treatment with HCl in dioxane. LCMS: (ES+): m/z 348[M+H]$^+$. $^1$H NMR (400 MHz, solvent: CDCl$_3$) ppm 7.35 (s, 1H), 7.33 (s, 1H), 7.25 (s, 1H), 6.84 (s, 1H), 6.77 (s, 1H), 4.29-4.21 (m, 2H), 3.80 (s, 3H), 3.79 (s, 3H), 3.62-3.57 (m, 1H), 3.22-3.18 (m, 1H), 2.83-2.77 (m, 1H), 2.40 (s, 3H), 2.21 (s, 1H), 1.31 (d, J=8.0 Hz, 3H).

Example 49: N-(3-chloro-5-methylbenzyl)-2-(2,5-dimethoxy-3-methylphenyl)propan-2-amine 2-28

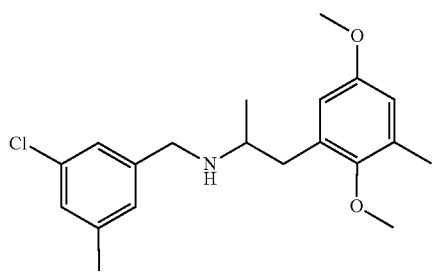 [SMILES: COc1cc(C)c(OC)c(CC(C)NCc2cc(C)cc(Cl)c2)c1]

The same procedure as for the preparation of 2-27 was applied to afford the title compound as a colorless oil. The free amine was converted to its HCl salt (20 mg, 44%) as a white solid after treatment with HCl in dioxane. LCMS: (ES+): m/z 348 [M+H]$^+$. $^1$H NMR (400 MHz, solvent: CDCl$_3$) ppm 7.38 (s, 1H), 7.35 (s, 1H), 7.12 (s, 1H), 6.62 (s, 1H), 6.54 (s, 1H), 4.06-3.93 (m, 2H), 3.75 (s, 3H), 3.60 (s, 3H), 3.45-3.37 (m, 2H), 2.83-2.77 (m, 1H), 2.32 (s, 3H), 2.24 (s, 3H), 1.34 (d, J=8.0 Hz, 3H).

Example 50: 2-((3-chloro-5-methylbenzyl)amino)-3-(2,5-dimethoxyphenyl)propan-1-ol (2-29)

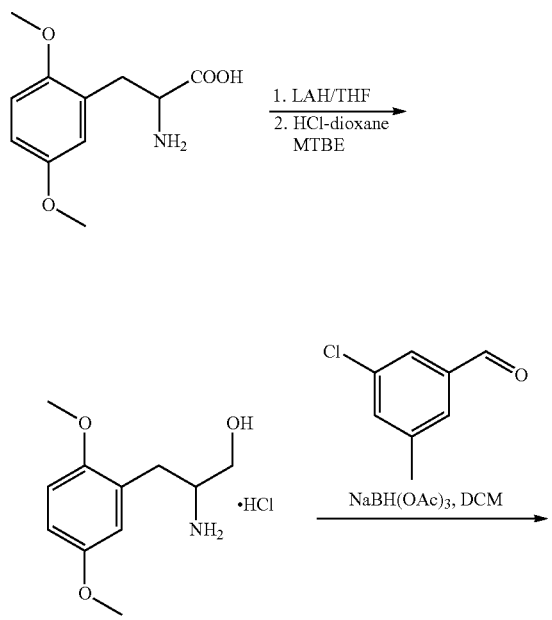

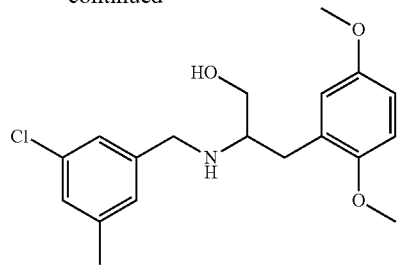

Step 1: 2-amino-3-(2,5-dimethoxyphenyl)propan-1-ol

To a solution of 2-amino-3-(2,5-dimethoxyphenyl)propanoic acid (500 mg, 2.22 mmol, 1 eq) in THF (20 mL) was added LAH (337 mg, 9 mmol, 4 eq). The resulting mixture was stirred at for 16 h. LCMS indicated the reaction was complete. The reaction was quenched with water and NaOH. The resulting mixture was filtered and washed with EA. The organic phase was collected and concentrated under reduced pressure to afford a crude product which was purified by flash chromatography to afford the title compound as an oil (190 mg, 40%).

Step 2: 2-amino-3-(2,5-dimethoxyphenyl)propan-1-ol hydrochloride

To a solution of 2-amino-3-(2,5-dimethoxyphenyl)propan-1-ol (190 mg, 1 eq) in MTBE (10 mL) was added 4 M HCl in dioxane (2 mL, >10 eq). The resulting white solid was filtered and washed by MTBE to afford the title compound (180 mg, 90%).

Step 3: 2-((3-chloro-5-methylbenzyl)amino)-3-(2,5-dimethoxyphenyl)propan-1-ol To a solution of 3-chloro-5-methylbenzaldehyde (112 mg, 0.72 mmol, 1 eq) in DCM (5 mL) was added 2-amino-3-(2,5-dimethoxyphenyl)propan-1-ol hydrochloride (180 mg, 0.72 mmol, 1 eq), TEA (218 mg, 2.16 mmol, 3 eq) and NaBH(OAc)$_3$ (440 mg, 2.16 mmol, 3 eq) and resulting mixture was stirred at room temperature overnight. The reaction was quenched with aqueous NaHCO$_3$ solution and extracted with EA (50 mL×3). The combined organic layers were washed with brine, dried over Na$_2$SO$_4$, filtered and concentrated to give a crude product which was purified by silica gel chromatography (DCM:MeOH=100/1) to afford the title compound as a colorless oil (98 mg, 44%). LCMS: m/z 351.00[M+H]$^+$. $^1$H NMR (400 MHz, MeOD) δ 7.08 (s, 1H), 7.04 (s, 1H), 6.94 (s, 1H), 6.87 (d, J=8.8 Hz, 1H), 6.78 (dd, J=8.8, 3.0 Hz, 1H), 6.73 (d, J=3.0 Hz, 1H), 3.74 (m, 8H), 3.53 (dd, J=11.1, 4.7 Hz, 1H), 3.45 (dd, J=11.1, 6.5 Hz, 1H), 2.93-2.86 (m, 1H), 2.79 (dd, J=13.1, 6.7 Hz, 1H), 2.65 (dd, J=13.1, 6.9 Hz, 1H), 2.31 (s, 3H).

Example 51 2-((3-chloro-5-methylbenzyl)amino)-1-(2,5-dimethoxyphenyl)ethan-1-ol (2-30)

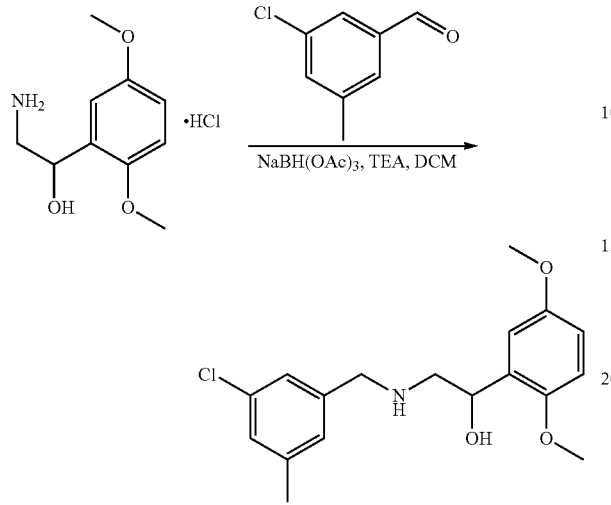

The same procedure as for the preparation of 2-29 was applied to afford the target which was treated with 4 M HCl in dioxane to obtained the title compound as a white solid (57 mg, 73%).

1H NMR (400 MHz, MeOD) δ 7.38 (s, 1H), 7.34 (s, 1H), 7.27 (s, 1H), 7.15 (d, J=3.0 Hz, 1H), 6.93 (d, J=8.9 Hz, 1H), 6.87 (dd, J=8.9, 3.0 Hz, 1H), 5.28 (dd, J=9.5, 2.9 Hz, 1H), 4.24 (s, 2H), 3.79 (d, J=1.7 Hz, 6H), 3.28 (dd, J=12.5, 2.9 Hz, 1H), 2.98 (dd, J=12.5, 9.6 Hz, 1H), 2.41 (s, 3H). LCMS: m/z 336.95[M+H]+

Example 52: N-(3-chloro-5-methylbenzyl)-2-(2,5-dimethoxy-4-morpholinophenyl)ethan-1-amine (2-31)

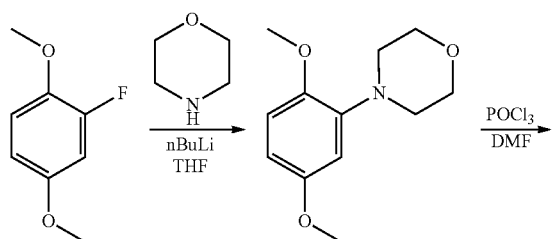

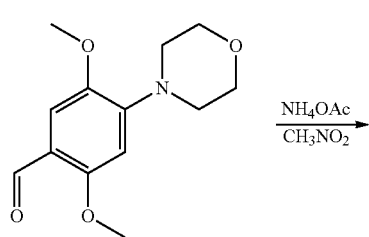

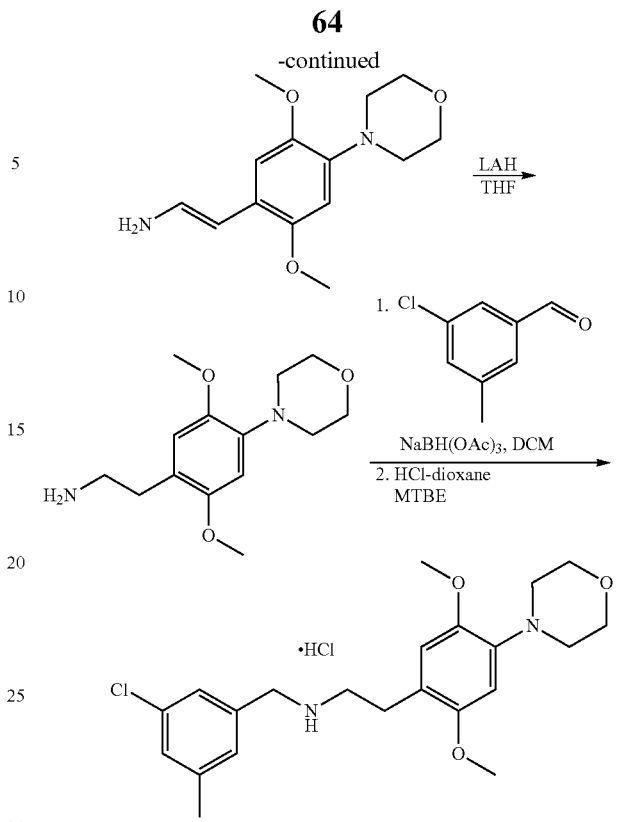

Step 1: 4-(2,5-dimethoxyphenyl)morpholine

To a solution of 2-fluoro-1,4-dimethoxybenzene (733 mg, 4.7 mmol, 1 eq) in THF at 0° C. was added 1 M n-BuLi in THF (5 mL, 5 mmol, 1.05 eq) and the reaction was stirred at 0° C. for 15 min. Morpholine (435 mg, 5 mmol, 1.05 eq) was added and the resulting mixture was stirred at RT for 16 h. LCMS showed indicated the reaction was complete. The reaction was quenched with water and extracted with DCM. The organic phase was concentrated under reduced pressure to afford a residue which was purified by flash chromatography to afford the title compound (232 mg, 20%).

Step 2: 2,5-dimethoxy-4-morpholinobenzaldehyde

To a solution of 4-(2,5-dimethoxyphenyl)morpholine (182 mg, 1 eq) in POCl3 (5 mL) was added DMF (0.5 mL). The resulting mixture was stirred at RT for 16 h. TLC indicated the reaction was complete. The reaction was quenched with water and extracted with DCM. The organic phase was concentrated under reduced pressure to afford a residue which was purified by flash chromatography to afford the title compound (92 mg, 45%).

Step 3: (E)-4-(2,5-dimethoxy-4-(2-nitrovinyl)phenyl)morpholine

To a solution of 2,5-dimethoxy-4-morpholinobenzaldehyde (92 mg, 0.36 mmol, 1 eq) in CH3NO2 (10 mL) was added NH4OAc (11 mg, 0.15 mmol, 0.4 eq) and the resulting mixture was stirred at 100° C. for 1 h. TLC indicated the reaction was complete. Water was added to quench the reaction. The yellow solid was filtered to afford the title compound (87 mg, 82%).

Step 4: 2-(2,5-dimethoxy-4-morpholinophenyl)ethan-1-amine

To a solution of (E)-4-(2,5-dimethoxy-4-(2-nitrovinyl)phenyl)morpholine (87 mg, 0.27 mmol, 1 eq) in THF (5 mL) was added LAH (38 mg, 1 mmol, 4 eq). Then the resulting mixture was stirred at RT for 2 h. TLC indicated the reaction was complete. Water and NaOH were added to quench the reaction. The resulting mixture was filtered and washed with EA. The organic phase was concentrated under reduced pressure to afford a residue which was purified by flash chromatography to afford the title compound (25 mg, 30%).

Step 5: N-(3-chloro-5-methylbenzyl)-2-(2,5-dimethoxy-4-morpholinophenyl)ethan-1-amine hydrochloride To a solution of 3-chloro-5-methylbenzaldehyde (14 mg, 0.094 mmol, 1 eq) in DCM (2 mL) was added 2-(2,5-dimethoxy-4-morpholinophenyl)ethan-1-amine (25 mg, 0.094 mmol, 1 eq), and NaBH(OAc)$_3$ (59 mg, 0.282 mmol, 3 eq) at RT. The resulting mixture was stirred at room temperature overnight. The reaction was quenched with aqueous NaHCO$_3$ solution and extracted with EA (50 mL×3). The organic layer was washed with brine, dried over Na$_2$SO$_4$, filtered and concentrated to give a crude product which was purified by silica gel column chromatography (DCM:MeOH=100/1) to afford a product which was treated with 4 M HCl in dioxane to obtain the title compound as a white solid (12 mg, 29%). LCMS: m/z 406.45[M+H]$^+$. $^1$H NMR (400 MHz, MeOD) δ 7.40 (s, 1H), 7.37 (s, 1H), 7.35 (s, 1H), 7.32 (s, 1H), 7.29 (s, 1H), 4.24 (s, 2H), 4.14 (t, J=4.7 Hz, 4H), 4.04 (s, 3H), 3.93 (s, 3H), 3.78 (s, 4H), 3.27 (dd, J=18.7, 10.0 Hz, 2H), 3.12 (dd, J=9.5, 6.2 Hz, 2H), 2.41 (s, 3H).

Example 53(a): (R)-2-((3-chloro-5-methylbenzyl)amino)-1-(2,5-dimethoxyphenyl)ethan-1-ol (2-32)

Example 53(b): (S)-2-((3-chloro-5-methylbenzyl)amino)-1-(2,5-dimethoxyphenyl)ethan-1-ol (2-33)

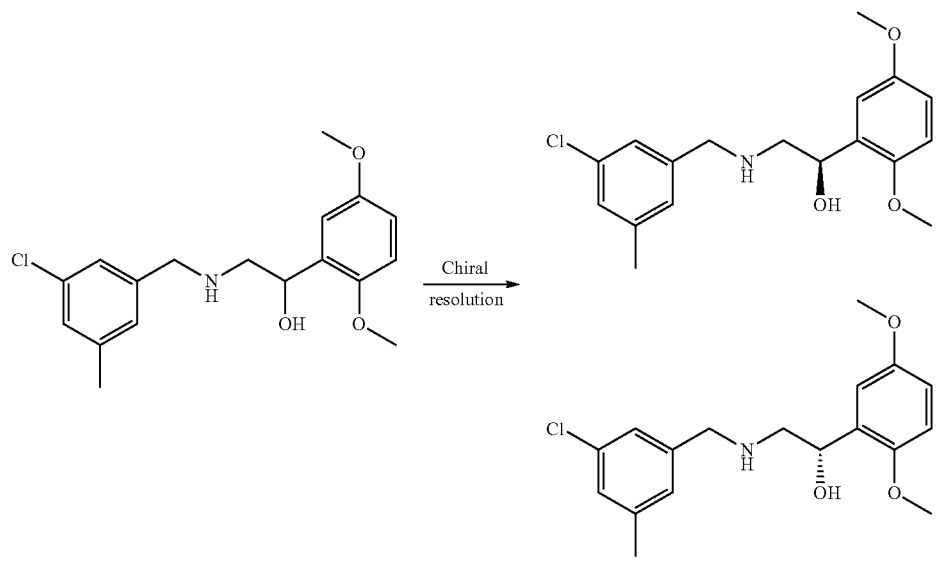 [SMILES: COc1ccc(OC)c(C(O)CNCc2cc(C)cc(Cl)c2)c1 ; COc1ccc(OC)c([C@@H](O)CNCc2cc(C)cc(Cl)c2)c1 ; COc1ccc(OC)c([C@H](O)CNCc2cc(C)cc(Cl)c2)c1]

2-((3-chloro-5-methylbenzyl)amino)-1-(2,5-dimethoxyphenyl)ethan-1-ol, 2-30 (48 mg, 0.14 mmol) was purified by chiral chromatography to afford (R)-2-((3-chloro-5-methylbenzyl)-amino)-1-(2,5-dimethoxyphenyl)ethan-1-ol (18 mg) and (S)-2-((3-chloro-5-methylbenzyl)-amino)-1-(2,5-dimethoxyphenyl)ethan-1-ol (16 mg). $^1$H NMR (400 MHz, CDCl$_3$) δ 7.11 (s, 1H), 7.07-7.03 (m, 2H), 7.01 (s, 1H), 6.80-6.73 (m, 2H), 5.03 (dd, J=8.4, 3.4 Hz, 1H), 3.83-3.71 (m, 8H), 2.96 (dd, J=12.1, 3.5 Hz, 1H), 2.72 (dd, J=12.1, 8.5 Hz, 1H), 2.32 (s, 3H). NMRs are identical for both.

Example 54: (R)-(4-(2-((3-chloro-5-methylbenzyl)amino)ethyl)-2,5-dimethoxyphenyl)-(imino)(methyl)-16-sulfanone (2-34)

Example 55: (S)-(4-(2-((3-chloro-5-methylbenzyl)amino)ethyl)-2,5-dimethoxyphenyl)-(imino)(methyl)-16-sulfanone (2-35)

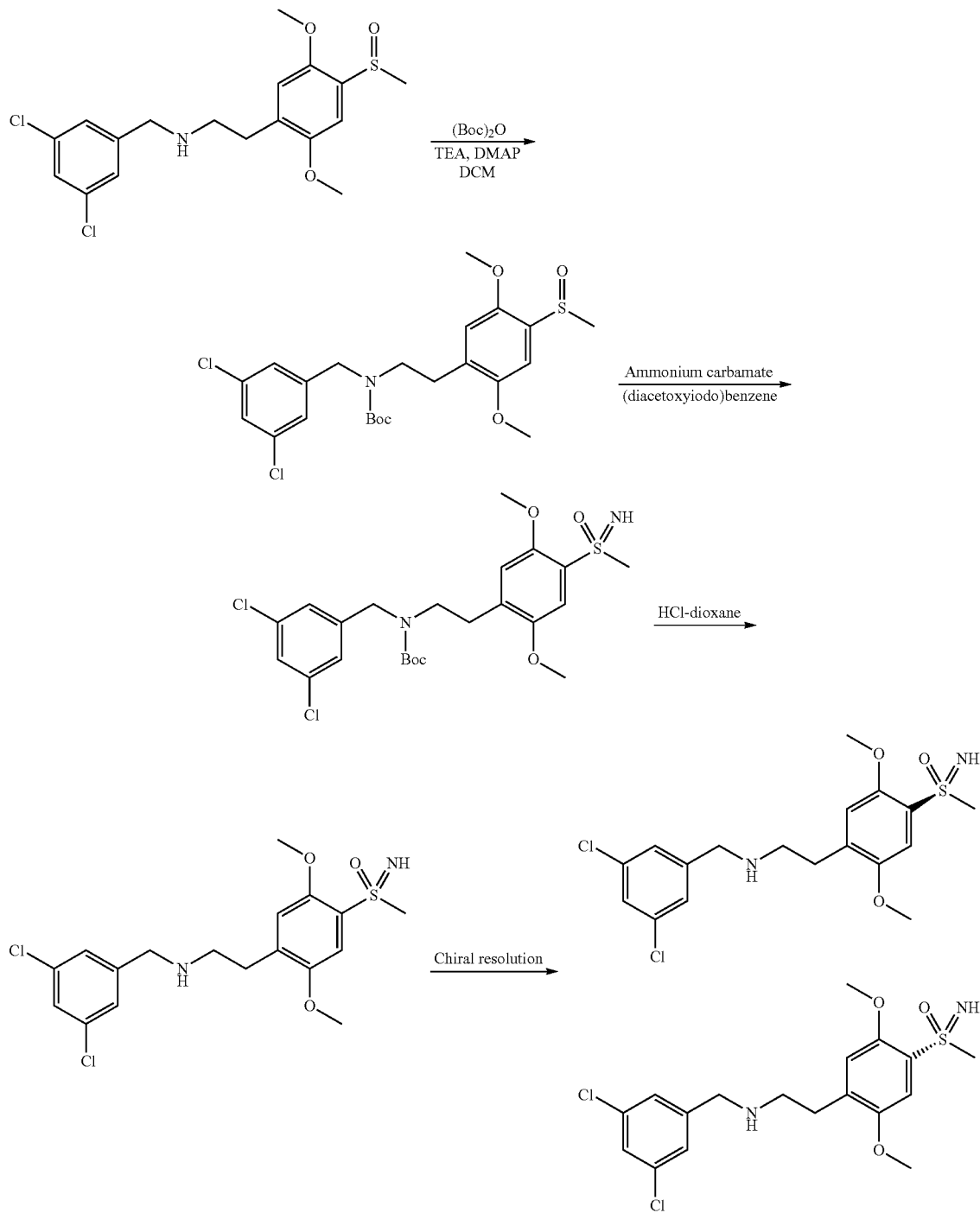

Step 1: tert-butyl(3-chloro-5-methylbenzyl)(2,5-dimethoxy-4-methylsulfinyl)phenethyl)-carbamate N-(3-chloro-5-methylbenzyl)-2-(2,5-dimethoxy-4-(methylsulfinyl)phenyl)ethan-1-amine (283 mg, 0.74 mmol, 1 eq) in DCM was added di-tert-butyl dicarbonate (324 mg, 1.48 mmol, 2 eq), TEA (224 mg, 2.22 mmol, 3 eq) and DMAP (9 mg, 0.074 mmol, 0.1 eq). The resulting mixture was stirred at RT for 16 h. LCMS indicated reaction was complete. The reaction was quenched by water, extracted by DCM. The combined organic phase was concentrated under reduced pressure to afford the title compound (330 mg, 92%).

Step 2: tert-butyl(3-chloro-5-methylbenzyl)(2,5-dimethoxy-4-(S-methylsulfonimidoyl)-phenethyl)carbamate tert-butyl(3-chloro-5-methylbenzyl)(2,5-dimethoxy-4-(methylsulfinyl)phenethyl)carbamate (180 mg, 0.37 mmol, 1 eq) in MeOH (5 mL) was added ammonium carbamate (58 mg, 0.74 mmol, 2 eq) and (diacetoxyiodo)benzene (238 mg, 0.74 mmol, 2 eq). The resulting mixture was stirred at RT for 16 h. LCMS indicated the reaction was complete. The reaction was quenched water and extracted by DCM. The organic phase was concentrated under reduced pressure to afford the crude product which was purified by flash chromatography to afford the title compound (100 mg, 52%).

Step 3: (4-(2-((3-chloro-5-methylbenzyl)amino)ethyl)-2,5-dimethoxyphenyl)(imino)-(methyl)-16-sulfanone hydrochloride tert-butyl(3-chloro-5-methylbenzyl)(2,5-dimethoxy-4-(S-methylsulfonimidoyl)phenethyl)-carbamate (100 mg, 0.20 mmol, 1 eq) in DCM (10 mL) was added 4 M HCl in dioxane (5 mL). The resulting mixture was stirred at RT for 16 h. LCMS indicated the reaction was complete. The reaction was concentrated, washed with petroleum ether (10 mL) and filtered to afford the title compound as the HCl salt (96 mg, 90%). LCMS: m/z 398.15[M+H]$^+$. $^1$H NMR (400 MHz, CDCl3) δ 7.46 (s, 1H), 7.09 (s, 1H), 7.05 (s, 1H), 6.98 (s, 1H), 6.89 (s, 1H), 3.94 (s, 3H), 3.83 (s, 3H), 3.76 (s, 2H), 3.28 (s, 3H), 2.87 (s, 4H), 2.31 (s, 3H).

Step 4: (R)-(4-(2-((3-chloro-5-methylbenzyl)amino)ethyl)-2,5-dimethoxyphenyl)(imino)(methyl)-16-sulfanone (2-34)

(S)-(4-(2-((3-chloro-5-methylbenzyl)amino)ethyl)-2,5-dimethoxyphenyl)(imino)(methyl)-16-sulfanone (2-35)

(4-(2-((3-chloro-5-methylbenzyl)amino)ethyl)-2,5-dimethoxyphenyl)(imino)(methyl)-16-sulfanone hydrochloride (60 mg, 0.14 mmol) was purified by chiral chromatography to afford (R)-(4-(2-((3-chloro-5-methylbenzyl)amino)ethyl)-2,5-dimethoxyphenyl)(imino)(methyl)-16-sulfanone (18 mg) and (S)-(4-(2-((3-chloro-5-methylbenzyl)amino)ethyl)-2,5-dimethoxyphenyl)(imino)(methyl)-16-sulfanone (16 mg). LCMS: m/z 398.15[M+H]$^+$. $^1$H NMR (400 MHz, CDCl$_3$) δ 7.46 (s, 1H), 7.09 (s, 1H), 7.05 (s, 1H), 6.98 (s, 1H), 6.89 (s, 1H), 3.93 (s, 3H), 3.83 (s, 3H), 3.75 (s, 2H), 3.28 (s, 3H), 2.87 (s, 4H), 2.31 (s, 3H). Spectra were identical for both enantiomers.

Example 56: 3-(((2,5-dimethoxyphenethyl)amino)methyl)-5-methylbenzonitrile (2-36)

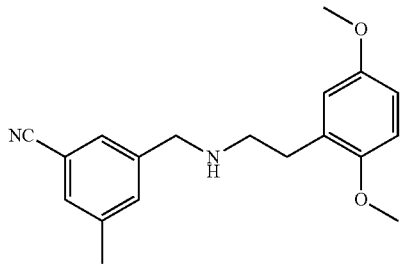 [SMILES: COc1ccc(OC)c(CCNCc2cc(C)cc(C#N)c2)c1]

The same procedure as for the preparation of 2-2 was applied to afford a product which was treated with 4 M HCl in dioxane to provide the title compound as a white solid. (47 mg, 20%). LCMS: m/z 311.50[M+H]$^+$. $^1$H NMR (400 MHz, DMSO) δ 9.37 (s, 2H), 7.85 (s, 1H), 7.74 (s, 1H), 7.72 (s, 1H), 6.93 (d, J=8.8 Hz, 1H), 6.81 (dt, J=7.0, 3.0 Hz, 2H), 4.19 (t, J=5.5 Hz, 2H), 3.74 (s, 3H), 3.70 (s, 3H), 3.07 (d, J=5.2 Hz, 2H), 2.99-2.85 (m, 2H), 2.38 (s, 3H).

Example 57: 3-chloro-5-(((2,5-dimethoxyphenethyl)amino)methyl)benzonitrile hydrochloride (2-37)

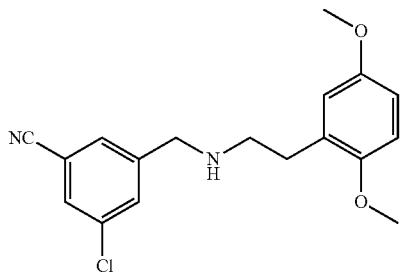 [SMILES: COc1ccc(OC)c(CCNCc2cc(Cl)cc(C#N)c2)c1]

The same procedure as for the preparation of 2-2 was applied to afford the crude product as an oil which was treated with 4 M HCl in dioxane to provide the title compound as a white solid (100 mg, 45%). LCMS: m/z 332.15 [M+H]$^+$. $^1$H NMR (400 MHz, MeOD) δ 7.97-7.95 (m, 1H), 7.91 (t, J=1.5 Hz, 1H), 7.85 (s, 1H), 6.95 (d, J=8.5 Hz, 1H), 6.88-6.82 (m, 2H), 4.32 (s, 2H), 3.83 (s, 3H), 3.77 (s, 3H), 3.29 (dd, J=8.9, 6.7 Hz, 2H), 3.06-2.99 (m, 2H).

Example 58: Methyl 3-chloro-5-(((2,5-dimethoxyphenethyl)amino)methyl)benzoate hydrochloride (2-38)

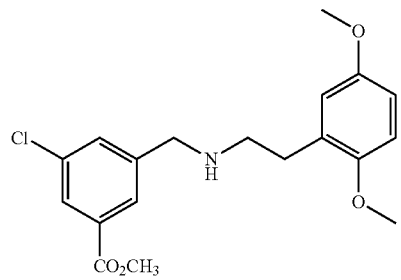 [SMILES: COC(=O)c1cc(Cl)cc(CNCCc2cc(OC)ccc2OC)c1]

The same procedure as for the preparation of 2-2 was applied to afford the crude product as an oil which was treated with 4 M HCl in dioxane to provide the title compound as a white solid (120 mg, 54%). LCMS: m/z 365.15 [M+H]+. 1H NMR (400 MHz, MeOD) δ 8.12 (s, 1H), 8.09 (t, J=1.6 Hz, 1H), 7.82 (t, J=1.7 Hz, 1H), 6.94 (d, J=8.6 Hz, 1H), 6.88-6.82 (m, 2H), 4.31 (s, 2H), 3.97 (s, 3H), 3.82 (s, 3H), 3.77 (s, 3H), 3.28 (dd, J=8.8, 6.7 Hz, 2H), 3.07-2.99 (m, 2H).

Example 59: 3-chloro-5-(((2,5-dimethoxyphenethyl)amino)methyl)benzoic acid hydrochloride (2-39)

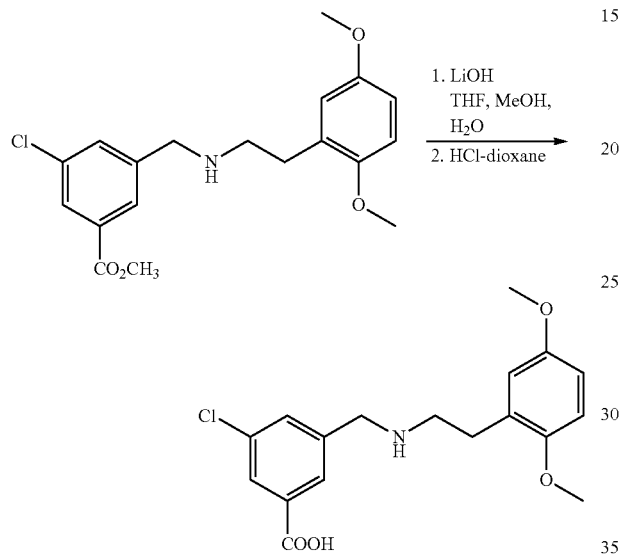

A solution of methyl 3-chloro-5-(((2,5-dimethoxyphenethyl)amino)methyl)benzoate (100 mg, 0.27 mmol, 1 eq), lithium hydroxide (32 mg, 1.35 mmol, 5 eq) in THF/MeOH/water (1:1, 4 mL) was stirred at RT for 16 h. TLC indicated the reaction was complete. The reaction mixture was washed by NaHCO3 (aq.) and extracted with DCM. The organic phase was collected and concentrated under reduced pressure. The resulting residue was purified by flash chromatography (eluting with DCM/MeOH=10/1) to afford the crude product as oil which was treated with 4 M HCl in dioxane to obtain the title compound as a white solid (45 mg, 47%). LCMS: m/z 350.45 [M+H]+. 1H NMR (400 MHz, CDCl3) δ 9.63 (s, 2H), 8.25 (s, 1H), 8.09 (s, 1H), 7.46 (s, 1H), 6.64 (d, J=2.8 Hz, 1H), 6.61 (d, J=8.9 Hz, 1H), 6.56 (dd, J=8.9, 2.8 Hz, 1H), 4.19 (s, 2H), 3.61 (s, 3H), 3.60 (s, 3H), 3.19 (t, J=6.4 Hz, 2H), 2.98 (t, J=6.8 Hz, 2H).

Example 60: N-(3-chloro-5-methylbenzyl)-1-(4-iodo-2,5-dimethoxyphenyl)propan-2-amine (2-40)

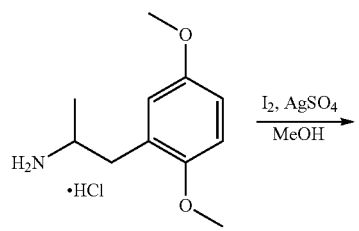

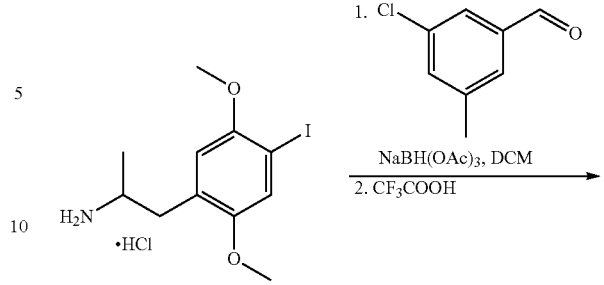

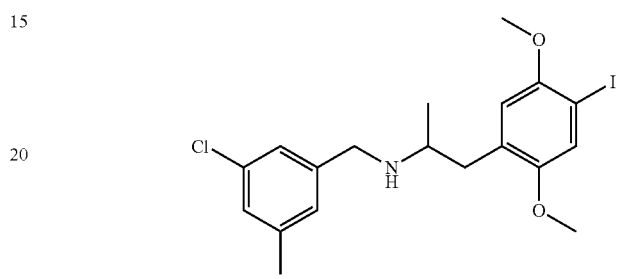

Step 1: 1-(4-iodo-2,5-dimethoxyphenyl)propan-2-amine

A solution of 1-(2,5-dimethoxyphenyl)propan-2-amine hydrochloride, from the preparation of 2-27 (190 mg, 0.82 mmol, 1 eq), silver sulfate (586 mg, 1.89 mmol, 2.3 eq) and iodine (483 mg, 1.89 mmol, 2.3 eq) in MeOH (10 mL) was stirred at RT for 16 h. The reaction was washed by NaHCO3 (aq.) and extracted with DCM. The organic phase was concentrated under reduced pressure to afford a residue which was purified by flash chromatography (DCM/MeOH=10/1) to afford the title compound (50 mg, 19%). LCMS: (ES+): m/z 322.15 [M+H]+. 1H NMR (400 MHz, MeOD) δ 7.38 (s, 1H), 6.84 (s, 1H), 3.84 (s, 3H), 3.83 (s, 3H), 3.56 (dd, J=13.4, 6.7 Hz, 1H), 2.93 (dd, J=13.5, 6.8 Hz, 1H), 2.85 (dd, J=13.5, 7.0 Hz, 1H), 1.28 (d, J=6.6 Hz, 3H).

Step 2: N-(3-chloro-5-methylbenzyl)-1-(4-iodo-2,5-dimethoxyphenyl)propan-2-amine A solution of 1-(4-iodo-2,5-dimethoxyphenyl)propan-2-amine (50 mg, 0.16 mmol, 1 eq) and 3-chloro-5-methylbenzaldehyde (24 mg, 0.16 mmol, 1 eq) in DCM (5 mL) was stirred at rt for 1 h followed by the addition of NaBH(OAc)3 (120 mg, 0.64 mmol, 3 eq). The resulting mixture was stirred at RT for 16 h. The reaction was washed with NaHCO3 (aq.) and extracted by DCM. The organic phase was concentrated under reduced pressure to afford a residue which was purified by flash chromatography (DCM/MeOH=10/1) to afford the product which was purified by preparative HPLC to afford the title compound as a TFA salt (50 mg, 54% yield). LCMS: (ES+): m/z 460.25 [M+H]+. 1H NMR (400 MHz, MeOD) δ 7.38 (s, 1H), 7.35 (s, 2H), 7.24 (s, 1H), 6.84 (s, 1H), 4.33-4.20 (m, 2H), 3.84 (s, 3H), 3.81 (s, 3H), 3.61 (dq, J=13.2, 6.7 Hz, 1H), 3.22 (dd, J=13.1, 4.9 Hz, 1H), 2.80 (dd, J=13.2, 9.1 Hz, 1H), 2.41 (s, 3H), 1.31 (d, J=6.6 Hz, 3H).

Example 61: (R)-1-(2,5-dimethoxyphenyl)-2-((3-fluoro-5-methylbenzyl)amino)ethan-1-ol hydrochloride (2-41)

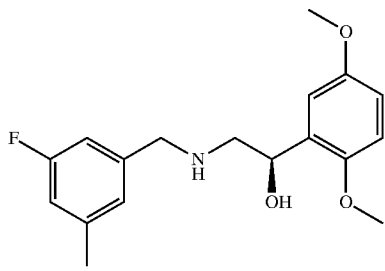 [SMILES: COc1ccc(OC)c([C@@H](O)CNCc2cc(C)cc(F)c2)c1]

Example 62: (S)-1-(2,5-dimethoxyphenyl)-2-((3-fluoro-5-methylbenzyl)amino)ethan-1-ol hydrochloride (2-42)

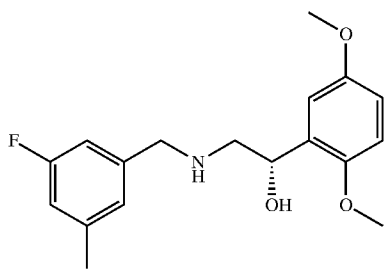 [SMILES: COc1ccc(OC)c([C@H](O)CNCc2cc(C)cc(F)c2)c1]

The same procedure as for the preparation of 2-2 was applied to afford a racemic mixture that was resolved by chiral chromatography to give 2-41 and 2-42. LCMS: m/z 320.45 [M+H]$^+$. $^1$H NMR (400 MHz, CDCl$_3$) δ 7.05 (d, J=2.4 Hz, 1H), 6.91 (s, 1H), 6.85 (d, J=9.2 Hz, 1H), 6.77 (m, 3H), 5.04 (dd, J=8.5, 3.4 Hz, 1H), 3.87-3.71 (m, 8H), 2.97 (dd, J=12.1, 3.4 Hz, 1H), 2.73 (dd, J=12.1, 8.6 Hz, 1H), 2.33 (s, 3H).

Example 63: GPCR Arrestin Assay: Arrestin Pathway (Performed by DiscoverX Eurofins)

The PathHunter® β-Arrestin assay monitors the activation of a GPCR in a homogenous, non-imaging assay format using a technology developed by DiscoverX called Enzyme Fragment Complementation (EFC) with β-galactosidase (β-Gal) as the functional reporter. The enzyme is split into two inactive complementary portions (EA for Enzyme Acceptor and PK for ProLink) expressed as fusion proteins in the cell. EA is fused to β-Arrestin and PK is fused to the GPCR of interest. When the GPCR is activated and β-Arrestin is recruited to the receptor, ED and EA complementation occurs, restoring j-Gal activity which is measured using chemiluminescent PathHunter® Detection Reagents.

PathHunter cell lines (DiscoveRx Eurofins) were expanded from freezer stocks according to standard procedures. Cells were seeded in a total volume of 20 µL into white walled, 384-well microplates and incubated at 37° C. for the appropriate time prior to testing. For agonist determination, cells were incubated with sample to induce response. Intermediate dilution of sample stocks was performed to generate 5× sample in assay buffer. 5 µL of 5× sample was added to cells and incubated at 37° C. or room temperature for 90 to 180 minutes. Vehicle concentration was 1%. b-Arrestin assay signal was generated through a single addition of 12.5 or 15 µL (50% v/v) of PathHunter Detection reagent cocktail, followed by a one hour incubation at room temperature. Microplates were read following signal generation with a PerkinElmer Envision™ instrument for chemiluminescent signal detection. Compound activity was analyzed using CBIS data analysis suite (ChemInnovation, CA). For agonist mode assays, percentage activity was calculated using the following formula:

% Activity =

100% × (mean $RFU$ of test sample-mean $RLU$ of vehicle control)/

(mean MAX control ligand-mean $RLU$ of vehicle control).

In these studies, the MAX control ligand response was generated using 10 µM serotonin.

Calcium Mobilization Assay Method (Performed by DiscoveRx Eurofins)

The Calcium No-Wash$^{PLUS}$ assay monitors the activation of a GPCR via Gq secondary messenger signaling in a live cell, non-imaging assay format. Calcium mobilization in PathHunter® cell lines or other cell lines stably expressing Gq-coupled GPCRs is monitored using a calcium-sensitive dye that is loaded into cells. GPCR activation by a compound results in the release of calcium from intracellular stores and an increase in dye fluorescence that is measured in real-time.

Cell lines expressing the GPCR of interest were expanded from freezer stocks according to standard procedures. Cells were seeded in a total volume of 20 µL into black-walled, clear-bottom, Poly-D-lysine coated 384-well microplates and incubated at 37° C. for the appropriate time prior to testing. Assays were performed in 1× Dye Loading Buffer consisting of 1× Dye, 1× Additive A and 2.5 mM Probenecid in HBSS/20 mM Hepes. Probenicid was prepared fresh. Cells were loaded with dye prior to testing. Media was aspirated from cells and replaced with 20 µL Dye Loading Buffer. Cells were incubated for 30-60 minutes at 37° C. For agonist determination, cells were incubated with sample to induce response. After dye loading, cells were removed from the incubator and 10 µL HBSS/20 mM Hepes was added. 3× vehicle was included in the buffer when performing agonist dose curves to define the EC80 for subsequent antagonist assays. Cells were incubated for 30 minutes at room temperature in the dark to equilibrate plate temperature. Intermediate dilution of sample stocks was performed to generate 4× sample in assay buffer. Compound agonist activity was measured on a FLIPR Tetra (MDS). Calcium mobilization was monitored for 2 minutes and 10 µL 4× sample in HBSS/20 mM Hepes was added to the cells 5 seconds into the assay. Compound activity data was analyzed using CBIS data analysis suite (ChemInnovation, CA). For agonist mode assays, percentage activity is calculated using the following formula:

$$\% \text{ Activity} =$$
$$100\% \times (\text{mean } RFU \text{ of test sample} - \text{mean } RFU \text{ of vehicle control}) /$$
$$(\text{mean MAX } RFU \text{ control ligand} - \text{mean } RFU \text{ of vehicle control}).$$

In these studies, the MAX RFU was generated by using 0.1 µM serotonin for the calcium mobilization assay.

Biological Experiments

Compounds 1-1·HCl, 1-2 and 2-1 were assessed for biological activity across a panel of 5-HT receptors including 5-HT2A, 5-HT2B, 5-HT2C and 5-HT1A. Biased signaling was assessed by monitoring both intracellular Gq-mediated calcium release, as well as beta-arrestin activation and recruitment to the GPCR. The results are shown in Table 3 below.

TABLE 3

EC50 values (in micromolar) measured for Compounds 1-1·HCl, 1-2 and 2-1 across a panel of 5-HT receptors.

| 5-HT Receptor Assessed | $EC_{50}$ (µM) Values Measured with Compound 1-1·HCl | $EC_{50}$ (µM) Values Measured with Compound 1-2 | $EC_{50}$ (µM) Values Measured with Compound 2-1 |
|---|---|---|---|
| 5-HT1A (Gq signaling) | 17.15 | 2.432 | 24.75 |
| 5-HT2A (Gq signaling) | 0.134 | 0.066 | 0.010 |
| 5-HT2B (Gq signaling) | 23.15 | 37.09 | 44.06 |
| 5-HT2C (Gq signaling) | 10.02 | 1.294 | 0.091 |
| 5-HT2A (β-arrestin signaling) | 0.172 | 0.105 | 0.023 |

The Compounds displayed greater potency on the 5-HT2A receptor compared to the other 5-HT receptors studied. The 5-HT2A activity is shown in Tables 4-5. Interestingly, all compounds displayed selectivity for 5-HT2A demonstrating as much as ~560-fold selectivity for 5-HT2A compared to 5-HT2B. Such selectivity is surprising and unexpected given the structural similarity between the 5-HT2A and 5-HT2B receptors. Moreover, this selectivity will allow greater safety advantages over other non-selective psychedelics by potentially decreasing the risk of cardiac valvulopathy typically associated with prolonged 5-HT2B activation and repeat-dosing. Among the other receptors, Compound 1-2 showed approximately 7- and 10-fold greater potency for 5-HT1A and 5-HT2C than compound 1-1·HCl. All compounds also were potent activators of beta-arrestin recruitment at 5-HT2A at slightly lower potencies than Gq-mediated signaling suggesting a slight Gq signaling bias. Compound 2-1 was found to be the most potent of all compounds studied at 5-HT2A and 5-HT2C and displayed the greatest selectivity for 5-HT2A over 5-HT2B at ~4400-fold. As with the other compounds, no appreciable activity was observed at 5-HT2B at concentrations less than 10 uM.

The $EC_{50}$ profiles of the compounds demonstrated that all were agonists of 5-HT2A mediated signaling. However, while Compounds 1-1·HCl and 1-2 displayed full-agonism, Compound 2-1 was observed to be a partial-agonist (FIG. 1). Both compounds 1-1·HCl and 1-2 demonstrated maximum effect levels of ~100% compared to the maximum serotonin responses for Gq signaling, while the maximum effect level for Compound 2-1 was ~86%. Similar to the potency findings of biased signaling above, all compounds showed less than 100% maximal response for beta-arrestin suggesting a slight bias for Gq-mediated signaling of the 5-HT2A receptor.

TABLE 4

5HT2A Activity for Compounds 1-1 to Compounds 1-21

| No. | Structure | 5HT2A ACTIVITY (% Max Activation @ 0.3 uM) |
|---|---|---|
| 1-1 | 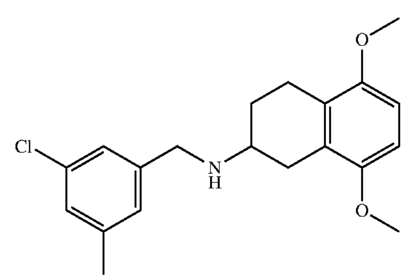 [SMILES: COc1ccc(OC)c2c1CCC(NCc1cc(C)cc(Cl)c1)C2] | 67 |
| 1-2 | 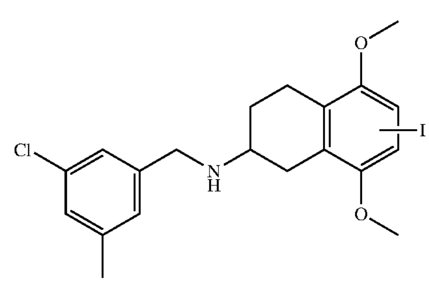 | 79 |

TABLE 4-continued
5HT2A Activity for Compounds 1-1 to Compounds 1-21
| No. | Structure | 5HT2A ACTIVITY (% Max Activation @ 0.3 uM) |
|---|---|---|
| 1-2A | 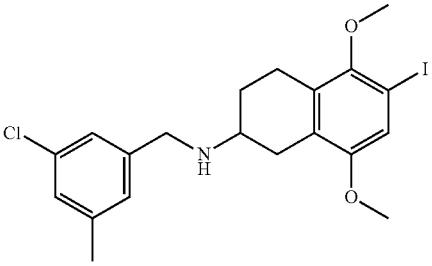 [SMILES: COc1cc(I)c(OC)c2c1CC(NCc1cc(C)cc(Cl)c1)CC2] | 73 |
| 1-2B | 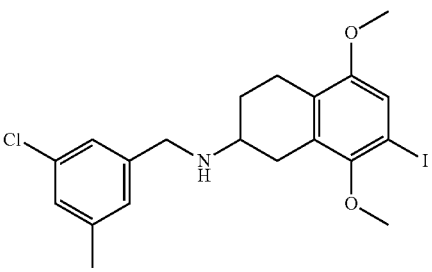 [SMILES: COc1cc(I)c(OC)c2c1CCC(NCc1cc(C)cc(Cl)c1)C2] | NA |
| 1-3 | 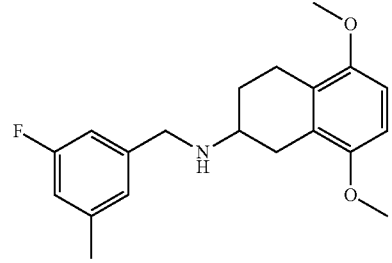 | 76 |
| 1-4 | 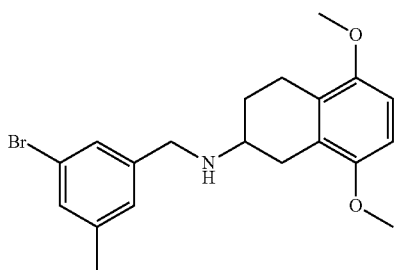 [SMILES: COc1ccc(OC)c2c1CCC(NCc1cc(C)cc(Br)c1)C2] | 42 |
| 1-5 | 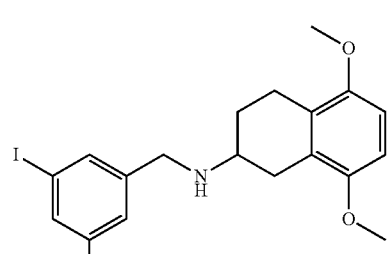 | 12 |

TABLE 4-continued
5HT2A Activity for Compounds 1-1 to Compounds 1-21
| No. | Structure | 5HT2A ACTIVITY (% Max Activation @ 0.3 uM) |
|---|---|---|
| 1-6 | 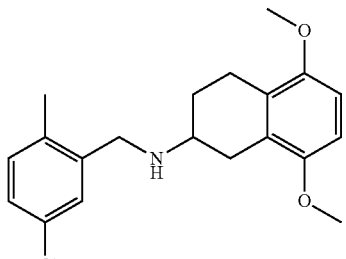 | NA |
| 1-7 | 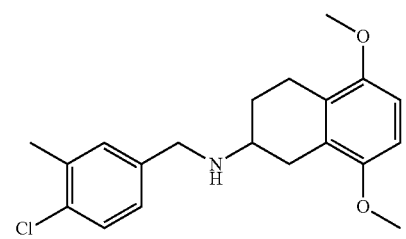 | NA |
| 1-8 | 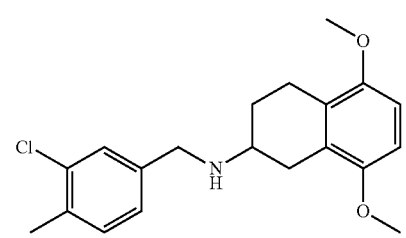 | NA |
| 1-9 | 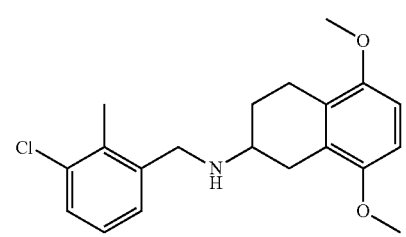 [SMILES: COc1ccc(OC)c2c1CCC(NCc1cccc(Cl)c1C)C2] | 7 |
| 1-10 | 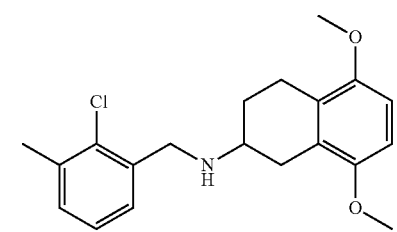 | 2 |
| 1-11 | 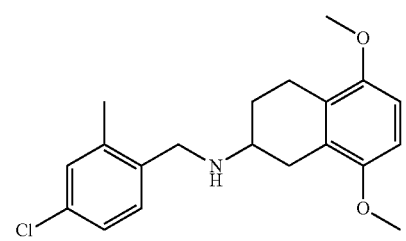 [SMILES: COc1ccc(OC)c2c1CCC(NCc1ccc(Cl)cc1C)C2] | 1 |

TABLE 4-continued
5HT2A Activity for Compounds 1-1 to Compounds 1-21
| No. | Structure | 5HT2A ACTIVITY (% Max Activation @ 0.3 uM) |
|---|---|---|
| 1-12 | 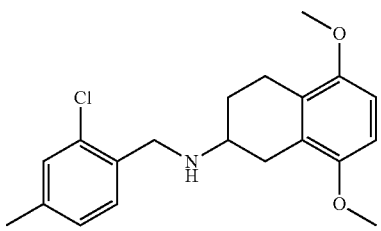 [SMILES: COc1ccc(OC)c2c1CCC(NCc1ccc(C)cc1Cl)C2] | 4 |
| 1-13 | 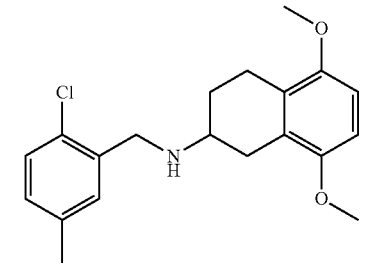 [SMILES: COc1ccc(OC)c2c1CCC(NCc1cc(C)ccc1Cl)C2] | 15 |
| 1-14 | 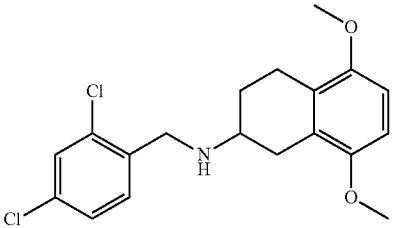 [SMILES: COc1ccc(OC)c2c1CCC(NCc1ccc(Cl)cc1Cl)C2] | NA |
| 1-15 | 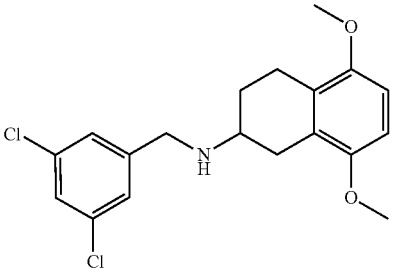 [SMILES: COc1ccc(OC)c2c1CCC(NCc1cc(Cl)cc(Cl)c1)C2] | 11 |
| 1-16 | 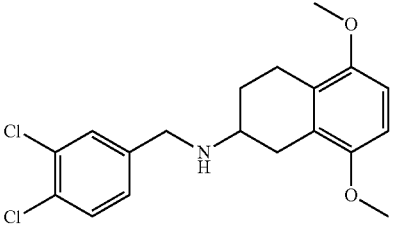 | NA |
| 1-17 | 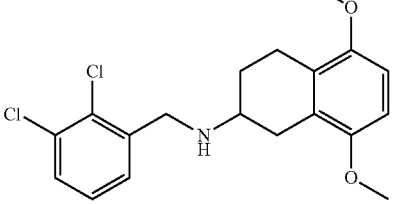 | 1 |

TABLE 4-continued

5HT2A Activity for Compounds 1-1 to Compounds 1-21

| No. | Structure | 5HT2A ACTIVITY (% Max Activation @ 0.3 uM) |
|---|---|---|
| 1-18 | 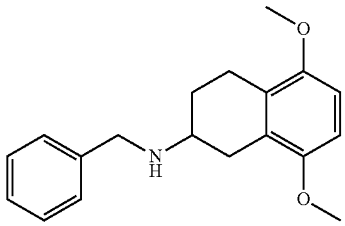 [SMILES: COc1ccc(OC)c2c1CCC(NCc1ccccc1)C2] | 6 |
| 1-19 | 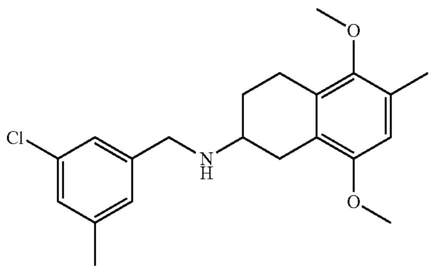 [SMILES: COc1cc(C)c(OC)c2c1CC(NCc1cc(C)cc(Cl)c1)CC2] | 73 |
| 1-20 | 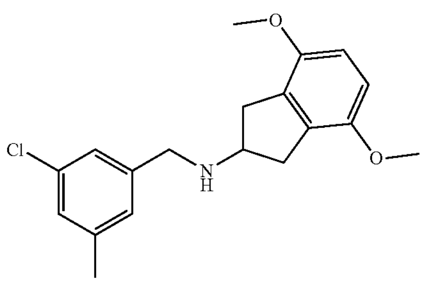 [SMILES: COc1ccc(OC)c2c1CC(NCc1cc(C)cc(Cl)c1)C2] | 59 |
| 1-21 | 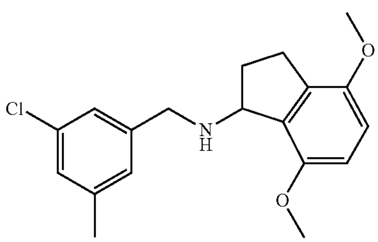 [SMILES: COc1ccc(OC)c2c1CCC2NCc1cc(C)cc(Cl)c1] | 9 |

TABLE 5

5HT2A Activity for Compounds 2-1 to Compounds 2-42

| No. | Structure | 5HT2A ACTIVITY (% Max Activation @ 0.3 uM) |
|---|---|---|
| 2-1 | 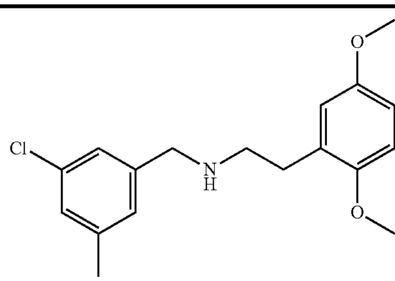 | 98 |

TABLE 5-continued
5HT2A Activity for Compounds 2-1 to Compounds 2-42
| No. | Structure | 5HT2A ACTIVITY (% Max Activation @ 0.3 uM) |
|---|---|---|
| 2-2 | 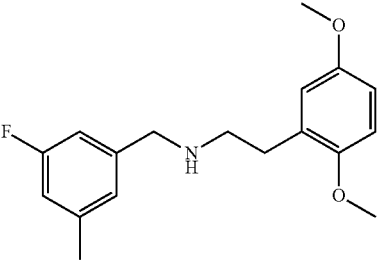 | 76 |
| 2-3 | 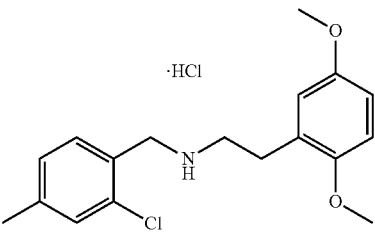 | 8 |
| 2-4 | 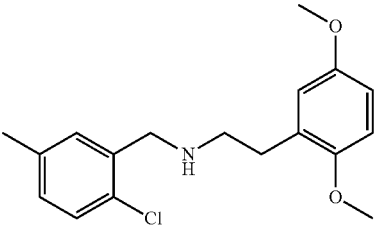 | 67 |
| 2-5 | 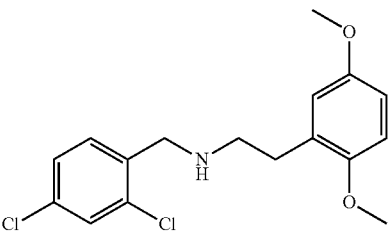 [SMILES: COc1ccc(OC)c(CCNCc2ccc(Cl)cc2Cl)c1] | NA |
| 2-6 | 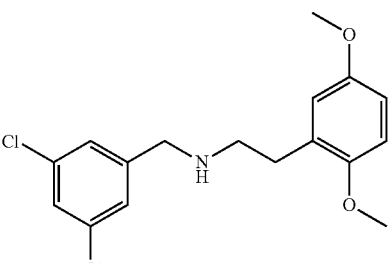 | 68 |

TABLE 5-continued

5HT2A Activity for Compounds 2-1 to Compounds 2-42

| No. | Structure | 5HT2A ACTIVITY (% Max Activation @ 0.3 uM) |
|---|---|---|
| 2-7 | 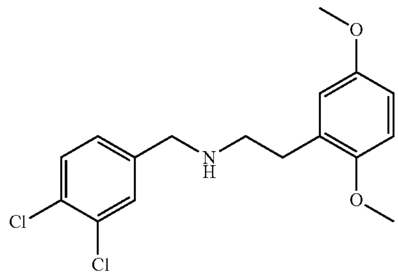 [SMILES: COc1ccc(OC)c(CCNCc2ccc(Cl)c(Cl)c2)c1] | NA |
| 2-8 | 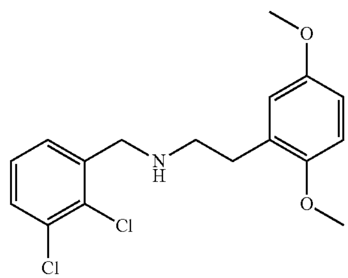 [SMILES: COc1ccc(OC)c(CCNCc2cccc(Cl)c2Cl)c1] | 33 |
| 2-9 | 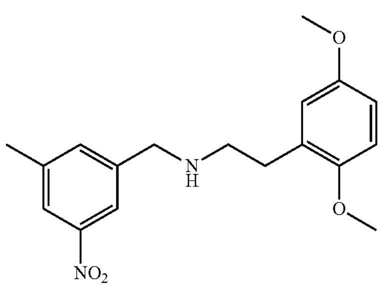 | 5 |
| 2-10 | 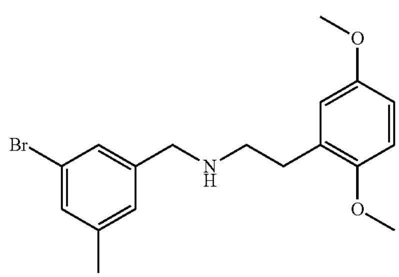 [SMILES: COc1ccc(OC)c(CCNCc2cc(C)cc(Br)c2)c1] | 79 |
| 2-11 | 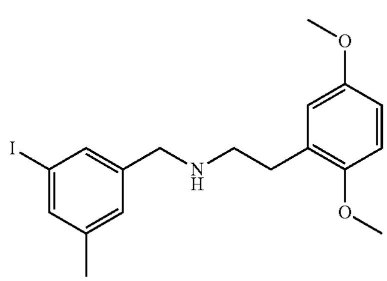 [SMILES: COc1ccc(OC)c(CCNCc2cc(C)cc(I)c2)c1] | 76 |

TABLE 5-continued
5HT2A Activity for Compounds 2-1 to Compounds 2-42
| No. | Structure | 5HT2A ACTIVITY (% Max Activation @ 0.3 uM) |
|---|---|---|
| 2-12 | 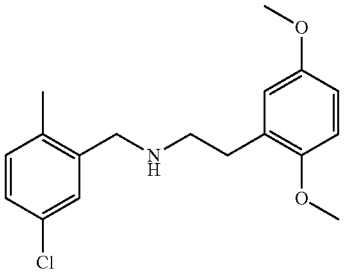 [SMILES: COc1ccc(OC)c(CCNCc2cc(Cl)ccc2C)c1] | 41 |
| 2-13 | 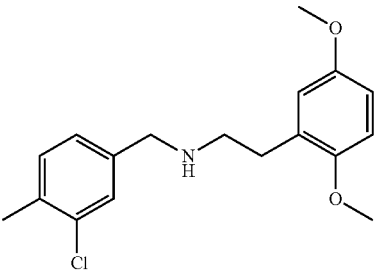 [SMILES: COc1ccc(OC)c(CCNCc2ccc(C)c(Cl)c2)c1] | NA |
| 2-14 | 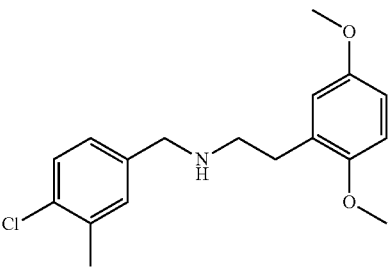 [SMILES: COc1ccc(OC)c(CCNCc2ccc(Cl)c(C)c2)c1] | 1 |
| 2-15 | 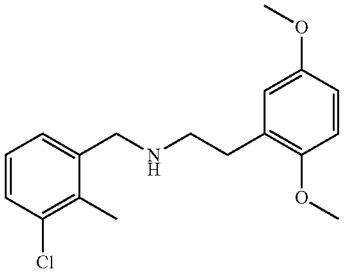 [SMILES: COc1ccc(OC)c(CCNCc2cccc(Cl)c2C)c1] | 20 |
| 2-16 | 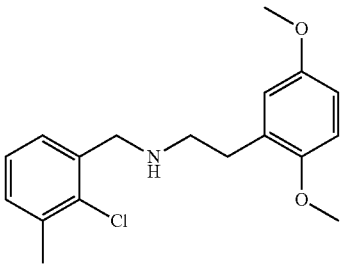 [SMILES: COc1ccc(OC)c(CCNCc2cccc(C)c2Cl)c1] | 64 |

TABLE 5-continued

5HT2A Activity for Compounds 2-1 to Compounds 2-42

| No. | Structure | 5HT2A ACTIVITY (% Max Activation @ 0.3 uM) |
|---|---|---|
| 2-17 | 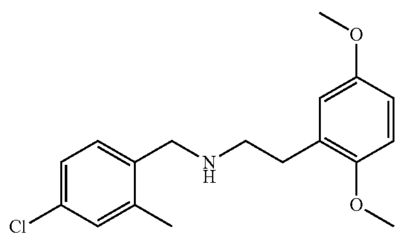 [SMILES: COc1ccc(OC)c(CCNCc2ccc(Cl)cc2C)c1] | NA |
| 2-18 | 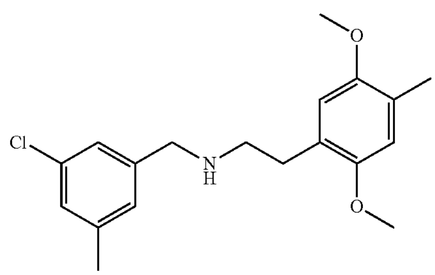 [SMILES: COc1cc(CCNCc2cc(C)cc(Cl)c2)c(OC)cc1C] | 94 |
| 2-19 | 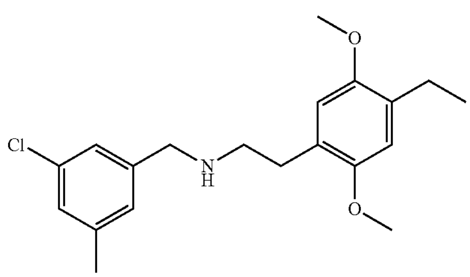 [SMILES: CCc1cc(OC)c(CCNCc2cc(C)cc(Cl)c2)cc1OC] | 84 |
| 2-20 | 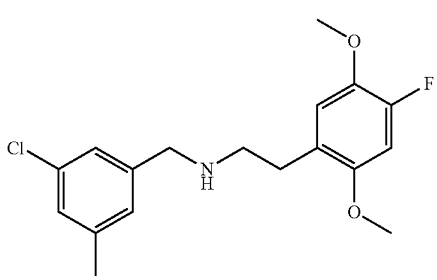 [SMILES: COc1cc(CCNCc2cc(C)cc(Cl)c2)c(OC)cc1F] | 89 |
| 2-21 | 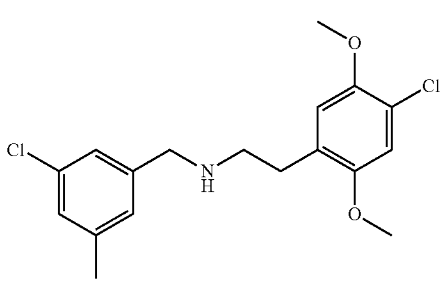 [SMILES: COc1cc(CCNCc2cc(C)cc(Cl)c2)c(OC)cc1Cl] | 92 |

TABLE 5-continued

5HT2A Activity for Compounds 2-1 to Compounds 2-42

| No. | Structure | 5HT2A ACTIVITY (% Max Activation @ 0.3 uM) |
|---|---|---|
| 2-22 | 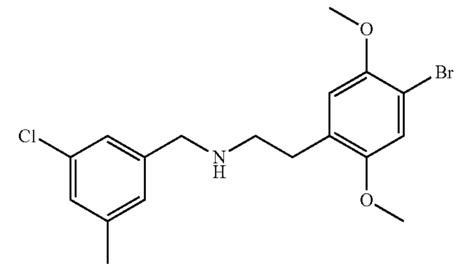 [SMILES: COc1cc(CCNCc2cc(C)cc(Cl)c2)c(OC)cc1Br] | 85 |
| 2-23 | 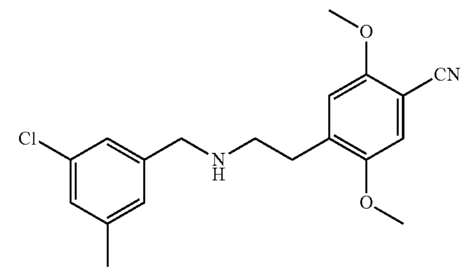 [SMILES: COc1cc(CCNCc2cc(C)cc(Cl)c2)c(OC)cc1C#N] | 96 |
| 2-24 | 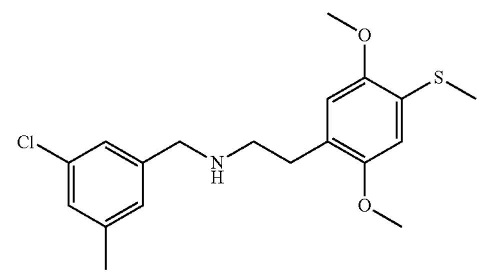 | 91 |
| 2-25 | 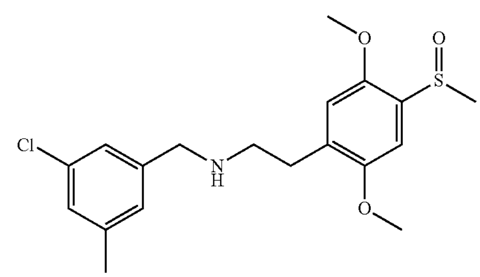 [SMILES: COc1cc(S(C)=O)c(OC)cc1CCNCc1cc(C)cc(Cl)c1] | 95 |
| 2-26 | 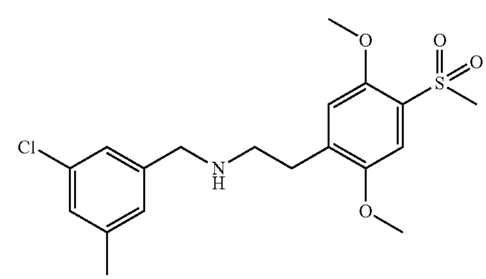 [SMILES: COc1cc(S(C)(=O)=O)c(OC)cc1CCNCc1cc(C)cc(Cl)c1] | 95 |

TABLE 5-continued
5HT2A Activity for Compounds 2-1 to Compounds 2-42
| No. | Structure | 5HT2A ACTIVITY (% Max Activation @ 0.3 uM) |
|---|---|---|
| 2-27 | 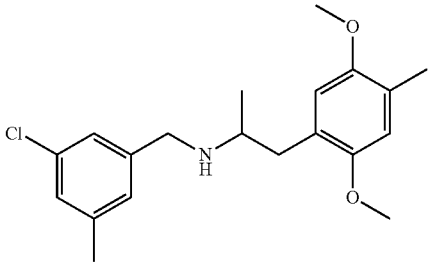 [SMILES: COc1cc(CC(C)NCc2cc(C)cc(Cl)c2)c(OC)cc1C] | 84 |
| 2-28 | 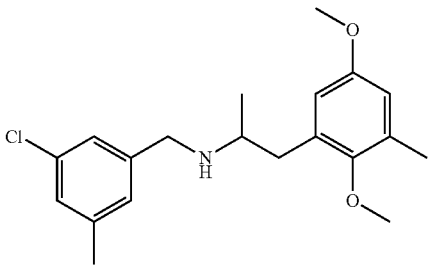 [SMILES: COc1cc(C)c(OC)c(CC(C)NCc2cc(C)cc(Cl)c2)c1] | NA |
| 2-29 | 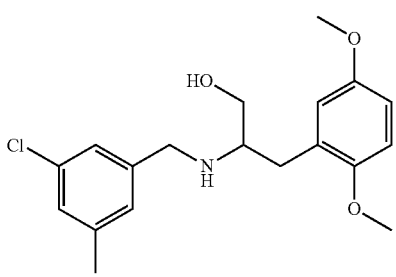 [SMILES: COc1ccc(OC)c(CC(CO)NCc2cc(C)cc(Cl)c2)c1] | 27 |
| 2-30 | 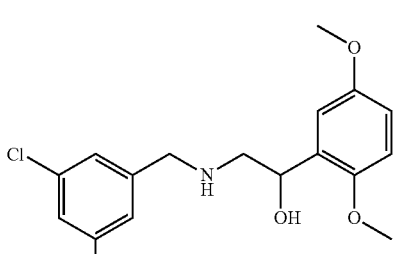 | 80 |
| 2-31 | 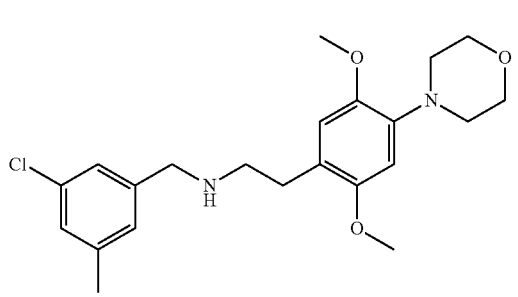 [SMILES: COc1cc(N2CCOCC2)c(OC)cc1CCNCc1cc(C)cc(Cl)c1] | 41 |

TABLE 5-continued
5HT2A Activity for Compounds 2-1 to Compounds 2-42
| No. | Structure | 5HT2A ACTIVITY (% Max Activation @ 0.3 uM) |
|---|---|---|
| 2-32 | 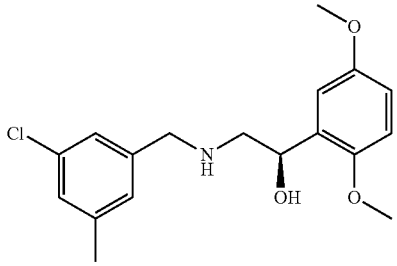 [SMILES: COc1ccc(OC)c([C@@H](O)CNCc2cc(C)cc(Cl)c2)c1] | 83 |
| 2-33 | 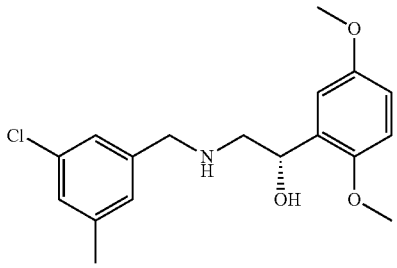 [SMILES: COc1ccc(OC)c([C@H](O)CNCc2cc(C)cc(Cl)c2)c1] | 39 |
| 2-34 | 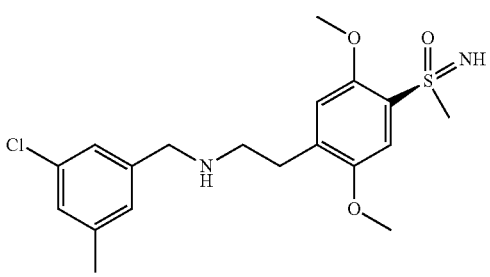 [SMILES: COc1cc([S@](C)(=N)=O)c(OC)cc1CCNCc1cc(C)cc(Cl)c1] | 56 |
| 2-35 | 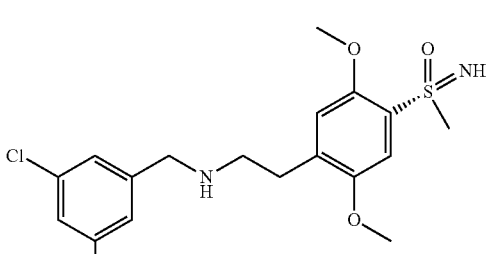 | 50 |
| 2-36 | 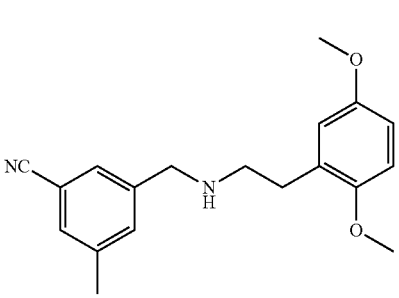 | 16 |

TABLE 5-continued

5HT2A Activity for Compounds 2-1 to Compounds 2-42

| No. | Structure | 5HT2A ACTIVITY (% Max Activation @ 0.3 uM) |
|---|---|---|
| 2-37 | 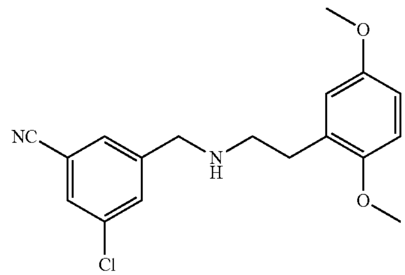 [SMILES: COc1ccc(OC)c(CCNCc2cc(Cl)cc(C#N)c2)c1] | NA |
| 2-38 | 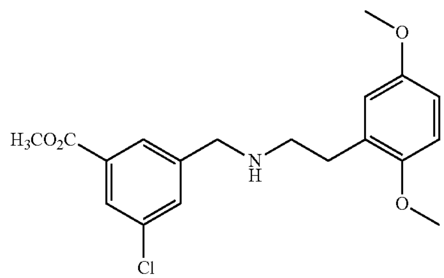 [SMILES: COC(=O)c1cc(Cl)cc(CNCCc2cc(OC)ccc2OC)c1] | NA |
| 2-39 | 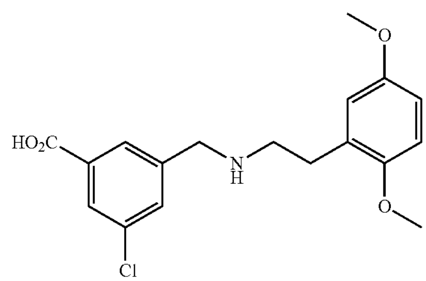 [SMILES: COc1ccc(OC)c(CCNCc2cc(Cl)cc(C(=O)O)c2)c1] | NA |
| 2-40 | 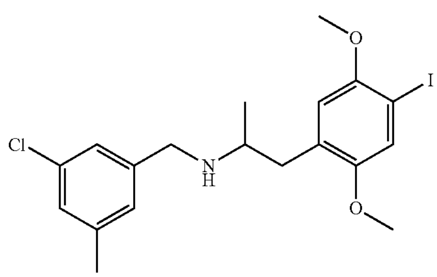 [SMILES: COc1cc(CC(C)NCc2cc(C)cc(Cl)c2)c(OC)cc1I] | NA |
| 2-41 | 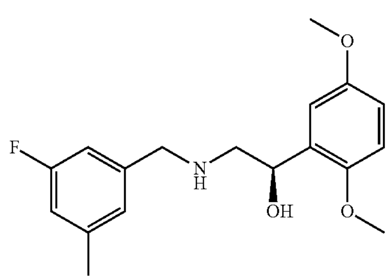 [SMILES: COc1ccc(OC)c([C@@H](O)CNCc2cc(C)cc(F)c2)c1] | 74 |

TABLE 5-continued

5HT2A Activity for Compounds 2-1 to Compounds 2-42

| No. | Structure | 5HT2A ACTIVITY (% Max Activation @ 0.3 uM) |
|---|---|---|
| 2-42 | 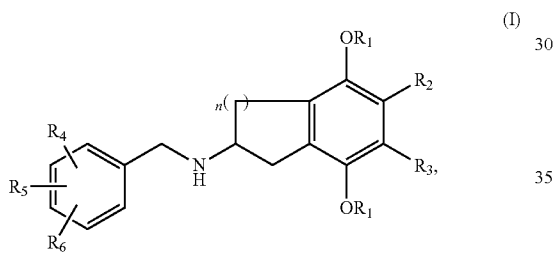 | NA |

NUMBERED EMBODIMENTS OF THE DISCLOSURE

In addition to the disclosure above, the Examples below, and the appended claims, the disclosure sets forth the following numbered embodiments.

1. A compound of Formula (I):

(I)

or a pharmaceutically acceptable salt thereof, wherein, $R_1$ is independently at each position hydrogen, $C_1$-$C_6$ alkyl or $C_1$-$C_6$ haloalkyl;

$R_2$ and $R_3$ are independently hydrogen, $C_1$-$C_6$ alkyl, $C_1$-$C_6$ haloalkyl, halogen, cyano, $OR_1$ or $SR_1$, wherein at least one of $R_2$ and $R_3$ is hydrogen;

$R_4$, $R_5$ and $R_6$ are independently hydrogen, $C_1$-$C_6$ alkyl, $C_1$-$C_6$ haloalkyl, halogen, cyano, $OR_1$, $SR_1$, O(C=O)($R_{12}$), or NH(C=O)($R_{12}$), wherein $R_{12}$ is $C_1$-$C_6$ alkyl; and n is an integer from 0-3.

2. The compound of embodiment 1, wherein $R_1$ is $C_1$-$C_6$ alkyl.
3. The compound of embodiment 1, wherein $R_1$ is methyl, ethyl, propyl, or isopropyl.
4. The compound of embodiment 1, wherein $R_1$ is methyl.
5. The compound of any one of embodiments 1-4, wherein $R_2$ is hydrogen, methyl or ethyl and $R_3$ is hydrogen.
6. The compound of any one of embodiments 1-4, wherein $R_2$ is halogen and $R_3$ is hydrogen.
7. The compound of any one of embodiments 1-4, wherein $R_2$ is hydrogen and $R_3$ is halogen.
8. The compound of any one of embodiments 1-7, wherein $R_4$ is $C_1$-$C_6$ alkyl.
9. The compound of any one of embodiments 1-8, wherein $R_4$ is methyl.
10. The compound of any one of embodiments 1-9, wherein $R_5$ is halogen.
11. The compound of any one of embodiments 1-10, wherein $R_5$ is chloro.
12. The compound of any one of embodiments 1-11, wherein $R_6$ is hydrogen.
13. The compound of any one of embodiments 1-12, wherein n is 1.
14. The compound of any one of embodiments 1-12, wherein n is 2.
15. The compound of embodiment 1, wherein the compound is:

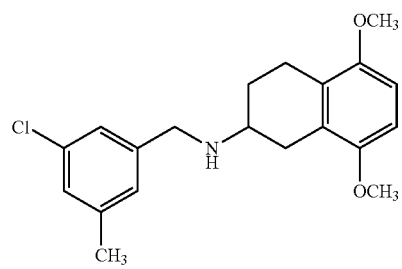

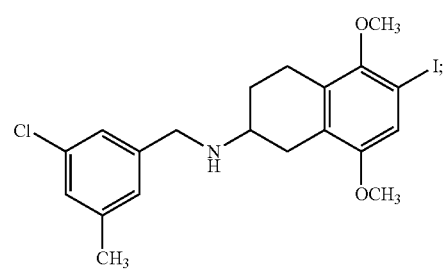

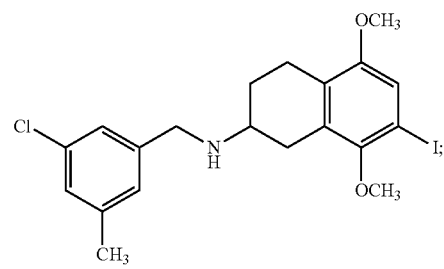

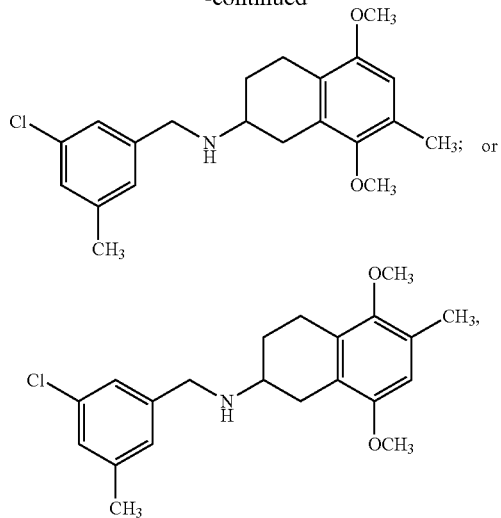

16. A compound of Formula (II):
(II),

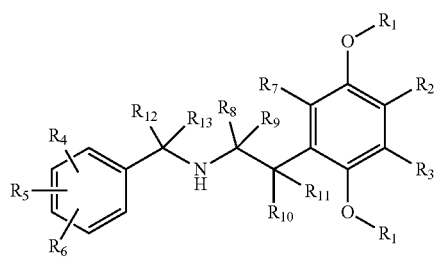

or a pharmaceutically acceptable salt thereof, wherein, $R_1$ is independently at each position hydrogen, $C_1$-$C_6$ alkyl, or $C_1$-$C_6$ haloalkyl;

$R_2$, $R_3$ and $R_7$ are independently hydrogen, heterocycle, $C_1$-$C_6$ alkyl, $C_1$-$C_6$ haloalkyl, halogen, cyano, $OR_1$, $S(O)(=NH)R_1$, $S(O)_2R_1$, $S(O)R_1$ or $SR_1$, wherein at least one of $R_2$ and $R_3$ is hydrogen;

$R_4$, $R_5$ and $R_6$ are independently hydrogen, $C_1$-$C_6$ alkyl, $C_1$-$C_6$ haloalkyl, halogen, cyano, $OR_1$, $SR_1$, (C=O)($R_{14}$), $O(C=O)(R_{14})$, $NO_2$, or $NH(C=O)(R_{14})$, wherein $R_{14}$ is $C_1$-$C_6$ alkyl, OH, or $OC_1$-$C_6$ alkyl;

$R_8$ and $R_9$ are independently hydrogen, $C_1$-$C_6$ alkyl, $C_1$-$C_4$ alkyl, $C_3$-$C_6$ cycloalkyl, $C_3$-$C_{10}$ cycloalkyl, $CH_2OH$, or $CH_2O$—$C_1$-$C_4$ alkyl; and $R_{10}$ and $R_{11}$ are independently hydrogen, halogen, $C_1$-$C_6$ alkyl, OH, $C_1$-$C_4$ alkyl, $C_3$-$C_6$ cycloalkyl, or $CH_2O$—$C_1$-$C_4$ alkyl;

$R_{12}$ is hydrogen, $CH_2OH$, $CH_2O$—$C_1$-$C_9$ alkyl, $C_3$-$C_{10}$ cycloalkyl, $CH_2OH$, or $CH_2O$—$C_1$-$C_4$ alkyl;

$R_{13}$ is hydrogen, $C_1$-$C_9$ alkyl, $C_3$-$C_{10}$ cycloalkyl, or $CH_2OH$, $CH_2O$—$C_1$-$C_4$ alkyl; and and n is an integer from 0-3.

17. The compound of embodiment 16, wherein $R_1$ is $C_1$-$C_6$ alkyl.

18. The compound of embodiment 17, wherein $R_1$ is methyl, ethyl, propyl, or isopropyl.

19. The compound of embodiment 18, wherein $R_1$ is methyl.

20. The compound of any one of embodiments 16-19, wherein $R_2$ and $R_3$ are hydrogen.

21. The compound of any one of embodiments 16-19, wherein $R_2$ is halogen and $R_3$ is hydrogen.

22. The compound of any one of embodiments 16-19, wherein $R_2$ is hydrogen and $R_3$ is halogen.

23. The compound of any one of embodiments 16-22, wherein $R_4$ is $C_1$-$C_6$ alkyl.

24. The compound of embodiment 23, wherein $R_4$ is methyl.

25. The compound of any one of embodiments 16-24, wherein $R_5$ is halogen.

26. The compound of embodiment 25, wherein $R_5$ is chloro.

27. The compound of any one of embodiments 16-26, wherein $R_6$ is hydrogen.

28. The compound of any one of embodiments 16-27, wherein $R_7$ is hydrogen.

29. The compound of any one of embodiments 16-28, wherein $R_8$ and $R_9$ are hydrogen.

30. The compound of any one of embodiments 16-29, wherein $R_{10}$ and $R_{11}$ are hydrogen, $C_1$-$C_4$ alkyl, $C_3$-$C_6$ cycloalkyl, or $CH_2O$—$C_1$-$C_4$ alkyl.

31. The compound of any one of embodiments 16-29, wherein $R_{10}$ and $R_1$ are fluoro.

32. The compound of any one of embodiments 16-31, wherein $R_{12}$ is $CH_2OH$, $CH_2O$—$C_1$-$C_4$ alkyl, $C_3$-$C_{10}$ cycloalkyl, $CH_2OH$, or $CH_2O$—$C_1$-$C_4$ alkyl.

33. The compound of any one of embodiments 16-32, wherein $R_{13}$ is $C_1$-$C_4$ alkyl or $C_3$-$C_6$ cycloalkyl.

34. The compound of any one of embodiments 16-33, wherein $R_{12}$ and $R_{13}$ are hydrogen.

35. The compound of embodiment 16, wherein the compound is:

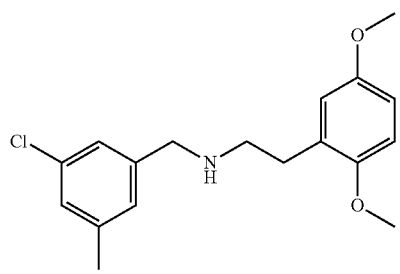 [SMILES: COc1ccc(OC)c(CCNCc2cc(C)cc(Cl)c2)c1]

or a pharmaceutically acceptable salt thereof.

36. The compound of embodiment 16, wherein the compound is:

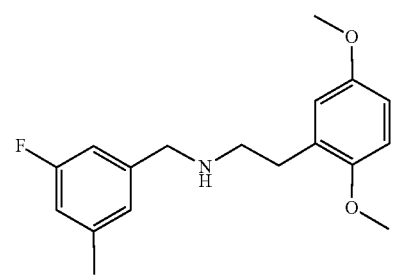

or a pharmaceutically acceptable salt thereof.

37. The compound of embodiment 16, wherein the compound is:

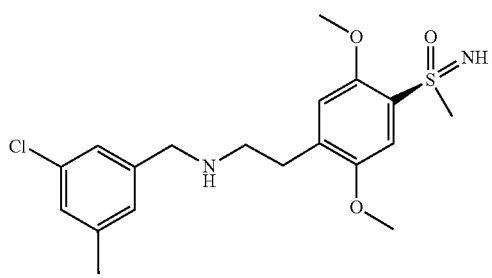 [SMILES: COc1cc([S@](C)(=N)=O)c(OC)cc1CCNCc1cc(C)cc(Cl)c1]

or a pharmaceutically acceptable salt thereof.

38. The compound of embodiment 16, wherein the compound is:

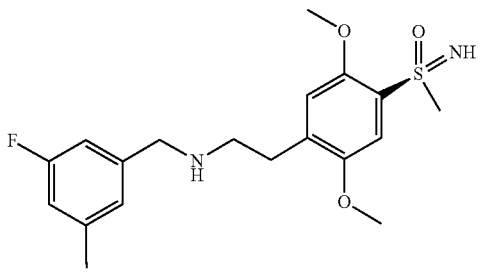 [SMILES: COc1cc([S@](C)(=N)=O)c(OC)cc1CCNCc1cc(C)cc(F)c1]

or a pharmaceutically acceptable salt thereof.

39. The compound of embodiment 16, wherein the compound is

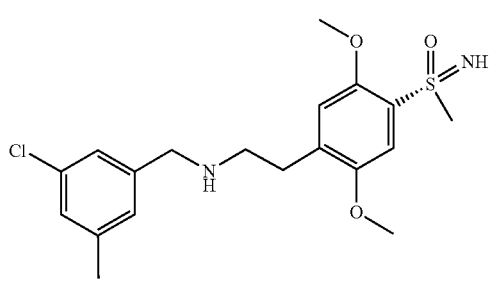 [SMILES: COc1cc([S@@](C)(=N)=O)c(OC)cc1CCNCc1cc(C)cc(Cl)c1]

or a pharmaceutically acceptable salt thereof.

40. The compound of embodiment 16, wherein the compound is

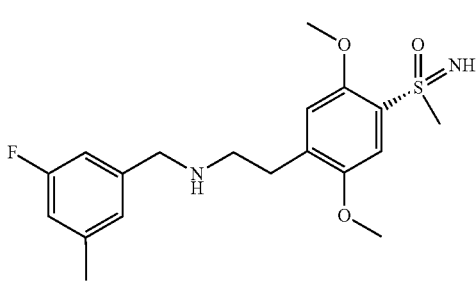 [SMILES: COc1cc([S@@](C)(=N)=O)c(OC)cc1CCNCc1cc(C)cc(F)c1]

or a pharmaceutically acceptable salt thereof.

41. A pharmaceutical composition comprising the compound of any one of embodiments 1-40 and a pharmaceutically acceptable excipient.

42. A method of treating a mental health disease or disorder, the method comprising administering a therapeutically effective amount of a compound of any one of embodiments 1-40.

43. The method of embodiment 42, wherein the mental health disease or disorder is a major depressive disorder, treatment resistant depression, substance use disorders or eating disorders.

44. A compound selected from one of the compounds of Table 1.

45. A compound selected from one of the compounds of Table 2.

46. The compound of embodiment 1, wherein Formula (I) is a compound of Formula (I-A)

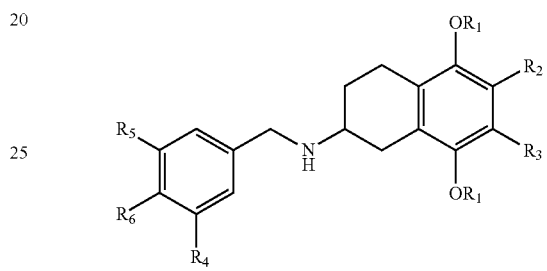

or a pharmaceutically acceptable salt thereof.

47. The compound of embodiment 16, wherein Formula (II) is a compound of Formula (II-A)

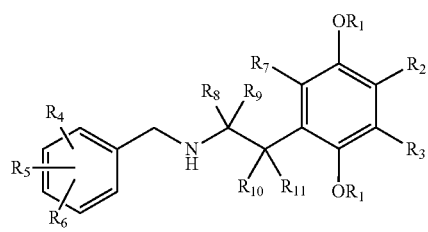

or a pharmaceutical acceptable salt thereof.

What is claimed is:

1. A method of treating a mental health disease or disorder, the method comprising administering a therapeutically effective amount of a compound of Formula (II-B):

Formula (II-B)

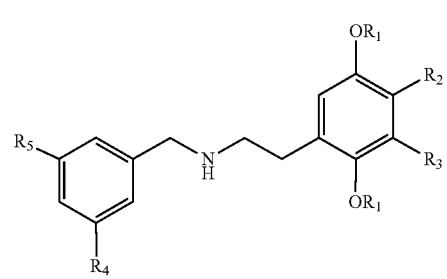

or a pharmaceutically acceptable salt thereof, wherein,

R$_1$ is independently at each position hydrogen, C$_1$-C$_6$ alkyl, or C$_1$-C$_6$ haloalkyl;

R$_2$ and R$_3$ are independently hydrogen, heterocycle, C$_1$-C$_6$ alkyl, C$_1$-C$_6$ haloalkyl, halogen, cyano, OR$_1$, S(O)(=NH) R$_1$, S(O)$_2$R$_1$, S(O)R$_1$ or SR$_1$, wherein at least one of R$_2$ and R$_3$ is hydrogen;

R$_4$ is hydrogen, C$_1$-C$_6$ alkyl, C$_1$-C$_6$ haloalkyl, halogen, cyano, OR$_1$, SR$_1$, (C=O)(R$_{14}$), O(C=O)(R$_{14}$), NO$_2$, or NH (C=O)(R$_{14}$), wherein R$_{14}$ is C$_1$-C$_6$ alkyl, OH, or OC$_1$-C$_6$ alkyl; and R$_5$ is halogen.

2. The method of claim 1, wherein the mental health disease or disorder is depression, substance use disorders, or eating disorders.

3. The method of claim 2, wherein the depression is major depressive disorder or treatment resistant depression.

4. The method of claim 2, wherein the eating disorders is major anorexia nervosa, bulimia nervosa, or binge eating.

5. The method of claim 1, wherein the compound is:

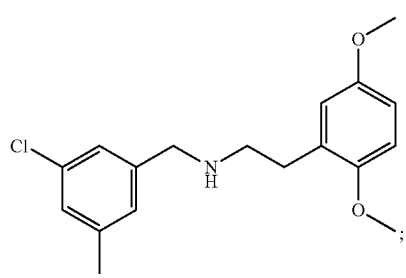

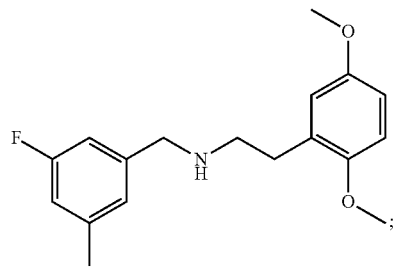

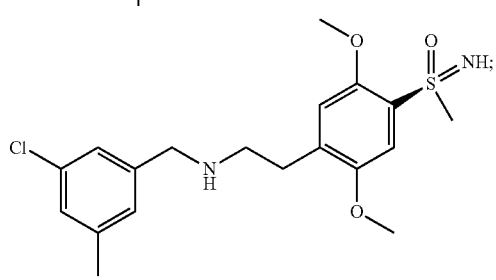

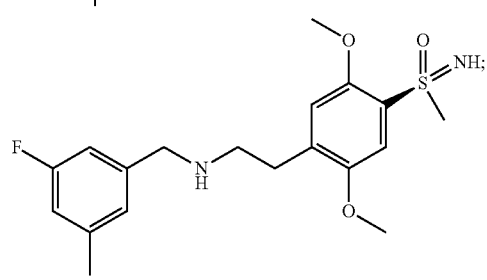

-continued

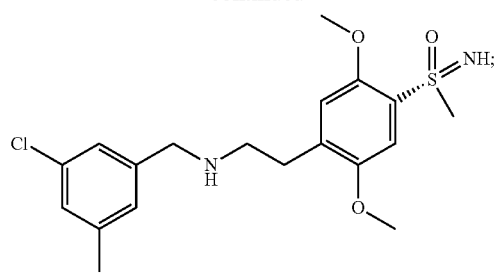

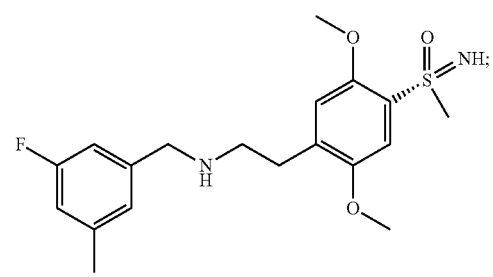

a pharmaceutically acceptable salt thereof.

6. The method of claim 1, wherein the compound is:

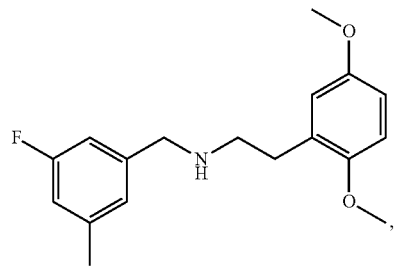 [SMILES: COc1ccc(OC)c(CCNCc2cc(C)cc(F)c2)c1]

or a pharmaceutically acceptable salt thereof.

7. The method of claim 1, wherein the compound is:

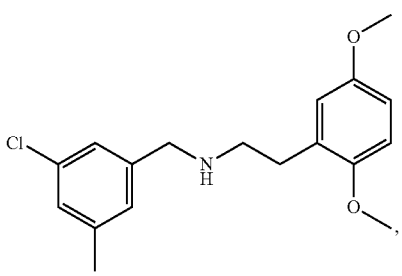 [SMILES: COc1ccc(OC)c(CCNCc2cc(C)cc(Cl)c2)c1]

or a pharmaceutically acceptable salt thereof.

8. The method of claim 1, wherein the compound is:

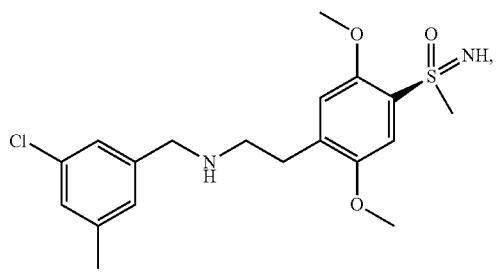 [SMILES: COc1cc([S@](C)(=N)=O)c(OC)cc1CCNCc1cc(C)cc(Cl)c1]

or a pharmaceutically acceptable salt thereof.

9. The method of claim 1, wherein the compound is:

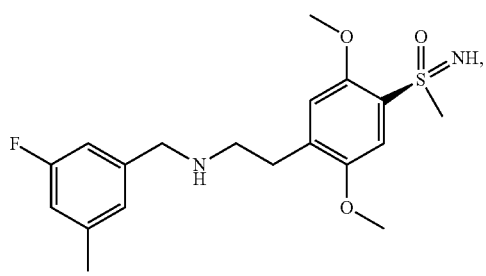 [SMILES: COc1cc([S@](C)(=N)=O)c(OC)cc1CCNCc1cc(C)cc(F)c1]

or a pharmaceutically acceptable salt thereof.

10. The method of claim 1, wherein the compound is:

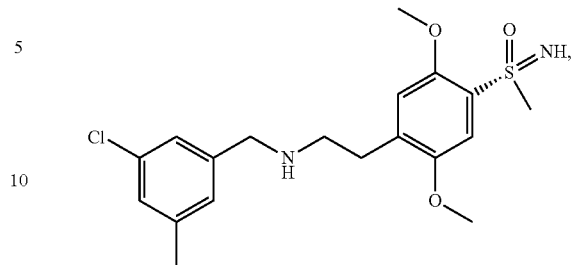

or a pharmaceutically acceptable salt thereof.

11. The method of claim 1, wherein the compound is:

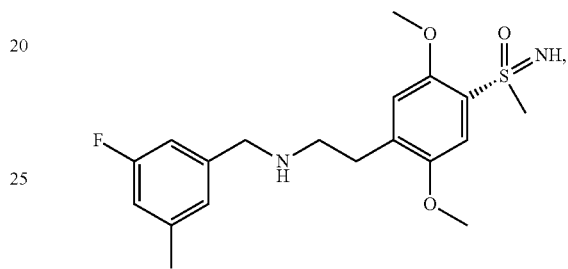

or a pharmaceutically acceptable salt thereof.

* * * * *